US008598329B2

(12) United States Patent (10) Patent No.: US 8,598,329 B2
McCarthy et al. (45) Date of Patent: Dec. 3, 2013

(54) POLYNUCLEOTIDE ENCODING A CYSTEINE PROTEASE

(75) Inventors: James McCarthy, Nolzay (FR); Mohamed Ben Amor, Korba (TN); Vincent Petiard, Tours (FR); Steve Tanksley, Dryden, NY (US); Chenwei Lin, Ithaca, NY (US)

(73) Assignees: Nestec S.A., Vevey (CH); Cornell University, Ithaca, NY (US)

( * ) Notice: Subject to any disclaimer, the term of this patent is extended or adjusted under 35 U.S.C. 154(b) by 75 days.

(21) Appl. No.: 12/941,557

(22) Filed: Nov. 8, 2010

(65) Prior Publication Data

US 2011/0126314 A1 May 26, 2011

Related U.S. Application Data

(63) Continuation of application No. 10/559,986, filed as application No. PCT/EP2004/006805 on Jun. 18, 2004, now abandoned.

(30) Foreign Application Priority Data

Jun. 20, 2003 (EP) ..................................... 03394056

(51) Int. Cl.
*C07H 21/04* (2006.01)
(52) U.S. Cl.
USPC ....................................................... 536/23.2
(58) Field of Classification Search
None
See application file for complete search history.

(56) References Cited

U.S. PATENT DOCUMENTS 6,103,514 A 8/2000 Natori

FOREIGN PATENT DOCUMENTS

| EP | 1033405 | 9/2000 |
|---|---|---|
| WO | 02/04617 | 1/2002 |
| WO | 02/42327 | 5/2002 |

OTHER PUBLICATIONS

Wishart et al, A single mutation converts a novel phosphotyrosine binding domain into a dual-specificity phosphatase. J Biol Chem. Nov. 10, 1995;270(45):26782-26785.*
Whisstock et al, Prediction of protein function from protein sequence and structure. Q Rev Biophys. Aug. 2003;36(3):307-40. Review.*
Schmid et al, A cysteine endopeptidase with a C-terminal KDEL motif isolated from castor bean endosperm is a marker enzyme for the ricinosome, a putative lytic compartment. Planta. Oct. 1998;206(3):466-75.*
Lepelley et al, Coffee cysteine proteinases and related inhibitors with high expression during grain maturation and germination. BMC Plant Biology 2012, 12:31-46.*

*Arabidopsis Thaliana* Protein Fragment Seq ID No: 36701, Database USPTO Geneseq Online, Oct. 17, 6pgs., 2000, XP 002310750.
*Arabidopsis thaliana* DNA fragment Seq ID No: 68333, Oct. 18, 2000, XP002494847.
Barker et al., Protein Information Resource: a community resource for expert annotation of protein data. Nucleic Acids Res. Jan. 1, 2001;29(1): 29-32.
Beuning, L., et al., "A Gene Database from Fruit Tree Species," Submitted (Jan. 2003) to the EMBL/GenBank/DDBJ databases XP002269563.
"Cloning of two cysteine proteinase genes, CysP1 and CysP2, from soybean cotyledons by cDNA representational difference analysis," Database UniProt Online, Oct. 1, 2003, XP002310748.
Fay, L, et al., "Contribution of Mass Spectrometry to the Study of the Maillard Reaction in Food," Mass Spectrometry Reviews, vol. 24, pp. 487-507, (2005).
Fischer et al., The families of papain- and legumain-like cysteine proteinases from embryonic axes and cotyledons of Vicia seeds: developmental patters, intracellular localization and functions in globulin proteolysis, Plant Molecular Biology vol. 43, No. 1 / May 2000.
Gayle et al., Identification of regions in interleukin-1 alpha important for activity, J Biol Chem. Oct 15, 1993;268 (29):22105-11.
Guo et al., Protein tolerance to random amino acid change, Proc Natl Acad Sci U S A, Jun. 22;101(25):9205-9210, Epub Jun. 14, 2004.
Haas, B.J., et al., "Full-length messenger RNA sequences greatly improve genome annotation," Genome Biol. 3(6): RESEARCH0029-RESEARCH0029 (2002), XP002269564.
Kaneko, T., et al., "Structural analysis of *Arabidopsis thaliana* chromosome 5. Xl.,"Submitted(Apr.-199) to the EMBL/GenBank/DDBJ databases, XP002269565.
Kohara, Y., et al., "Ipomoea nil cDNA clone:jm19n11, 3" end, single read," Sumitted (Dec. 8, 2002) to the EMBL/Genbank/DDBJ databases, XP002269562.
Leroy, T., et al., "Genetically Modified Coffee Plants Expressing the *Bacillus Thuringiensis* CRY1AC Gene for Resistance to Leaf Miner," Plant Cell Reports, vol. 19, pp. 382-389, (2000).
Ling, J., et al., Cloning of Two Cysteine Proteinase Genes, CYSP1 and CYSP2, From Soybean Cotyledons by CDNA Representational Difference Analysis,: Biochimica et Biophysica Acta—Gene Structure and Expression, Elsevier, Amsterdam, NL, vol. 1627, No. 2-3, pp. 129-139, Jun. 19, 2003, XP004431612.
Marraccini, P., et al., "Molecular Cloning of the Complete 11S Seed Storage Protein Gene of Coffee Arabica and Promoter Analsis in Transgenic Tobacco Plants," Plant Physiol. Biochem., vol. 37, No. 4, pp. 273-282, (1999), XP002197483.
Natori, S., et al., "Sequence 74 From Patent US 6103514," Database USPTO Proteins Online, Aug. 15, 2000, 1 pg., XP002310749.
Nong, V., et al., "CDNA Cloning for a Putative Cysteine Proteinase From Developing Seeds of Soybean (Abstract)," Biochim. Biophys. Acta, vol. 1261, No. 3, pp. 435-438, 2 pages.., (1995) XP002269560.
Schaller, A., et al., "Molecular cloning of a tomato leaf cDNA encoding an aspartic protease, a systemic wound response protein," Plant Mol. Biol. 31(5) : 1073-1077 (1996), XP002269566.

(Continued)

*Primary Examiner* — Sheridan Swope
(74) *Attorney, Agent, or Firm* — K&L Gates LLP

(57) ABSTRACT

The present invention relates to isolated polynucleotides encoding cysteine proteinases; cysteine proteinase inhibitors; and aspartic endoproteinases. The invention also relates to a transformed host cell, preferably a plant cell, in which over- or under-expression of these polynucleotides result in altered levels of coffee flavor precursor levels, specifically, amino group-containing molecules such as amino acids, peptides and proteins, in green coffee grains.

8 Claims, 22 Drawing Sheets

(56) References Cited

OTHER PUBLICATIONS

Schmid et al., "A cysteine endopeptidase with a C-terminal KDEL motif isolated from castor bean endosperm is a marker enzyme for the ricinosome, a putativelytic compartment," Planta (1998) 206:466-475 XP55003036.

Sugawara, H. et al., "Uniprot—The Universal Protein Knowledgebase," Database UniProt Online Jun. 1, 2001, Cysteine Proteinase Inhibitor, Sequence From Nucleic Acid, 2 pgs. XP002310747.

Whisstock et al., Prediction of protein function from protein sequence and structure, Q Rev Biophys. Aug. 2003;36 (3):307-40, Review.

Yamada, K., et al., "Full Length CDNA of Gene AT3G54940 (GI: 15233134)," Submitted to the EMBL/GenBank/DDBJ databases, 1 pg. Dec. 2001, XP002269561.

\* cited by examiner

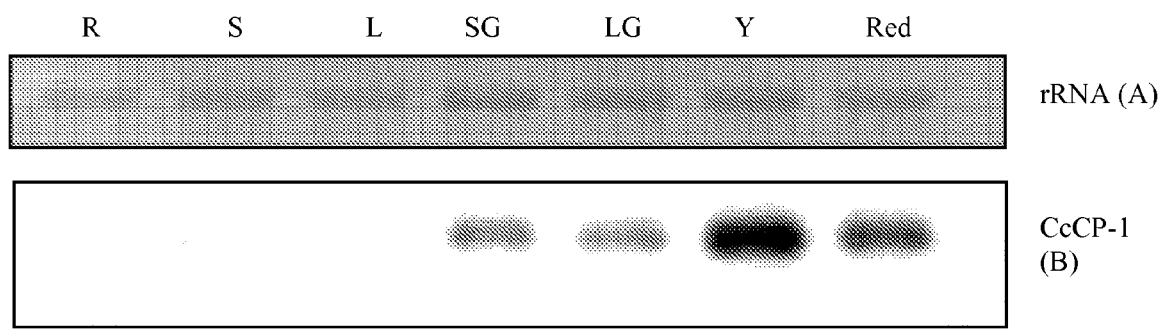
Figure 1: Northern blot analysis of the expression of the cysteine proteinase (CcCP1) gene in different tissues of *Coffea arabica*.

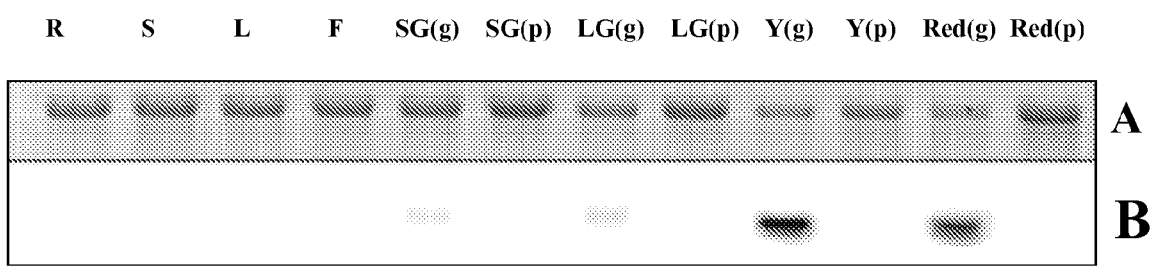
Figure 2A: Northern blot analysis of the expression of the Cysteine proteinase CcCP-1 gene in different tissues of *Coffea arabica*.

CcCP-1 (SEQ ID NO: 46)
A.tha (SEQ ID NO: 47)
G. max GMCP3 (SEQ ID NO: 48)
V. sat CPR4 (SEQ ID NO: 49)
G. max GmPM33 (SEQ ID NO: 50)
P. vul (SEQ ID NO: 51)
S. mel (SEQ ID NO: 52)
N. tab (SEQ ID NO: 53)
L. esc (SEQ ID NO: 54)
V. faba (SEQ ID NO: 55)

Figure 2B: Alignment of the full sequence of the protein encoded by CcCP-1 cDNA with other full-length cysteine proteinases available in the NCBI database.

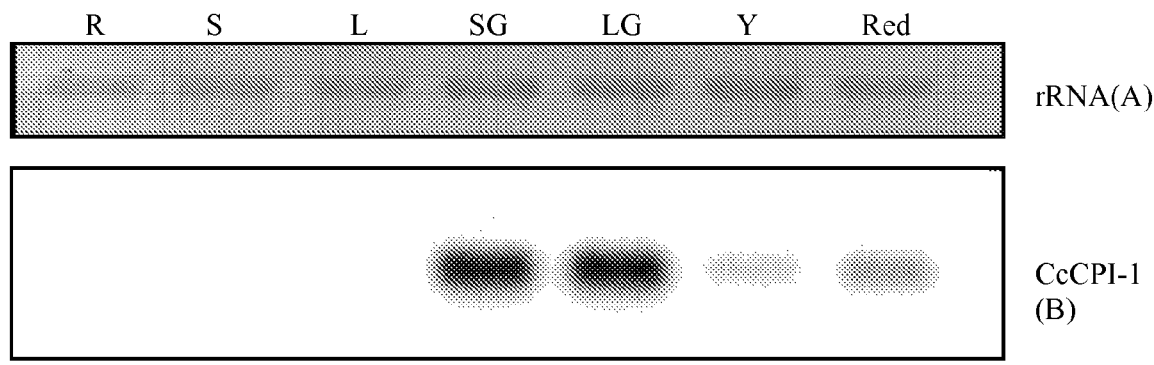
Figure 3: Northern blot analysis of the expression of the cysteine proteinase inhibitor (CcCPI-1) gene in different tissues of *Coffea arabica*.
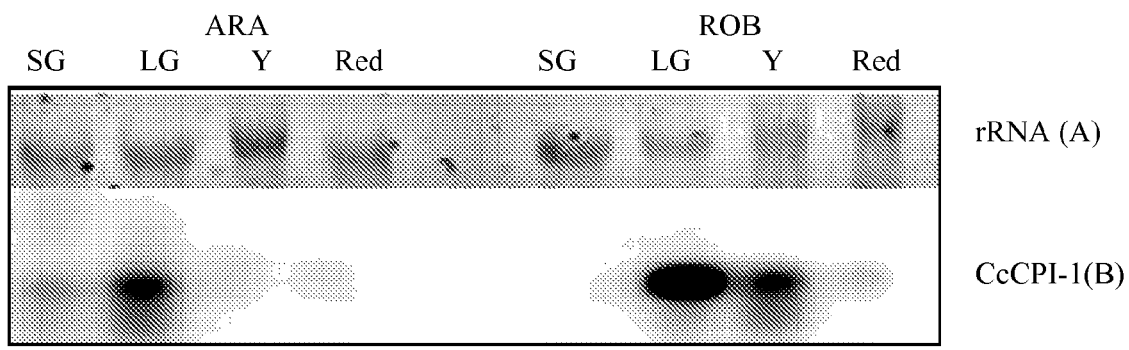
Figure 4: Northern blot analysis of the expression of the cysteine proteinase inhibitor gene (CcCPI-1) at different cherry development stages for *Coffea arabica* (ARA) and *Coffea canephora* (ROB).

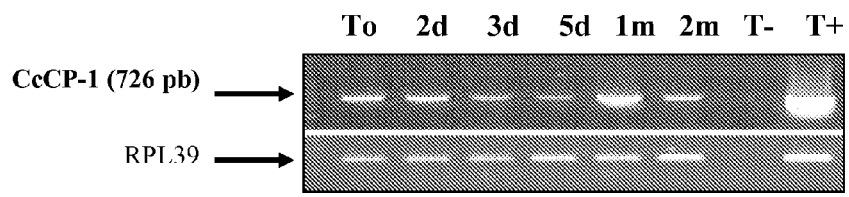
Figure 5. RT-PCR analysis of the expression of *CcCP-1* during *Coffea arabica* grain germination.
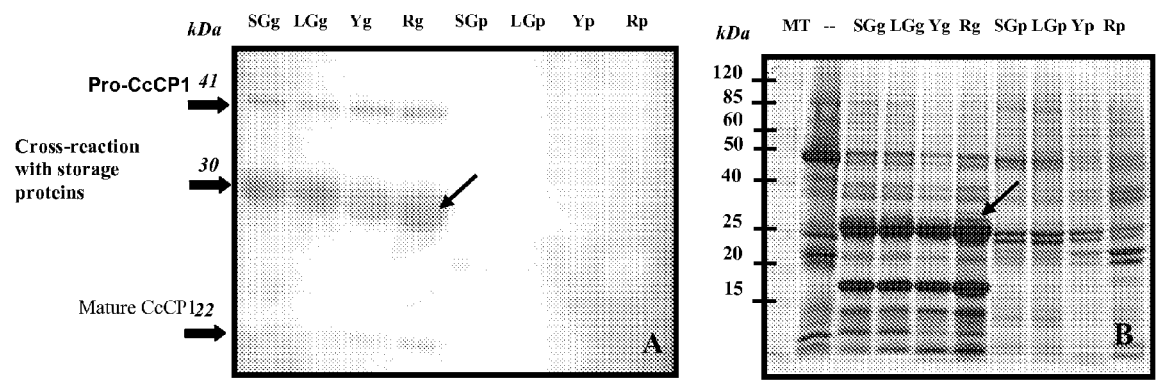
Figure 6A: Western-blot analysis of the expression of CcCP1 protein (A).

CPI-1       (SEQ ID NO: 56)
M. dosmest  (SEQ ID NO: 57)
Sunflower   (SEQ ID NO: 58)
R. obtusif  (SEQ ID NO: 59)
A. thaliana (SEQ ID NO: 60)

Figure 6B: Optimal alignment of the complete protein encoded by CcCPI-1 cDNA with other homologous full-length cysteine proteinases available in the NCBI.

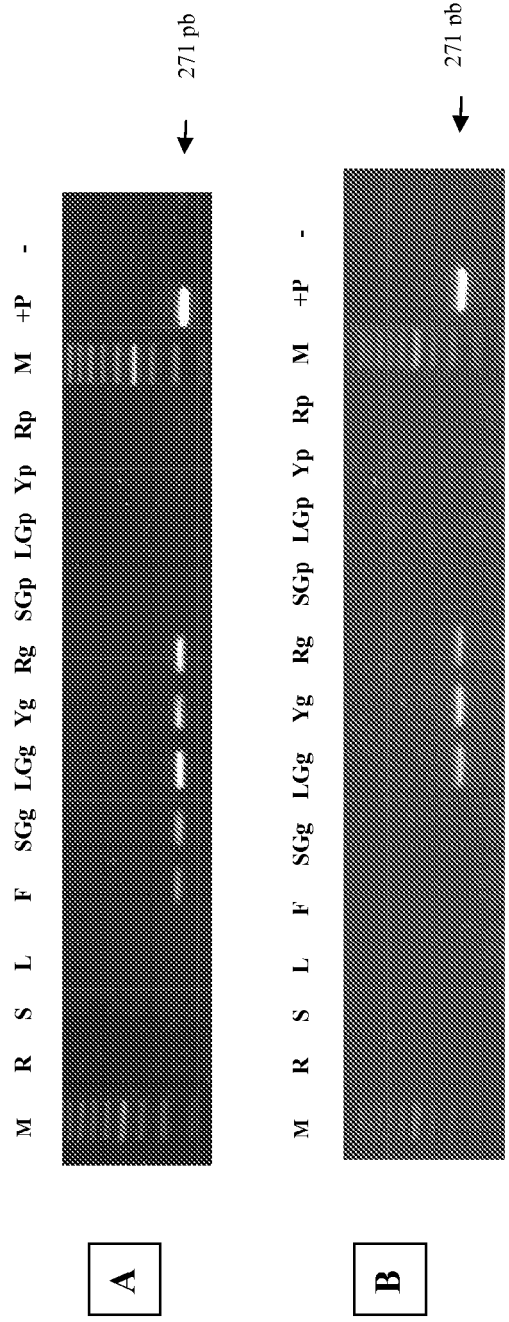
Figure 7: RT-PCR analysis of the expression of CcCPI-1 gene in different tissues of *Coffea arabica* CCCA2 (A) *and Coffea robusta* FRT-32 (B).

Figure 8: Optimal alignment of the complete protein encoded by CcCPI-2 cDNA with other homologous full-length cysteine proteinases available in the NCBI.

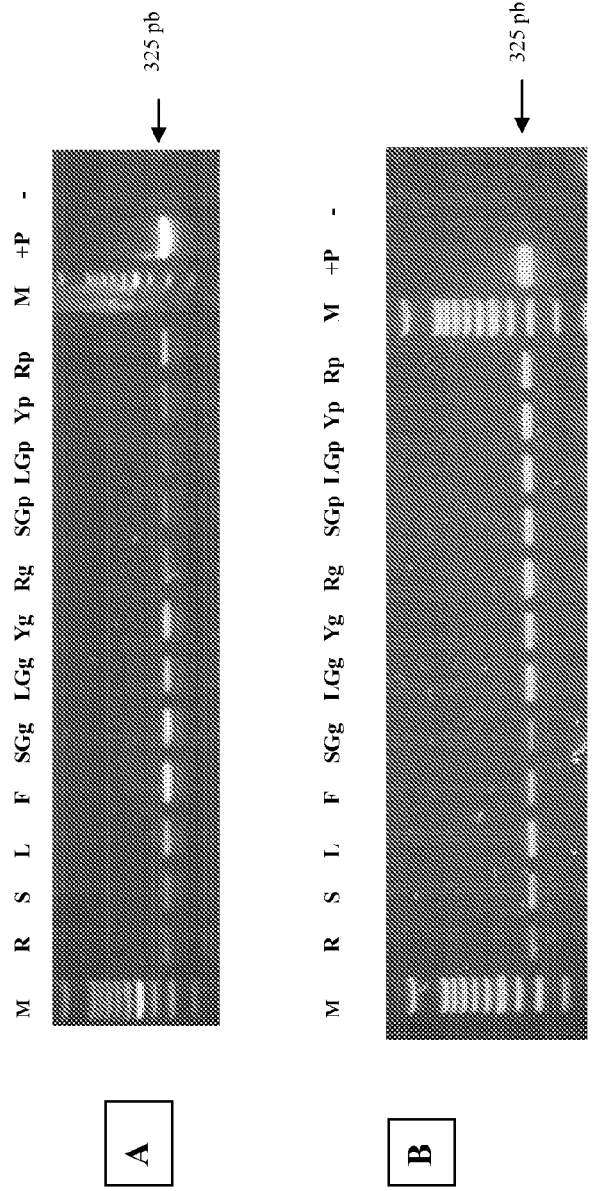
Figure 9: RT-PCR analysis of the expression of CcCPI-2 gene in different tissues of *Coffea arabica* CCCA2 (A) *and Coffea robusta* FRT-32 (B).

| | | | | | | | | | | | | | | | | | | | | | | | |
|---|---|---|---|---|---|---|---|---|---|---|---|---|---|---|---|---|---|---|---|---|---|---|---|
| 1 | M | A | S | A | F | P | H | L | L | L | T | T | L | A | A | I | C | L | F | S | D | V | P | S | A | A | L | G | G | R | P | K | D | A | L | V | G | G | W | CcCPI-3 |
| 1 | M | N | Q | R | F | C | C | L | I | V | L | - | - | - | - | - | - | F | L | S | V | V | P | L | L | A | A | G | D | R | - | K | G | A | L | V | G | G | W | Citrus x paradisi |
| 1 | M | V | P | K | P | L | S | L | L | L | F | - | - | - | - | - | - | L | L | A | L | S | A | A | V | G | G | R | - | K | L | V | A | A | G | G | W | A. deliciosa |
| 1 | M | T | S | K | V | V | F | L | L | L | L | - | - | - | - | - | - | S | L | - | V | V | L | L | P | L | Y | A | S | - | A | A | A | R | V | G | G | W | A. thaliana |

| | | | | | | | | | | | | | | | | | | | | | | | |
|---|---|---|---|---|---|---|---|---|---|---|---|---|---|---|---|---|---|---|---|---|---|---|---|
| 41 | S | - | K | A | D | P | K | D | P | E | V | L | E | N | G | K | F | A | I | D | E | H | N | K | E | A | G | T | K | L | E | F | K | T | V | V | F | A | Q | K | CcCPI-3 |
| 33 | K | P | I | E | D | P | K | E | K | H | M | E | I | G | Q | F | A | V | T | E | Y | N | K | Q | S | A | L | K | F | E | S | V | E | K | G | E | T | Citrus x paradisi |
| 33 | R | P | I | E | S | L | N | S | A | E | V | Q | D | V | A | Q | F | A | V | S | E | H | N | K | Q | A | N | D | E | L | Q | Y | Q | S | V | V | R | G | Y | T | A. deliciosa |
| 32 | S | P | I | S | N | V | T | D | P | Q | V | E | I | G | E | F | A | V | S | E | Y | N | K | R | S | E | S | G | L | K | F | E | T | V | S | G | E | T | A. thaliana |

| | | | | | | | | | | | | | | | | | | | | | | | |
|---|---|---|---|---|---|---|---|---|---|---|---|---|---|---|---|---|---|---|---|---|---|---|---|
| 80 | Q | V | V | A | G | T | N | Y | K | I | V | I | K | A | L | D | G | T | - | A | S | N | L | Y | E | A | I | V | W | V | K | P | W | L | K | F | K | L | T | CcCPI-3 |
| 73 | Q | V | V | S | G | T | N | Y | Y | R | L | L | V | V | K | D | G | P | - | S | T | K | F | E | A | V | V | W | E | K | P | W | H | F | K | S | L | T | Citrus x paradisi |
| 73 | Q | V | V | A | G | T | N | Y | Y | R | L | V | I | A | A | N | D | G | A | - | V | V | G | N | Y | E | A | V | V | W | D | K | P | W | M | H | F | R | N | L | T | A. deliciosa |
| 72 | Q | V | V | S | G | T | N | Y | Y | R | L | K | V | A | A | N | D | G | D | G | V | S | K | N | Y | L | A | I | V | W | D | K | P | W | M | K | F | R | N | L | T | A. thaliana |

| | | | | | | |
|---|---|---|---|---|---|---|
| 119 | S | F | R | K | L | P | (SEQ ID NO: 65) | CcCPI-3 |
| 112 | S | F | F | K | P | M | V | K | (SEQ ID NO: 66) | Citrus x paradisi |
| 112 | S | F | R | K | V | (SEQ ID NO: 67) | A. deliciosa |
| 112 | S | F | E | P | A | N | N | G | R | F | L | (SEQ ID NO: 68) | A. thaliana |

Figure 10: Optimal alignment of the complete protein encoded by CcCPI-3 cDNA with other homologous full-length cysteine proteinases available in the NCBI.

Figure 11: Optimal alignment of the complete protein encoded by CcCPI-4 cDNA with other homologous full-length cysteine proteinases available in the NCBI.

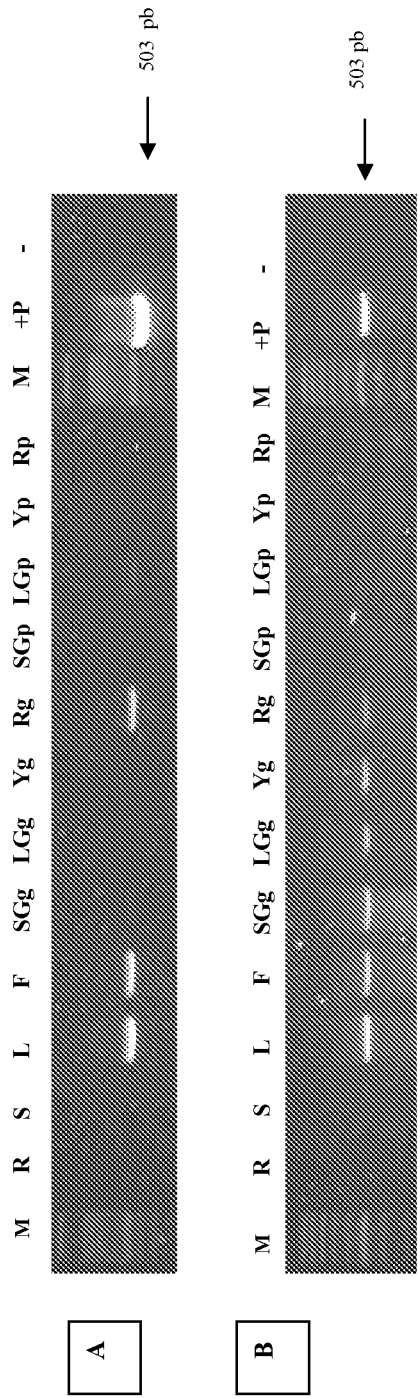
Figure 12: RT-PCR analysis of the expression of CcCPI-4 gene in different tissues of *Coffea arabica* CCCA2 (Panel A) and of *Coffea robusta* FRT-32 (Panel B)

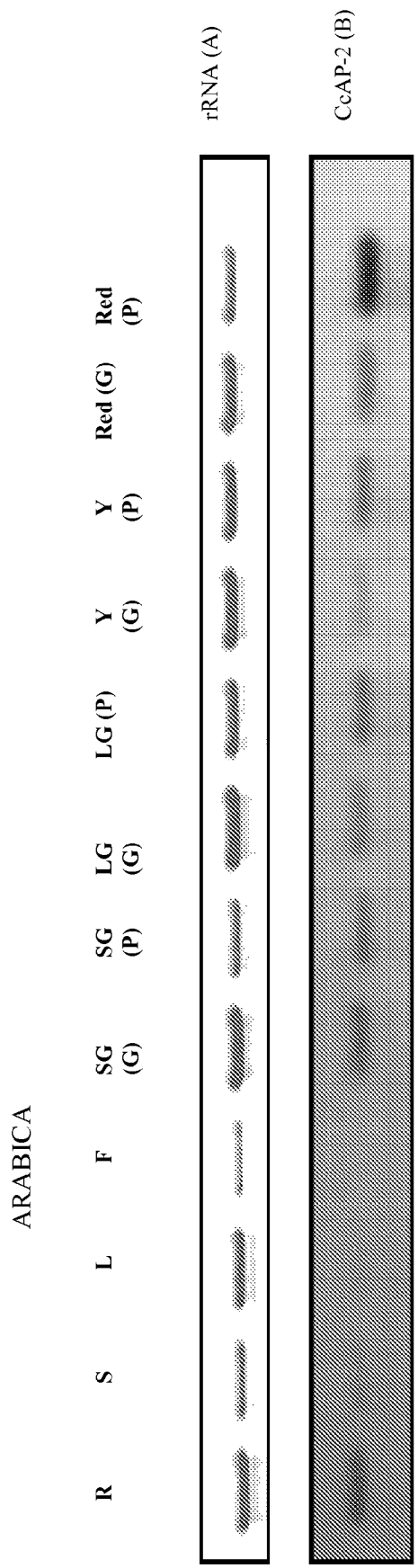
Figure 13: Northern blot analysis of the expression of the aspartic proteinase 2 (CcAP2) gene in different tissues of *Coffea arabica*.

```
   1 gcttacatcttaaatcctgattttatagattcgcctttcgtgaagttcaatcttcgcagtcgctcactaacattggt
  81 agacatacttcgatt ATG AAA ATG GGG AAG GCT TTC CTT TTT GCC GTT GTA TTG GCT GTG ATC
   1                 M   K   M   G   K   A   F   L   F   A   V   V   L   A   V   I 144 TTA GTG GCG GCT ATG AGC ATG GAG ATC ACA GAA AGA GAT TTG GCT TCT GAG GAA AGC TTG
  17  L   V   A   A   M   S   M   E   I   T   E   R   D   L   A   S   E   E   S   L 204 TGG GAC TTG TAC GAA AGA TGG AGG AGC CAT CAT ACT GTT TCT CGA GAC CTT TCT GAG AAA
  37  W   D   L   Y   E   R   W   R   S   H   H   T   V   S   R   D   L   S   E   K 264 CGA AAG CGC TTT AAT GTT TTC AAG GCA AAT GTC CAT CAC ATT CAC AAG GTG AAC CAG AAG
  57  R   K   R   F   N   V   F   K   A   N   V   H   H   I   H   K   V   N   Q   K 324 GAC AAG CCT TAC AAG CTG AAA CTC AAC AGT TTC GCT GAT ATG ACC AAC CAC GAG TTC AGG
  77  D   K   P   Y   K   L   K   L   N   S   F   A   D   M   T   N   H   E   F   R 384 GAA TTC TAC AGT TCT AAG GTG AAA CAT TAC CGG ATG CTC CAC GGC AGT CGT GCT AAT ACT
  97  E   F   Y   S   S   K   V   K   H   Y   R   M   L   H   G   S   R   A   N   T 444 GGA TTT ATG CAT GGG AAG ACT GAA AGT TTG CCA GCC TCC GTT GAT TGG AGA AAG CAA GGA
 117  G   F   M   H   G   K   T   E   S   L   P   A   S   V   D   W   R   K   Q   G 504 GCC GTG ACT GGC GTC AAG AAT CAA GGC AAA TGT GGT AGC TGT TGG GCA TTT TCA ACT GTG
 137  A   V   T   G   V   K   N   Q   G   K   C   G   S   C   W   A   F   S   T   V 564 GTT GGA GTC GAG GGA ATC AAC AAA ATC AAA ACA GGC CAA TTA GTT TCT CTG TCC GAG CAA
 157  V   G   V   E   G   I   N   K   I   K   T   G   Q   L   V   S   L   S   E   Q 624 GAA CTT GTT GAC TGT GAA ACG GAC AAT GAA GGA TGC AAC GGA GGA CTC ATG GAA AAT GCA
 177  E   L   V   D   C   E   T   D   N   E   G   C   N   G   G   L   M   E   N   A 684 TAC GAG TTT ATT AAG AAA AGT GGG GGA ATA ACA ACT GAG AGG CTA TAT CCC TAC AAG GCA
 197  Y   E   F   I   K   K   S   G   G   I   T   T   E   R   L   Y   P   Y   K   A 744 AGA GAT GGC AGC TGT GAT TCG TCA AAG ATG AAT GCC CCT GCT GTG ACT ATT GAT GGG CAT
 217  R   D   G   S   C   D   S   S   K   M   N   A   P   A   V   T   I   D   G   H 804 GAA ATG GTA CCC GCA AAC GAT GAG AAT GCC TTG ATG AAA GCT GTT GCT AAC CAG CCT GTA
 237  E   M   V   P   A   N   D   E   N   A   L   M   K   A   V   A   N   Q   P   V 864 TCA GTA GCT ATA GAT GCG TCT GGC TCT GAC ATG CAA TTT TAT TCA GAG GGT GTA TAC GCT
 257  S   V   A   I   D   A   S   G   S   D   M   Q   F   Y   S   E   G   V   Y   A 924 GGA GAC TCG TGT GGC AAT GAG CTT GAT CAT GGC GTG GCG GTC GTC GGC TAC GGG ACT GCT
 277  G   D   S   C   G   N   E   L   D   H   G   V   A   V   V   G   Y   G   T   A 984 CTT GAC GGT ACT AAA TAC TGG ATA GTG AAG AAC TCA TGG GGA ACA GGA TGG GGA GAA CAG
 297  L   D   G   T   K   Y   W   I   V   K   N   S   W   G   T   G   W   G   E   Q 1044 GGC TAT ATC AGG ATG CAA CGT GGT GTT GAT GCT GCT GAA GGC GGA GTT TGT GGG ATA GCA
 317  G   Y   I   R   M   Q   R   G   V   D   A   A   E   G   G   V   C   G   I   A 1104 ATG GAG GCC TCC TAT CCA CTT AAA TTG TCC TCC CAC AAT CCA AAA CCA TCC CCA CCT AAG
 337  M   E   A   S   Y   P   L   K   L   S   S   H   N   P   K   P   S   P   P   K 1164 GAC GAC CTC TAG attgatcctcttatatatatacatatatatatatatttcagtagattcattgaattttagttac
 357  D   D   L   *
1240 agactacgcgcttcTGaagacttagatcatctctaggcatagatttatgtaatcctgctcctgtgatggtttgaataaac
1320 aataagtagtactaataaaaaaaaaaaaaaaaaaaaaaaaaaaaaaa (SEQ ID NO: 15)
```

Figure 14: cDNA sequence (SEQ ID NO: 15) and its deduced amino acid sequence of CcCP-4 (SEQ ID NO: 16). Lowercase: 5' and 3' non-translated regions; Uppercase: Open reading frame; Bold character: amino acid sequency; *: stop codon.

```
  1   MKMGKAFLFAVVLAVILVAAMSMEITERDLASEESLWDLYERWRSHHTVSRDLSEKRKRFNVEKANVHHIHKVNQKDKPY  CcCP-4 KDDL
  1   --------------------------------------------------------------------------------  CcCP-4 KDEL

81   KLKLNSFADMTNHEFREFYSSKVKHYRMLHGSRANLGFMHCKTESLPASVDWRKQGAVTCVKNQGKCGSCWAFSTVVGVE  CcCP-4 KDDL
  1   -----------------------------------------------------------GKCGSCWAFSTVVGVE      CcCP-4 KDEL

161   GINKIKTGQLVSISEQELVDCETDNEGCNGGLMENAYEFIKKSGGITTERLYPYKARDGSCDSSKMNAPAVTIDGHEMVP  CcCP-4 KDDL
 17   GINKIKTGQLVSISEQELVDCETDNEGCNGGLMENAYEFIKKSGGITTERLYPYKARDGSCDSSKMNAPAVTIDGHEMVP  CcCP-4 KDEL

241   ANDENALMKAVANQPVSVAIDASGSDMQFYSEGVYAGDSCGNELDHGVAVVGYGTALDGTKTWIVKNSWGTGWGEQGYIR  CcCP-4 KDDL
 97   ANDENALMKAVANQPVSVAIDASGSDMQFYSEGVYFGDSCGNELDHGVAVVGYGTALDGTKTWIVKNSWGTGWGEQGYIR  CcCP-4 KDEL

321   MQRGVDAAEGGVCGIAMEASYPLKLSSHNPKPSPPKDDL  .(SEQ ID NO: 86)                          CcCP-4 KDDL
177   MQRGVDAAEGGVCGIAMEASYPLKLSSHNPKPSPPKDEL  .(SEQ ID NO: 87)                          CcCP-4 KDEL

Decoration 'Decoration #1': Shade (with solid black) residues that match CcCP-4 KDEL exactly.
```

Figure 17. The complete open reading frame of CcCP-4 (KDDL) and the partial open reading frame of CcCP-4 (KDEL).

Figure 19. Northern blot analysis of the expression of the Cysteine proteinase CcCP-4 gene in different tissues of *Coffea arabica*.

Figure 20. RT-PCR analysis of the expression of CcCP-4 in the whole grain during germination.

SEQUENCE LISTING

```
<160> NUMBER OF SEQ ID NOS: 100

<210> SEQ ID NO 1
<211> LENGTH: 1543
<212> TYPE: DNA
<213> ORGANISM: Coffea canephora
<220> FEATURE:
<221> NAME/KEY: mRNA
<222> LOCATION: (1)..(1543)
<223> OTHER INFORMATION: mRNA
<220> FEATURE:
<221> NAME/KEY: CDS
<222> LOCATION: (122)..(1315)
<223> OTHER INFORMATION: CDS

<400> SEQUENCE: 1
aagcagtggt aacaacgcag agtacgcggg ggacactcct ccccgttcca ttccagacca      60
gggtccaaaa ccaccgtcca agagaggagc agactgcaga gtgatacata caggcacaaa     120 g atg atg atg aca agc gga ggt ctg atg cta acc tgc act ctg gct att     169
  Met Met Met Thr Ser Gly Gly Leu Met Leu Thr Cys Thr Leu Ala Ile
  1               5                   10                  15
```

```
acc ctc tta tcc tgc gca ctc atc tct tca acc act ttc caa cat gaa    217
Thr Leu Leu Ser Cys Ala Leu Ile Ser Ser Thr Thr Phe Gln His Glu
        20              25              30 att cag tat cga gta caa gac ccg tta atg ata cgc caa gtc acc gac    265
Ile Gln Tyr Arg Val Gln Asp Pro Leu Met Ile Arg Gln Val Thr Asp
    35              40              45 aat cac cac cac cgc cac cac cca ggt agg tct tct gca aac cat cgt    313
Asn His His His Arg His His Pro Gly Arg Ser Ser Ala Asn His Arg
50              55              60 cta ctg ggc acc acc aca gag gtt cac ttc aag tcc ttc gtg gag gag    361
Leu Leu Gly Thr Thr Thr Glu Val His Phe Lys Ser Phe Val Glu Glu
65              70              75              80 tac gag aaa act tac tct acg cac gag gag tac gtg cac cgc ctg ggg    409
Tyr Glu Lys Thr Tyr Ser Thr His Glu Glu Tyr Val His Arg Leu Gly
            85              90              95 att ttc gcc aag aac ctc atc aag gcc gcg gag cac cag gcc atg gac    457
Ile Phe Ala Lys Asn Leu Ile Lys Ala Ala Glu His Gln Ala Met Asp
                100             105             110 ccc tcc gca atc cac ggc gtc acc cag ttc tct gat ctc acc gag gag    505
Pro Ser Ala Ile His Gly Val Thr Gln Phe Ser Asp Leu Thr Glu Glu
            115             120             125 gag ttt gag gct acg tac atg ggc ctt aaa ggt ggc gct gga gtt ggt    553
Glu Phe Glu Ala Thr Tyr Met Gly Leu Lys Gly Gly Ala Gly Val Gly
    130             135             140 ggg acc acc cag ctg ggg aaa gat gat ggg gat gag agt gca gca gag    601
Gly Thr Thr Gln Leu Gly Lys Asp Asp Gly Asp Glu Ser Ala Ala Glu
145             150             155             160 gtg atg atg gat gta tct gat ttg ccg gag agt ttt gat tgg aga gaa    649
Val Met Met Asp Val Ser Asp Leu Pro Glu Ser Phe Asp Trp Arg Glu
                165             170             175 aaa ggt gct gtg acc gaa gtg aag acg cag gga aga tgt gga tcg tgt    697
Lys Gly Ala Val Thr Glu Val Lys Thr Gln Gly Arg Cys Gly Ser Cys
            180             185             190 tgg gct ttt agt aca act gga gct att gaa gga gct aat ttc att gca    745
Trp Ala Phe Ser Thr Thr Gly Ala Ile Glu Gly Ala Asn Phe Ile Ala
    195             200             205 act ggc aag ctt ctc agc cta agt gaa cag cag ctt gtg gat tgt gat    793
Thr Gly Lys Leu Leu Ser Leu Ser Glu Gln Gln Leu Val Asp Cys Asp
210             215             220 cat atg tgt gat tta aaa gaa aaa gat gac tgt gat gat gga tgc tcc    841
His Met Cys Asp Leu Lys Glu Lys Asp Asp Cys Asp Asp Gly Cys Ser
225             230             235             240 gga ggg cta atg aca act gct ttc aac tac ttg ata gag gca gga ggt    889
Gly Gly Leu Met Thr Thr Ala Phe Asn Tyr Leu Ile Glu Ala Gly Gly
                245             250             255 ata gag gag gag gta acc tat ccc tac act ggg aaa cgc gga gaa tgc    937
Ile Glu Glu Glu Val Thr Tyr Pro Tyr Thr Gly Lys Arg Gly Glu Cys
            260             265             270 aaa ttc aat cct gag aaa gtt gcg gtg aaa gtg cgg aat ttc gca aaa    985
Lys Phe Asn Pro Glu Lys Val Ala Val Lys Val Arg Asn Phe Ala Lys
    275             280             285 atc cct gag gat gag agt caa att gct gcc aat gta gtg cat aat ggc   1033
Ile Pro Glu Asp Glu Ser Gln Ile Ala Ala Asn Val Val His Asn Gly
290             295             300 ccg ctt gct att gga ttg aat gcg gta ttc atg caa act tac atc ggg   1081
Pro Leu Ala Ile Gly Leu Asn Ala Val Phe Met Gln Thr Tyr Ile Gly
305             310             315             320 ggt gtg tca tgt cct ctt att tgt gac aaa aag agg atc aac cat ggt   1129
Gly Val Ser Cys Pro Leu Ile Cys Asp Lys Lys Arg Ile Asn His Gly
                325             330             335
```

```
gtt ctt ctt gtg ggc tat ggt tct aga ggc ttc tca atc ctt agg ctt    1177
Val Leu Leu Val Gly Tyr Gly Ser Arg Gly Phe Ser Ile Leu Arg Leu
            340                 345                 350 ggc tac aag cca tac tgg att atc aag aac tca tgg ggg aag cgt tgg    1225
Gly Tyr Lys Pro Tyr Trp Ile Ile Lys Asn Ser Trp Gly Lys Arg Trp
        355                 360                 365 ggc gaa cat ggt tgc tac cgg ctt tgt cga ggg cac aac atg tgt gga    1273
Gly Glu His Gly Cys Tyr Arg Leu Cys Arg Gly His Asn Met Cys Gly
    370                 375                 380 atg agc aca atg gtt tca gct gtg gtg aca cag acc tct tga            1315
Met Ser Thr Met Val Ser Ala Val Val Thr Gln Thr Ser
385                 390                 395 taccaaaaca tctctgctct tcagaggttg tatacaaggt ggtttgctct tggaagatct    1375
tatcatgttt tcgaaatatt taggtttgta taatatgaag ggtagagagt aataagaacc    1435 aaacaaagt tcaggcctgt ttctgatagg aatggaatat gatcggagtc atttgttact    1495
ggatcacaaa aaaaaatcca aaaaaaaaaa aaaaaaaaaa aaaaaaaa                1543

<210> SEQ ID NO 2
<211> LENGTH: 397
<212> TYPE: PRT
<213> ORGANISM: Coffea canephora

<400> SEQUENCE: 2

Met Met Met Thr Ser Gly Gly Leu Met Leu Thr Cys Thr Leu Ala Ile
1               5                   10                  15

Thr Leu Leu Ser Cys Ala Leu Ile Ser Ser Thr Thr Phe Gln His Glu
            20                  25                  30

Ile Gln Tyr Arg Val Gln Asp Pro Leu Met Ile Arg Gln Val Thr Asp
        35                  40                  45

Asn His His Arg His His Pro Gly Arg Ser Ser Ala Asn His Arg
    50                  55                  60

Leu Leu Gly Thr Thr Glu Val His Phe Lys Ser Phe Val Glu Glu
65                  70                  75                  80

Tyr Glu Lys Thr Tyr Ser Thr His Glu Glu Tyr Val His Arg Leu Gly
                85                  90                  95

Ile Phe Ala Lys Asn Leu Ile Lys Ala Ala Glu His Gln Ala Met Asp
            100                 105                 110

Pro Ser Ala Ile His Gly Val Thr Gln Phe Ser Asp Leu Thr Glu Glu
        115                 120                 125

Glu Phe Glu Ala Thr Tyr Met Gly Leu Lys Gly Ala Gly Val Gly
    130                 135                 140

Gly Thr Thr Gln Leu Gly Lys Asp Asp Gly Asp Glu Ser Ala Ala Glu
145                 150                 155                 160

Val Met Met Asp Val Ser Asp Leu Pro Glu Ser Phe Asp Trp Arg Glu
                165                 170                 175

Lys Gly Ala Val Thr Glu Val Lys Thr Gln Gly Arg Cys Gly Ser Cys
            180                 185                 190

Trp Ala Phe Ser Thr Thr Gly Ala Ile Glu Gly Ala Asn Phe Ile Ala
        195                 200                 205

Thr Gly Lys Leu Leu Ser Leu Ser Glu Gln Gln Leu Val Asp Cys Asp
    210                 215                 220

His Met Cys Asp Leu Lys Glu Lys Asp Asp Cys Asp Asp Gly Cys Ser
225                 230                 235                 240

Gly Gly Leu Met Thr Thr Ala Phe Asn Tyr Leu Ile Glu Ala Gly Gly
                245                 250                 255
```

```
Ile Glu Glu Glu Val Thr Tyr Pro Tyr Thr Gly Lys Arg Gly Glu Cys
            260                 265                 270

Lys Phe Asn Pro Glu Lys Val Ala Val Lys Val Arg Asn Phe Ala Lys
                275                 280                 285

Ile Pro Glu Asp Glu Ser Gln Ile Ala Ala Asn Val Val His Asn Gly
            290                 295                 300

Pro Leu Ala Ile Gly Leu Asn Ala Val Phe Met Gln Thr Tyr Ile Gly
305                 310                 315                 320

Gly Val Ser Cys Pro Leu Ile Cys Asp Lys Lys Arg Ile Asn His Gly
                325                 330                 335

Val Leu Leu Val Gly Tyr Gly Ser Arg Gly Phe Ser Ile Leu Arg Leu
            340                 345                 350

Gly Tyr Lys Pro Tyr Trp Ile Ile Lys Asn Ser Trp Gly Lys Arg Trp
            355                 360                 365

Gly Glu His Gly Cys Tyr Arg Leu Cys Arg Gly His Asn Met Cys Gly
            370                 375                 380

Met Ser Thr Met Val Ser Ala Val Val Thr Gln Thr Ser
385                 390                 395

<210> SEQ ID NO 3
<211> LENGTH: 726
<212> TYPE: DNA
<213> ORGANISM: Coffea canephora
<220> FEATURE:
<221> NAME/KEY: mRNA
<222> LOCATION: (1)..(726)
<220> FEATURE:
<221> NAME/KEY: CDS
<222> LOCATION: (79)..(498)

<400> SEQUENCE: 3
ggcgcaacaa acattgaaag aaaatcaaga acccaaaaaa accccacaag aaaaaaagaa          60
aaagaagaag aaaagcca atg gca aaa cca tcg tca tct cta ctc aca ctt         111
                    Met Ala Lys Pro Ser Ser Ser Leu Leu Thr Leu
                      1               5                  10 cct tcc ttt ctt ctg atc ttt ttc att ctt gca cta ttt tcc acc acc         159
Pro Ser Phe Leu Leu Ile Phe Phe Ile Leu Ala Leu Phe Ser Thr Thr
             15                  20                  25 ctc caa gtt aat gcc ttg gga agg aaa gtg gga gca agg gag aag att         207
Leu Gln Val Asn Ala Leu Gly Arg Lys Val Gly Ala Arg Glu Lys Ile
         30                  35                  40 gag gat gtg aag agc aac aaa gaa gtt caa gaa ctt ggg gaa tat tgt         255
Glu Asp Val Lys Ser Asn Lys Glu Val Gln Glu Leu Gly Glu Tyr Cys
     45                  50                  55 gtt tct gag tac aac aag agt ttg cgg aag aag aac aac gaa agt ggt         303
Val Ser Glu Tyr Asn Lys Ser Leu Arg Lys Lys Asn Asn Glu Ser Gly
 60                  65                  70                  75 gct cct ata atc ttc aca tct gtg gtg gag gct gag aag cag gtg gtt         351
Ala Pro Ile Ile Phe Thr Ser Val Val Glu Ala Glu Lys Gln Val Val
                 80                  85                  90 gct ggg atc aaa tat tat ctc aag att aag gcc acc act tct tct ggg         399
Ala Gly Ile Lys Tyr Tyr Leu Lys Ile Lys Ala Thr Thr Ser Ser Gly
             95                 100                 105 gtt ccc aag gtt tac gat gcc att gtg gtg gtt cgg cct tgg gtt cat         447
Val Pro Lys Val Tyr Asp Ala Ile Val Val Val Arg Pro Trp Val His
        110                 115                 120 act aag cca agg cag ttg ctc aac ttc tcc cct tcc cct gcc act aaa         495
Thr Lys Pro Arg Gln Leu Leu Asn Phe Ser Pro Ser Pro Ala Thr Lys
    125                 130                 135 tga agaagaaaat gttgaaaaag ttggaactgt ttgggagatc taatctgatg              548
```

```
attattagta cctttcagtg caaattctct ttgctgttaa gtgttcggtt tttttttttt    608
ccctgtgtct atttatgacc gtggtcatga tgatatggtg tatgatccag taataattaa    668
aatctgttgc ataaaaaaaa aaaaaaaaaa aaaaaaaaaa aaaaaaaaaa aaaaaaa       726

<210> SEQ ID NO 4
<211> LENGTH: 139
<212> TYPE: PRT
<213> ORGANISM: Coffea canephora

<400> SEQUENCE: 4

Met Ala Lys Pro Ser Ser Ser Leu Leu Thr Leu Pro Ser Phe Leu Leu
1               5                   10                  15

Ile Phe Phe Ile Leu Ala Leu Phe Ser Thr Thr Leu Gln Val Asn Ala
            20                  25                  30

Leu Gly Arg Lys Val Gly Ala Arg Glu Lys Ile Glu Asp Val Lys Ser
        35                  40                  45

Asn Lys Glu Val Gln Glu Leu Gly Glu Tyr Cys Val Ser Glu Tyr Asn
    50                  55                  60

Lys Ser Leu Arg Lys Lys Asn Asn Glu Ser Gly Ala Pro Ile Ile Phe
65                  70                  75                  80

Thr Ser Val Val Glu Ala Glu Lys Gln Val Val Ala Gly Ile Lys Tyr
                85                  90                  95

Tyr Leu Lys Ile Lys Ala Thr Thr Ser Ser Gly Val Pro Lys Val Tyr
            100                 105                 110

Asp Ala Ile Val Val Val Arg Pro Trp Val His Thr Lys Pro Arg Gln
        115                 120                 125

Leu Leu Asn Phe Ser Pro Ser Pro Ala Thr Lys
    130                 135

<210> SEQ ID NO 5
<211> LENGTH: 2282
<212> TYPE: DNA
<213> ORGANISM: Coffea canephora
<220> FEATURE:
<221> NAME/KEY: mRNA
<222> LOCATION: (1)..(2282)
<223> OTHER INFORMATION: mRNA
<220> FEATURE:
<221> NAME/KEY: CDS
<222> LOCATION: (439)..(1731)
<223> OTHER INFORMATION: CDS

<400> SEQUENCE: 5
actcactata ctttgcattc tcttcaccat tctccctcaa aactccctcc aacattcttt     60
tccttggttt tttcatctat ccctcctata aaaatcgatt attttgttct tttacctctt    120
aaaaatccat tcttggaatt catttatcca tatacaccat acttgtgcat gtcccttttg    180
gttgttttgc tttgtgata agtaattgtt ggttattgg ttttcatga tggctccgga      240 tctaagaaga aatgggtcgg tagtagcttt agccctgtta gtctctctgg ttgttaatgg    300
tgttattttt gatgtagaag gtaacaataa tgtggttttt gaggtggaac ataaatttaa    360
agggagaagg aatgagaatg gaggaagagg gtcttttga cttcactcaa ggctcatgat     420
tcccaccgcc atggcaga atg ctt gca gcc ctt gac atg cct ttg ggt ggc     471
                    Met Leu Ala Ala Leu Asp Met Pro Leu Gly Gly
                    1               5                   10 aat ggt tcc cct aca gat gca gcg ctc tat ttc act aag ctt tcg att      519
Asn Gly Ser Pro Thr Asp Ala Ala Leu Tyr Phe Thr Lys Leu Ser Ile
         15                  20                  25
```

```
ggg act cct cct cag gat tat tat gtg caa gtg gat aca gga agt gac       567
Gly Thr Pro Pro Gln Asp Tyr Tyr Val Gln Val Asp Thr Gly Ser Asp
        30                  35                  40 att ctc tgg gta aac tgt gct ggt tgt gtc aga tgc ccc aag aaa agc       615
Ile Leu Trp Val Asn Cys Ala Gly Cys Val Arg Cys Pro Lys Lys Ser
45                  50                  55 agt ctt ggt att gac ttg act cta tat gac atg aaa gcc tcc agc acc       663
Ser Leu Gly Ile Asp Leu Thr Leu Tyr Asp Met Lys Ala Ser Ser Thr
60                  65                  70                  75 ggg aga ctt gtt act tgt gat caa gac ttt tgc ttg tct gca ttc aat       711
Gly Arg Leu Val Thr Cys Asp Gln Asp Phe Cys Leu Ser Ala Phe Asn
                80                  85                  90 gcc cca gcc tct gat tgc aag gtt ggt aac ccc tgt gca tat tct gtt       759
Ala Pro Ala Ser Asp Cys Lys Val Gly Asn Pro Cys Ala Tyr Ser Val
            95                  100                 105 act tac gga gac ggg agc tca acc ggc gga tat ttt gtc aga gac tat       807
Thr Tyr Gly Asp Gly Ser Ser Thr Gly Gly Tyr Phe Val Arg Asp Tyr
        110                 115                 120 gca aaa ctt aat caa ctg acg gga aat ctt caa acc ata ccc atg aat       855
Ala Lys Leu Asn Gln Leu Thr Gly Asn Leu Gln Thr Ile Pro Met Asn
125                 130                 135 ggt agt ata gtg ttt ggg tgt tca tct caa caa tct gga gag cta ggg       903
Gly Ser Ile Val Phe Gly Cys Ser Ser Gln Gln Ser Gly Glu Leu Gly
140                 145                 150                 155 tca tct act gaa gca gtt gat ggc ata att ggt ttt gga caa gca aat       951
Ser Ser Thr Glu Ala Val Asp Gly Ile Ile Gly Phe Gly Gln Ala Asn
                160                 165                 170 tca tct att att tca cag ctt gct tca gca gga aag gtt aaa aaa ata       999
Ser Ser Ile Ile Ser Gln Leu Ala Ser Ala Gly Lys Val Lys Lys Ile
            175                 180                 185 ttt tca cat tgc ttg gat ggt atc aat gga gga ggc ata ttt gct att      1047
Phe Ser His Cys Leu Asp Gly Ile Asn Gly Gly Gly Ile Phe Ala Ile
        190                 195                 200 gga caa gta gtg cag cca aaa cta aag aca aca cca ttg gtc cca aat      1095
Gly Gln Val Val Gln Pro Lys Leu Lys Thr Thr Pro Leu Val Pro Asn
205                 210                 215 gag gca cat tat aat gtt gtt ctg aac gca att gag gtg ggt ggc gac      1143
Glu Ala His Tyr Asn Val Val Leu Asn Ala Ile Glu Val Gly Gly Asp
220                 225                 230                 235 gtt cta aac ctt ccc tca gat gta tta gga ggt gga tct gga agt ggt      1191
Val Leu Asn Leu Pro Ser Asp Val Leu Gly Gly Gly Ser Gly Ser Gly
                240                 245                 250 aca ata ata gac agt ggt aca acc ttg gct tat ctt cct gat gat gtc      1239
Thr Ile Ile Asp Ser Gly Thr Thr Leu Ala Tyr Leu Pro Asp Asp Val
            255                 260                 265 tat act cca ctt atg gaa aag att acg gca tcc caa tcc aac ttg aaa      1287
Tyr Thr Pro Leu Met Glu Lys Ile Thr Ala Ser Gln Ser Asn Leu Lys
        270                 275                 280 atc cat att gtt gaa aat cag ttc aag tgc ttt gtc tat agt gga aat      1335
Ile His Ile Val Glu Asn Gln Phe Lys Cys Phe Val Tyr Ser Gly Asn
285                 290                 295 gtt gat gat gga ttt cca gtt gta tct ttc cac ttt gag gat tca ctt      1383
Val Asp Asp Gly Phe Pro Val Val Ser Phe His Phe Glu Asp Ser Leu
300                 305                 310                 315 tct ttg aca gtt tat ccc cat gaa tat ctc ttt gat ctt cat gat gat      1431
Ser Leu Thr Val Tyr Pro His Glu Tyr Leu Phe Asp Leu His Asp Asp
                320                 325                 330 caa tgg tgt att ggt tgg cag aat aag ggt atg cag aca aga gat gga      1479
Gln Trp Cys Ile Gly Trp Gln Asn Lys Gly Met Gln Thr Arg Asp Gly
            335                 340                 345
```

```
agg gaa gta act ctt ttg gga gat ctt gta ctc gca aac aag ctt gtt    1527
Arg Glu Val Thr Leu Leu Gly Asp Leu Val Leu Ala Asn Lys Leu Val
        350                 355                 360 tcg tat gat ctt gaa aat caa acc att gga tgg gct gaa tat aat tgc    1575
Ser Tyr Asp Leu Glu Asn Gln Thr Ile Gly Trp Ala Glu Tyr Asn Cys
        365                 370                 375 tct tcg agc atc aaa ttg aga gac gag aag tca gga aac gtg tat gct    1623
Ser Ser Ser Ile Lys Leu Arg Asp Glu Lys Ser Gly Asn Val Tyr Ala
380                 385                 390                 395 gtg ggc tct cat atc att tct tca gct cgc ggc ctg aat gct gga aag    1671
Val Gly Ser His Ile Ile Ser Ser Ala Arg Gly Leu Asn Ala Gly Lys
                400                 405                 410 gct cta agg ttc cta ttg tta atc atc aca tca ttg ttg cat gca ctt    1719
Ala Leu Arg Phe Leu Leu Leu Ile Ile Thr Ser Leu Leu His Ala Leu
                415                 420                 425 ttg atc cca tga acatttaaaa tcatactagc tgagaaggag gcattatgat        1771
Leu Ile Pro
        430 agcgtaccat ggtactcata gtgatcaggc atcttgctga ttctttggac cattataatt  1831 tctcatgtgt ttaaagtgaa agtcagttcg tcgagacatc ttgtgactcc ataatcttct  1891 tgatcaagct gaactctact cacaaaacca tagctaattc ttttgatctc aaaagagaaa  1951 taggctctgc aaaaggattt cggaggttga tgttgaacat tcttcttatt tggatgttat  2011 tgatacccca gatgattaag gaaagcctat aggaaacaga tggtgggaag gagtatacat  2071 tctttctgac tctttggaac ttcctagcgt atacacatat ttcacacgga atgtatctta  2131 taattcatct gttctttctg tttattgtca acttgtttca aatgattgga gtagctgcaa  2191 taatcaactc ggatggtggt tcatgcttaa ggctcgtctt gcctcattgt taagacgtga  2251 aaaaaaaaaa aaaaaaaaaa aaaaaaaaaa a                                 2282

<210> SEQ ID NO 6
<211> LENGTH: 430
<212> TYPE: PRT
<213> ORGANISM: Coffea canephora

<400> SEQUENCE: 6

Met Leu Ala Ala Leu Asp Met Pro Leu Gly Gly Asn Gly Ser Pro Thr
1               5                   10                  15

Asp Ala Ala Leu Tyr Phe Thr Lys Leu Ser Ile Gly Thr Pro Pro Gln
                20                  25                  30

Asp Tyr Tyr Val Gln Val Asp Thr Gly Ser Asp Ile Leu Trp Val Asn
            35                  40                  45

Cys Ala Gly Cys Val Arg Cys Pro Lys Lys Ser Ser Leu Gly Ile Asp
        50                  55                  60

Leu Thr Leu Tyr Asp Met Lys Ala Ser Ser Thr Gly Arg Leu Val Thr
65                  70                  75                  80

Cys Asp Gln Asp Phe Cys Leu Ser Ala Phe Asn Ala Pro Ala Ser Asp
                85                  90                  95

Cys Lys Val Gly Asn Pro Cys Ala Tyr Ser Val Thr Tyr Gly Asp Gly
                100                 105                 110

Ser Ser Thr Gly Gly Tyr Phe Val Arg Asp Tyr Ala Lys Leu Asn Gln
            115                 120                 125

Leu Thr Gly Asn Leu Gln Thr Ile Pro Met Asn Gly Ser Ile Val Phe
130                 135                 140

Gly Cys Ser Ser Gln Gln Ser Gly Glu Leu Gly Ser Thr Glu Ala
145                 150                 155                 160
```

```
Val Asp Gly Ile Ile Gly Phe Gly Gln Ala Asn Ser Ser Ile Ile Ser
                165                 170                 175

Gln Leu Ala Ser Ala Gly Lys Val Lys Lys Ile Phe Ser His Cys Leu
            180                 185                 190

Asp Gly Ile Asn Gly Gly Ile Phe Ala Ile Gly Gln Val Val Gln
        195                 200                 205

Pro Lys Leu Lys Thr Thr Pro Leu Val Pro Asn Glu Ala His Tyr Asn
    210                 215                 220

Val Val Leu Asn Ala Ile Glu Val Gly Gly Asp Val Leu Asn Leu Pro
225                 230                 235                 240

Ser Asp Val Leu Gly Gly Ser Gly Ser Gly Thr Ile Ile Asp Ser
                245                 250                 255

Gly Thr Thr Leu Ala Tyr Leu Pro Asp Asp Val Tyr Thr Pro Leu Met
            260                 265                 270

Glu Lys Ile Thr Ala Ser Gln Ser Asn Leu Lys Ile His Ile Val Glu
        275                 280                 285

Asn Gln Phe Lys Cys Phe Val Tyr Ser Gly Asn Val Asp Asp Gly Phe
    290                 295                 300

Pro Val Val Ser Phe His Phe Glu Asp Ser Leu Ser Leu Thr Val Tyr
305                 310                 315                 320

Pro His Glu Tyr Leu Phe Asp Leu His Asp Asp Gln Trp Cys Ile Gly
                325                 330                 335

Trp Gln Asn Lys Gly Met Gln Thr Arg Asp Gly Arg Glu Val Thr Leu
            340                 345                 350

Leu Gly Asp Leu Val Leu Ala Asn Lys Leu Val Ser Tyr Asp Leu Glu
        355                 360                 365

Asn Gln Thr Ile Gly Trp Ala Glu Tyr Asn Cys Ser Ser Ser Ile Lys
    370                 375                 380

Leu Arg Asp Glu Lys Ser Gly Asn Val Tyr Ala Val Gly Ser His Ile
385                 390                 395                 400

Ile Ser Ser Ala Arg Gly Leu Asn Ala Gly Lys Ala Leu Arg Phe Leu
                405                 410                 415

Leu Leu Ile Ile Thr Ser Leu Leu His Ala Leu Leu Ile Pro
            420                 425                 430

<210> SEQ ID NO 7
<211> LENGTH: 1819
<212> TYPE: DNA
<213> ORGANISM: Coffea canephora
<220> FEATURE:
<221> NAME/KEY: mRNA
<222> LOCATION: (1)..(1732)
<220> FEATURE:
<221> NAME/KEY: CDS
<222> LOCATION: (79)..(1602)

<400> SEQUENCE: 7
cttactgact ctcgtatatt attcaatcta tcttttgagt tttgcaagag cccatcaagc     60
atcaaggcat aaccaacg atg gag agg agg tac ctt tgg gca gca ttt gta    111
                   Met Glu Arg Arg Tyr Leu Trp Ala Ala Phe Val
                    1               5                  10 tta ggg gcg att gtg tgt tct cta ttt cct ctt cct tct gaa gga tta   159
Leu Gly Ala Ile Val Cys Ser Leu Phe Pro Leu Pro Ser Glu Gly Leu
            15                  20                  25 aag cga att agc ctg aaa aaa aaa ccc tta gat att caa agc ata aga   207
Lys Arg Ile Ser Leu Lys Lys Lys Pro Leu Asp Ile Gln Ser Ile Arg
        30                  35                  40 gct gcc aaa tta gct cat ctg gag agc aca cat ggc gct ggt agg aaa   255
```

```
                                                           -continued

Ala Ala Lys Leu Ala His Leu Glu Ser Thr His Gly Ala Gly Arg Lys
     45              50              55 gag atg gac aac aat tta ggc agt tcc aat gag gac ata ttg cct tta    303
Glu Met Asp Asn Asn Leu Gly Ser Ser Asn Glu Asp Ile Leu Pro Leu
 60              65              70              75 aag aat tac ctg gat gcc cag tac tat gga gag att gga att ggt act    351
Lys Asn Tyr Leu Asp Ala Gln Tyr Tyr Gly Glu Ile Gly Ile Gly Thr
             80              85              90 cca cct cag aag ttc aca gtt ata ttt gat aca ggc agt tcc aac ctc    399
Pro Pro Gln Lys Phe Thr Val Ile Phe Asp Thr Gly Ser Ser Asn Leu
         95             100             105 tgg gtg cca tcg gca aaa tgt tac ttc tct att gcc tgc tgg ctc cac    447
Trp Val Pro Ser Ala Lys Cys Tyr Phe Ser Ile Ala Cys Trp Leu His
        110             115             120 tcc aag tac aag gca aag aag tca agt act tat aca gcc ata ggg aaa    495
Ser Lys Tyr Lys Ala Lys Lys Ser Ser Thr Tyr Thr Ala Ile Gly Lys
    125             130             135 tct tgt tca att cgt tat ggt tct gga tca att tct gga ttc tcc agt    543
Ser Cys Ser Ile Arg Tyr Gly Ser Gly Ser Ile Ser Gly Phe Ser Ser
140             145             150             155 cag gat aac gtt gaa gtt ggt gat ctt gtt gtc aaa gat caa gtt ttt    591
Gln Asp Asn Val Glu Val Gly Asp Leu Val Val Lys Asp Gln Val Phe
                160             165             170 att gaa gct tca cga gaa gga agt ctt aca ttt gta att gcc aag ttt    639
Ile Glu Ala Ser Arg Glu Gly Ser Leu Thr Phe Val Ile Ala Lys Phe
            175             180             185 gac ggg ata ctt ggc ctt gga ttc cag gag atc gct gtt gat aac atg    687
Asp Gly Ile Leu Gly Leu Gly Phe Gln Glu Ile Ala Val Asp Asn Met
        190             195             200 gtg ccg gtc tgg tat aat atg gtg gac caa ggt ctc gtg gat gag caa    735
Val Pro Val Trp Tyr Asn Met Val Asp Gln Gly Leu Val Asp Glu Gln
    205             210             215 gta ttc tct ttc tgg ctt aac cgc gac cca aat gct gaa gac gga ggt    783
Val Phe Ser Phe Trp Leu Asn Arg Asp Pro Asn Ala Glu Asp Gly Gly
220             225             230             235 gag ctg gtc ttt ggt ggt gta gat aca aat cac ttc aag gga aag cat    831
Glu Leu Val Phe Gly Gly Val Asp Thr Asn His Phe Lys Gly Lys His
                240             245             250 aca tat gtt cct gta act cag aag gga tac tgg caa ttt aaa atg gga    879
Thr Tyr Val Pro Val Thr Gln Lys Gly Tyr Trp Gln Phe Lys Met Gly
            255             260             265 gat ttt ctc att ggg aac gtc tca aca ggc ttt tgt gaa gga ggt tgt    927
Asp Phe Leu Ile Gly Asn Val Ser Thr Gly Phe Cys Glu Gly Gly Cys
        270             275             280 gct gct att gtg gac tct gga aca tcg ttg ctc gct ggt cca act act    975
Ala Ala Ile Val Asp Ser Gly Thr Ser Leu Leu Ala Gly Pro Thr Thr
    285             290             295 gtt gtg act caa att aat cat gcc att gga gct gaa gga gta gtt agc    1023
Val Val Thr Gln Ile Asn His Ala Ile Gly Ala Glu Gly Val Val Ser
300             305             310             315 act gaa tgt aaa gaa att gtt tca cag tat ggt gaa ctg att tgg gat    1071
Thr Glu Cys Lys Glu Ile Val Ser Gln Tyr Gly Glu Leu Ile Trp Asp
                320             325             330 ctc ctc gta tca ggg gta cta ccc gac aga gtt tgt aaa caa gct ggt    1119
Leu Leu Val Ser Gly Val Leu Pro Asp Arg Val Cys Lys Gln Ala Gly
            335             340             345 tta tgt ccc ctt cgt ggt gct cag cat gag aat gct tat atc aag tca    1167
Leu Cys Pro Leu Arg Gly Ala Gln His Glu Asn Ala Tyr Ile Lys Ser
        350             355             360 gtc gtc gac gag gag aac aag gag gaa gct tct gtt ggt gaa tcc ccg    1215
```

```
       Val Val Asp Glu Glu Asn Lys Glu Glu Ala Ser Val Gly Glu Ser Pro
           365                 370                 375 atg tgt act gct tgt gaa atg gct gtt gtt tgg atg caa aac cag ctg           1263
Met Cys Thr Ala Cys Glu Met Ala Val Val Trp Met Gln Asn Gln Leu
380                 385                 390                 395 aaa cag cag gga act aag gag aaa gtg ctt gca tat gtg aat cag ctt           1311
Lys Gln Gln Gly Thr Lys Glu Lys Val Leu Ala Tyr Val Asn Gln Leu
                400                 405                 410 tgt gaa agc ata cca agt ccc atg gga gaa tcc atc att gac tgc aac           1359
Cys Glu Ser Ile Pro Ser Pro Met Gly Glu Ser Ile Ile Asp Cys Asn
            415                 420                 425 agt tta tcc acc ctg cca aat gtt tca ttc acc atc gga ggg aaa agt           1407
Ser Leu Ser Thr Leu Pro Asn Val Ser Phe Thr Ile Gly Gly Lys Ser
        430                 435                 440 ttt gag ctg acc ctt aag gag tat gtt ctt cga act gga gaa ggc ttt           1455
Phe Glu Leu Thr Leu Lys Glu Tyr Val Leu Arg Thr Gly Glu Gly Phe
    445                 450                 455 gct gaa gtc tgc atc agt gga ttc atg gct atg gat gtg ccg ccg cct           1503
Ala Glu Val Cys Ile Ser Gly Phe Met Ala Met Asp Val Pro Pro Pro
460                 465                 470                 475 cgt ggt ccc atc tgg gtt ctg gga gat gtg ttc atg gga gtg tac cac           1551
Arg Gly Pro Ile Trp Val Leu Gly Asp Val Phe Met Gly Val Tyr His
                480                 485                 490 acc gtg ttt gat tat ggt aat ctc cgg atg ggt ttc gca aga gct gct           1599
Thr Val Phe Asp Tyr Gly Asn Leu Arg Met Gly Phe Ala Arg Ala Ala
            495                 500                 505 tag acaagactgt ttatttcgtc tactgtttga cggtcctaag agaagctatg              1652
aagacatgta gtagcttgta aattaggatt taattatgct tggctggttt atgggtggtg        1712 ctttaatat tatatgtaat gtaagcagat atgttacctt gttttagagt ttcaaggaaa         1772
ctgcaatatt tacttccggt aaaaaaaaaa aaaaaaaaaa aaaaaa                       1819

<210> SEQ ID NO 8
<211> LENGTH: 507
<212> TYPE: PRT
<213> ORGANISM: Coffea canephora

<400> SEQUENCE: 8

Met Glu Arg Arg Tyr Leu Trp Ala Ala Phe Val Leu Gly Ala Ile Val
1               5                   10                  15

Cys Ser Leu Phe Pro Leu Pro Ser Glu Gly Leu Lys Arg Ile Ser Leu
            20                  25                  30

Lys Lys Lys Pro Leu Asp Ile Gln Ser Ile Arg Ala Ala Lys Leu Ala
        35                  40                  45

His Leu Glu Ser Thr His Gly Ala Gly Arg Lys Glu Met Asp Asn Asn
    50                  55                  60

Leu Gly Ser Ser Asn Glu Asp Ile Leu Pro Lys Asn Tyr Leu Asp
65                  70                  75                  80

Ala Gln Tyr Tyr Gly Glu Ile Gly Ile Gly Thr Pro Pro Gln Lys Phe
                85                  90                  95

Thr Val Ile Phe Asp Thr Gly Ser Ser Asn Leu Trp Val Pro Ser Ala
            100                 105                 110

Lys Cys Tyr Phe Ser Ile Ala Cys Trp Leu His Ser Lys Tyr Lys Ala
        115                 120                 125

Lys Lys Ser Ser Thr Tyr Thr Ala Ile Gly Lys Ser Cys Ser Ile Arg
    130                 135                 140

Tyr Gly Ser Gly Ser Ile Ser Gly Phe Ser Ser Gln Asp Asn Val Glu
145                 150                 155                 160
```

Val Gly Asp Leu Val Val Lys Asp Gln Val Phe Ile Glu Ala Ser Arg
            165                 170                 175

Glu Gly Ser Leu Thr Phe Val Ile Ala Lys Phe Asp Gly Ile Leu Gly
            180                 185                 190

Leu Gly Phe Gln Glu Ile Ala Val Asp Asn Met Val Pro Val Trp Tyr
            195                 200                 205

Asn Met Val Asp Gln Gly Leu Val Asp Glu Gln Val Phe Ser Phe Trp
210                 215                 220

Leu Asn Arg Asp Pro Asn Ala Glu Asp Gly Gly Glu Leu Val Phe Gly
225                 230                 235                 240

Gly Val Asp Thr Asn His Phe Lys Gly Lys His Thr Tyr Val Pro Val
            245                 250                 255

Thr Gln Lys Gly Tyr Trp Gln Phe Lys Met Gly Asp Phe Leu Ile Gly
            260                 265                 270

Asn Val Ser Thr Gly Phe Cys Glu Gly Cys Ala Ala Ile Val Asp
            275                 280                 285

Ser Gly Thr Ser Leu Leu Ala Gly Pro Thr Thr Val Thr Gln Ile
290                 295                 300

Asn His Ala Ile Gly Ala Glu Gly Val Val Ser Thr Glu Cys Lys Glu
305                 310                 315                 320

Ile Val Ser Gln Tyr Gly Glu Leu Ile Trp Asp Leu Leu Val Ser Gly
            325                 330                 335

Val Leu Pro Asp Arg Val Cys Lys Gln Ala Gly Leu Cys Pro Leu Arg
            340                 345                 350

Gly Ala Gln His Glu Asn Ala Tyr Ile Lys Ser Val Val Asp Glu Glu
            355                 360                 365

Asn Lys Glu Glu Ala Ser Val Gly Glu Ser Pro Met Cys Thr Ala Cys
370                 375                 380

Glu Met Ala Val Val Trp Met Gln Asn Gln Leu Lys Gln Gln Gly Thr
385                 390                 395                 400

Lys Glu Lys Val Leu Ala Tyr Val Asn Gln Leu Cys Glu Ser Ile Pro
            405                 410                 415

Ser Pro Met Gly Glu Ser Ile Ile Asp Cys Asn Ser Leu Ser Thr Leu
            420                 425                 430

Pro Asn Val Ser Phe Thr Ile Gly Gly Lys Ser Phe Glu Leu Thr Leu
            435                 440                 445

Lys Glu Tyr Val Leu Arg Thr Gly Glu Gly Phe Ala Glu Val Cys Ile
            450                 455                 460

Ser Gly Phe Met Ala Met Asp Val Pro Pro Arg Gly Pro Ile Trp
465                 470                 475                 480

Val Leu Gly Asp Val Phe Met Gly Val Tyr His Thr Val Phe Asp Tyr
            485                 490                 495

Gly Asn Leu Arg Met Gly Phe Ala Arg Ala Ala
            500                 505

<210> SEQ ID NO 9
<211> LENGTH: 726
<212> TYPE: DNA
<213> ORGANISM: Coffea canephora

<400> SEQUENCE: 9
ggactttttc tcgcactaag ttcacagaaa aagataagaa ggctctgtat ttgggaattt    60
tgttgaattt tcagtcgatt ttttgtttct taagaagga atggcaaaag ttggtgggat    120
cagtgaatct aagggcaatg agaacagcct tgaaattgag agcctggcta agtttgctgt    180

```
ggatgattac aacaagaaac agaatgccct tttggaattt cagaaggtga tcaacagtaa    240
agagcaggtt gttgctggta ccgtgtacta tctgaccatt gaggtgaaag atgggaatga    300
gaagaagctt tatgaggcca agtttgggt gaagccatgg ttgaacttca aggaggttca     360
agaattcaag cctgctgctg gtgatactag tgcctaaatt tgcttcttaa caatgcgcta    420
ttgcctattt gcctagtaga aataaagcta acgcgtaaat gtctttcagt tggaaagatt    480
ggagtttcaa acatgcttag tttgtatatg ctataactcg taatattaac atgttagtaa    540
catgttatct tatgttggat agatgttaag accaacataa tcttcgctga tgttcggttc    600
gatgtgatct gatcctgtgg tttttatacc actctggctt gagtatcatt acccttagtc    660
cctttatgtg gctcttattg ttgaaataaa agtcattttt tctcttaaaa aaaaaaaaa     720 aaaaaa                                                               726

<210> SEQ ID NO 10
<211> LENGTH: 98
<212> TYPE: PRT
<213> ORGANISM: Coffea canephora

<400> SEQUENCE: 10

Met Ala Lys Val Gly Gly Ile Ser Glu Ser Lys Gly Asn Glu Asn Ser
1               5                   10                  15

Leu Glu Ile Glu Ser Leu Ala Lys Phe Ala Val Asp Asp Tyr Asn Lys
            20                  25                  30

Lys Gln Asn Ala Leu Leu Glu Phe Gln Lys Val Ile Asn Ser Lys Glu
        35                  40                  45

Gln Val Val Ala Gly Thr Val Tyr Tyr Leu Thr Ile Glu Val Lys Asp
    50                  55                  60

Gly Asn Glu Lys Lys Leu Tyr Glu Ala Lys Val Trp Val Lys Pro Trp
65                  70                  75                  80

Leu Asn Phe Lys Glu Val Gln Glu Phe Lys Pro Ala Ala Gly Asp Thr
                85                  90                  95

Ser Ala

<210> SEQ ID NO 11
<211> LENGTH: 688
<212> TYPE: DNA
<213> ORGANISM: Coffea canephora

<400> SEQUENCE: 11
ggaaataacc ccccactag attgaaaccg cccgttcaaa atccatccat ccatcagccc     60
caacaccaat aaccgacgct gcaagaatgg cttctgcctt tccccatctc tcctactca    120 ccaccctggc agctatctgt cttttctccg acgtcccttc cgcggctttg ggtggtcgcc    180
ccaaagatgc cttagtcggc ggttggagta aggctgaccc caaggaccca gaggtgctag    240
agaacggaaa atttgccata gatgagcaca caaggaggc cggtaccaag ttggagttta    300
aaactgtggt ggaggcgcag aagcaagtgg tggccggcac aaattacaag attgtgataa    360
aggcattgga tggcactgct tcaaatctgt acgaggccat tgtttgggtc aagccctggc    420
tcaaattcaa gaagcttact tccttcagga aacttccctg atcagattta aggggatgta    480
ataagcatgt gcatttcttg cttaaaactg tggcatgaga ggtgtatgta taatcatctg    540
tatttcttgc ttaaaactgt ggtatgacta tgagagatgt ttgaagtgta ctgtactaca    600
agagctttca tacatatgca agagttgaag cacttgtttg cttctgataa taataataat    660
acatcgtttt aaaaaaaaaa aaaaaaa                                       688
```

<210> SEQ ID NO 12
<211> LENGTH: 124
<212> TYPE: PRT
<213> ORGANISM: Coffea canephora

<400> SEQUENCE: 12

```
Met Ala Ser Ala Phe Pro His Leu Leu Leu Thr Thr Leu Ala Ala
1               5                   10                  15

Ile Cys Leu Phe Ser Asp Val Pro Ser Ala Ala Leu Gly Gly Arg Pro
                20                  25                  30

Lys Asp Ala Leu Val Gly Gly Trp Ser Lys Ala Asp Pro Lys Asp Pro
            35                  40                  45

Glu Val Leu Glu Asn Gly Lys Phe Ala Ile Asp Glu His Asn Lys Glu
        50                  55                  60

Ala Gly Thr Lys Leu Glu Phe Lys Thr Val Val Glu Ala Gln Lys Gln
65                  70                  75                  80

Val Val Ala Gly Thr Asn Tyr Lys Ile Val Ile Lys Ala Leu Asp Gly
                85                  90                  95

Thr Ala Ser Asn Leu Tyr Glu Ala Ile Val Trp Val Lys Pro Trp Leu
                100                 105                 110

Lys Phe Lys Lys Leu Thr Ser Phe Arg Lys Leu Pro
            115                 120
```

<210> SEQ ID NO 13
<211> LENGTH: 697
<212> TYPE: DNA
<213> ORGANISM: Coffea canephora

<400> SEQUENCE: 13

```
gttttcgata gtcacaagca attgcaaaaa tctacttcgt acttataagc tagctagttc      60
ctcaaggaaa aaatggctac ggtcgcagcc aaatctgcta ctgccgctat tggtgctgga     120
cagaaaaaca tggtgggtgg tggtctaagc tctactgttc ctcctcgatc gtcaaccgtc     180
aacccgaaag accctcacgt gattcagatc gcacaatttg cagttgcaaa ctacaacgcg     240
aaggccggga ccactgtggt ttggctgaat gtggaatatg gcttctggtg gattgacgat     300
gacacttact acatgcttgc cattaaaact caggatctta cgggcacaca ttgcgacgta     360
gcattggttc gtgaaatatc ggagagcaat ggtacttata gcctcaaatg gtacaatcat     420
aacaataagt gaccacgcac tactcttgat cagctgagga tcaatgactt taattatata     480
tagtgtttat ggtgtggctt tcagtttatg catggatgat gtactgctgt catgcatacg     540
tctccctacg gtggtactag tacattgaag gtgcagttgt accgataaaa atgcaccatt     600
aaataaaaaa aaatcaccgt ttatgtttga gtttgtattc ctgtatgata aaggtgcagt     660
taaggcacca ttaaatatga tggcttcgtc actttct                              697
```

<210> SEQ ID NO 14
<211> LENGTH: 119
<212> TYPE: PRT
<213> ORGANISM: Coffea canephora

<400> SEQUENCE: 14

```
Met Ala Thr Val Ala Ala Lys Ser Ala Thr Ala Ile Gly Ala Gly
1               5                   10                  15

Gln Lys Asn Met Val Gly Gly Gly Leu Ser Ser Thr Val Pro Pro Arg
                20                  25                  30

Ser Ser Thr Val Asn Pro Lys Asp Pro His Val Ile Gln Ile Ala Gln
```

```
                    35                  40                  45
Phe Ala Val Ala Asn Tyr Asn Ala Lys Ala Gly Thr Thr Val Val Trp
 50                  55                  60

Leu Asn Val Glu Tyr Gly Phe Trp Trp Ile Asp Asp Thr Tyr Tyr
 65                  70                  75                  80

Met Leu Ala Ile Lys Thr Gln Asp Leu Thr Gly Thr His Cys Asp Val
                 85                  90                  95

Ala Leu Val Arg Glu Ile Ser Glu Ser Asn Gly Thr Tyr Ser Leu Lys
            100                 105                 110

Trp Tyr Asn His Asn Asn Lys
        115

<210> SEQ ID NO 15
<211> LENGTH: 1367
<212> TYPE: DNA
<213> ORGANISM: Coffea canephora

<400> SEQUENCE: 15
ggcttacatc ttaaatcctg attttatag attcgccttt cgtgaagttc aatcttcgca      60
gtcgctcact aacatttggt agacatactt cgattatgaa atggggaag gctttccttt     120 ttgccgttgt attggctgtg atcttagtgg cggctatgag catggagatc acagaaagag    180
atttggcttc tgaggaaagc ttgtgggact tgtacgaaag atggaggagc catcatactg    240
tttctcgaga cctttctgag aaacgaaagc gctttaatgt tttcaaggca aatgtccatc    300
acattcacaa ggtgaaccag aaggacaagc cttacaagct gaaactcaac agtttcgctg    360
atatgaccaa ccacgagttc agggaattct acagttctaa ggtgaaacat taccggatgc    420
tccacggcag tcgtgctaat actggattta tgcatgggaa gactgaaagt ttgccagcct    480
ccgttgattg gagaaagcaa ggagccgtga ctggcgtcaa gaatcaaggc aaatgtggta    540
gctgttgggc attttcaact gtggttggag tcgaggggaat caacaaaatc aaaacaggcc    600 aattagttc tctgtccgag caagaacttg ttgactgtga acggacaat gaaggatgca     660 acggaggact catggaaaat gcatacgagt ttattaagaa agtgggga ataacaactg      720 agaggctata tccctacaag gcaagagatg gcagctgtga ttcgtcaaag atgaatgccc    780
ctgctgtgac tattgatggg catgaaatgg tacccgcaaa cgatgagaat gccttgatga    840
aagctgttgc taaccagcct gtatcagtag ctatagatgc gtctggctct gacatgcaat    900
tttattcaga gggtgtatac gctggagact cgtgtggcaa tgagcttgat catggcgtgg    960
cggtcgtcgg ctacgggact gctcttgacg gtactaaata ctggatagtg aagaactcat   1020
ggggaacagg atggggagaa cagggctata tcaggatgca acgtggtgtt gatgctgctg   1080
aaggcggagt ttgtgggata gcaatggagg cctcctatcc acttaaattg tcctcccaca   1140
atccaaaacc atccccacct aaggacgacc tctagattga tcctcttata tatacata    1200 tatatatata tttcagtaga ttcattgaat tttagttaca gactacgcgc ttctgaagac   1260
ttagatcatc tctaggcata gatttatgta atcctgctcc tgtgatggtt tgaataaaca   1320
ataagtagta ctaataaaaa aaaaaaaaa aaaaaaaaa aaaaaa                    1367

<210> SEQ ID NO 16
<211> LENGTH: 359
<212> TYPE: PRT
<213> ORGANISM: Coffea canephora

<400> SEQUENCE: 16

Met Lys Met Gly Lys Ala Phe Leu Phe Ala Val Val Leu Ala Val Ile
```

|  |  |  |  |  |  |  |  |  |  |  |  |  |  |  |
|---|---|---|---|---|---|---|---|---|---|---|---|---|---|---|
| 1 |  |  |  | 5 |  |  |  |  | 10 |  |  |  |  | 15 |

Leu Val Ala Ala Met Ser Met Glu Ile Thr Glu Arg Asp Leu Ala Ser
             20                  25                  30

Glu Glu Ser Leu Trp Asp Leu Tyr Glu Arg Trp Arg Ser His His Thr
         35                  40                  45

Val Ser Arg Asp Leu Ser Glu Lys Arg Lys Phe Asn Val Phe Lys
 50                  55                  60

Ala Asn Val His His Ile His Lys Val Asn Gln Lys Asp Lys Pro Tyr
 65                  70                  75                  80

Lys Leu Lys Leu Asn Ser Phe Ala Asp Met Thr Asn His Glu Phe Arg
                 85                  90                  95

Glu Phe Tyr Ser Ser Lys Val Lys His Tyr Arg Met Leu His Gly Ser
             100                 105                 110

Arg Ala Asn Thr Gly Phe Met His Gly Lys Thr Glu Ser Leu Pro Ala
             115                 120                 125

Ser Val Asp Trp Arg Lys Gln Gly Ala Val Thr Gly Val Lys Asn Gln
         130                 135                 140

Gly Lys Cys Gly Ser Cys Trp Ala Phe Ser Thr Val Val Gly Val Glu
145                 150                 155                 160

Gly Ile Asn Lys Ile Lys Thr Gly Gln Leu Val Ser Leu Ser Glu Gln
                 165                 170                 175

Glu Leu Val Asp Cys Glu Thr Asp Asn Glu Gly Cys Asn Gly Gly Leu
             180                 185                 190

Met Glu Asn Ala Tyr Glu Phe Ile Lys Lys Ser Gly Gly Ile Thr Thr
         195                 200                 205

Glu Arg Leu Tyr Pro Tyr Lys Ala Arg Asp Gly Ser Cys Asp Ser Ser
     210                 215                 220

Lys Met Asn Ala Pro Ala Val Thr Ile Asp Gly His Glu Met Val Pro
225                 230                 235                 240

Ala Asn Asp Glu Asn Ala Leu Met Lys Ala Val Ala Asn Gln Pro Val
             245                 250                 255

Ser Val Ala Ile Asp Ala Ser Gly Ser Asp Met Gln Phe Tyr Ser Glu
         260                 265                 270

Gly Val Tyr Ala Gly Asp Ser Cys Gly Asn Glu Leu Asp His Gly Val
     275                 280                 285

Ala Val Val Gly Tyr Gly Thr Ala Leu Asp Gly Thr Lys Tyr Trp Ile
     290                 295                 300

Val Lys Asn Ser Trp Gly Thr Gly Trp Gly Glu Gln Gly Tyr Ile Arg
305                 310                 315                 320

Met Gln Arg Gly Val Asp Ala Ala Glu Gly Gly Val Cys Gly Ile Ala
             325                 330                 335

Met Glu Ala Ser Tyr Pro Leu Lys Leu Ser Ser His Asn Pro Lys Pro
             340                 345                 350

Ser Pro Pro Lys Asp Asp Leu
             355

<210> SEQ ID NO 17
<211> LENGTH: 4
<212> TYPE: PRT
<213> ORGANISM: Artificial Sequence
<220> FEATURE:
<223> OTHER INFORMATION: Synthesized peptide

<400> SEQUENCE: 17

Lys Asp Glu Leu
1

<210> SEQ ID NO 18
<211> LENGTH: 24
<212> TYPE: DNA
<213> ORGANISM: Artificial Sequence
<220> FEATURE:
<223> OTHER INFORMATION: Synthesized primer: A4-43-upper

<400> SEQUENCE: 18
accgaggagg agtttgaggc tacg					24

<210> SEQ ID NO 19
<211> LENGTH: 23
<212> TYPE: DNA
<213> ORGANISM: Artificial Sequence
<220> FEATURE:
<223> OTHER INFORMATION: Synthesized primer: A4-43-lower

<400> SEQUENCE: 19
acgcttcccc catgagttct tga					23

<210> SEQ ID NO 20
<211> LENGTH: 25
<212> TYPE: DNA
<213> ORGANISM: Artificial Sequence
<220> FEATURE:
<223> OTHER INFORMATION: Synthesized primer: CcCPI-1 (up)

<400> SEQUENCE: 20
aggaaagtgg gagcaaggga gaaga					25

<210> SEQ ID NO 21
<211> LENGTH: 25
<212> TYPE: DNA
<213> ORGANISM: Artificial Sequence
<220> FEATURE:
<223> OTHER INFORMATION: Synthesized primer: CcCPI-1 (low)

<400> SEQUENCE: 21
tagtatgaac ccaaggccga accac					25

<210> SEQ ID NO 22
<211> LENGTH: 20
<212> TYPE: DNA
<213> ORGANISM: Artificial Sequence
<220> FEATURE:
<223> OTHER INFORMATION: Synthesized primer: CcCPI-2 (up)

<400> SEQUENCE: 22
gtgaagccat ggttgaactt					20

<210> SEQ ID NO 23
<211> LENGTH: 20
<212> TYPE: DNA
<213> ORGANISM: Artificial Sequence
<220> FEATURE:
<223> OTHER INFORMATION: Synthesized primer: CcCPI-2 (low)

<400> SEQUENCE: 23
gtaatgatac tcaagccaga					20

<210> SEQ ID NO 24
<211> LENGTH: 19
<212> TYPE: DNA
<213> ORGANISM: Artificial Sequence
<220> FEATURE:
<223> OTHER INFORMATION: Synthesized primer: CcCPI-4 (up)

```
<400> SEQUENCE: 24
ctacggtcgc agccaaatc                                                  19

<210> SEQ ID NO 25
<211> LENGTH: 21
<212> TYPE: DNA
<213> ORGANISM: Artificial Sequence
<220> FEATURE:
<223> OTHER INFORMATION: Synthesized primer: CcCPI-4 (low)

<400> SEQUENCE: 25
acaactgcac cttcaatgta c                                               21

<210> SEQ ID NO 26
<211> LENGTH: 21
<212> TYPE: DNA
<213> ORGANISM: Artificial Sequence
<220> FEATURE:
<223> OTHER INFORMATION: Synthesized primer: 2S protein, contig 8A

<400> SEQUENCE: 26
agcaactgca gcaaggtgga g                                               21

<210> SEQ ID NO 27
<211> LENGTH: 22
<212> TYPE: DNA
<213> ORGANISM: Artificial Sequence
<220> FEATURE:
<223> OTHER INFORMATION: Synthesized primer: contig 8B

<400> SEQUENCE: 27
cgatttggca ctgctgtggt tc                                              22

<210> SEQ ID NO 28
<211> LENGTH: 18
<212> TYPE: DNA
<213> ORGANISM: Artificial Sequence
<220> FEATURE:
<223> OTHER INFORMATION: Synthesized primer: 2S protein contig 15A

<400> SEQUENCE: 28
gcccgtgctc ctgaacca                                                   18

<210> SEQ ID NO 29
<211> LENGTH: 20
<212> TYPE: DNA
<213> ORGANISM: Artificial Sequence
<220> FEATURE:
<223> OTHER INFORMATION: Synthesized primer: contig 15B

<400> SEQUENCE: 29
gtatggttgc ggtggctgaa                                                 20

<210> SEQ ID NO 30
<211> LENGTH: 17
<212> TYPE: DNA
<213> ORGANISM: Artificial Sequence
<220> FEATURE:
<223> OTHER INFORMATION: Synthesized primer: Oleosin 15.5 contig 30A

<400> SEQUENCE: 30
accccgcttt tcgttat                                                    17

<210> SEQ ID NO 31
<211> LENGTH: 21
```

-continued

```
<212> TYPE: DNA
<213> ORGANISM: Artificial Sequence
<220> FEATURE:
<223> OTHER INFORMATION: Synthesized primer: contig 30B

<400> SEQUENCE: 31
tctggctaca tcttgagttc t                                              21

<210> SEQ ID NO 32
<211> LENGTH: 19
<212> TYPE: DNA
<213> ORGANISM: Artificial Sequence
<220> FEATURE:
<223> OTHER INFORMATION: Synthesized primer: 11S protein contig 37A

<400> SEQUENCE: 32
gtttccagac cgccatcag                                                 19

<210> SEQ ID NO 33
<211> LENGTH: 22
<212> TYPE: DNA
<213> ORGANISM: Artificial Sequence
<220> FEATURE:
<223> OTHER INFORMATION: Synthesized primer: contig 37B

<400> SEQUENCE: 33
atatccatcc tcttccaaca cc                                             22

<210> SEQ ID NO 34
<211> LENGTH: 28
<212> TYPE: DNA
<213> ORGANISM: Artificial Sequence
<220> FEATURE:
<223> OTHER INFORMATION: Synthesized primer: rAP2

<400> SEQUENCE: 34
catataatat taaaagcacc acccataa                                       28

<210> SEQ ID NO 35
<211> LENGTH: 28
<212> TYPE: DNA
<213> ORGANISM: Artificial Sequence
<220> FEATURE:
<223> OTHER INFORMATION: Synthesized primer: rAP1

<400> SEQUENCE: 35
tggagtcaca agatgtctcg acgaactg                                       28

<210> SEQ ID NO 36
<211> LENGTH: 24
<212> TYPE: DNA
<213> ORGANISM: Artificial Sequence
<220> FEATURE:
<223> OTHER INFORMATION: Synthesized primer: CcCP-1 up

<400> SEQUENCE: 36
accgaggagg agtttgaggc tacg                                           24

<210> SEQ ID NO 37
<211> LENGTH: 23
<212> TYPE: DNA
<213> ORGANISM: Artificial Sequence
<220> FEATURE:
<223> OTHER INFORMATION: Synthesized primer: CcCP-1 low

<400> SEQUENCE: 37
acgcttcccc catgagttct tga                                            23
```

```
<210> SEQ ID NO 38
<211> LENGTH: 21
<212> TYPE: DNA
<213> ORGANISM: Artificial Sequence
<220> FEATURE:
<223> OTHER INFORMATION: Synthesized primer: A5-1750-upper

<400> SEQUENCE: 38
tggcgaagaa gcagaggcag a                                             21

<210> SEQ ID NO 39
<211> LENGTH: 20
<212> TYPE: DNA
<213> ORGANISM: Artificial Sequence
<220> FEATURE:
<223> OTHER INFORMATION: Synthesized primer: A5-1750-lower

<400> SEQUENCE: 39
ttgaggggga gggtaaaaag                                               20

<210> SEQ ID NO 40
<211> LENGTH: 23
<212> TYPE: DNA
<213> ORGANISM: Artificial Sequence
<220> FEATURE:
<223> OTHER INFORMATION: Synthesized primer: CP-4KDDL61

<400> SEQUENCE: 40
gaagaactca tggggaacag gat                                           23

<210> SEQ ID NO 41
<211> LENGTH: 24
<212> TYPE: DNA
<213> ORGANISM: Artificial Sequence
<220> FEATURE:
<223> OTHER INFORMATION: Synthesized primer: CP-4KDDL345

<400> SEQUENCE: 41
ttattcaaac catcacagga gcag                                          24

<210> SEQ ID NO 42
<211> LENGTH: 4
<212> TYPE: PRT
<213> ORGANISM: Artificial Sequence
<220> FEATURE:
<223> OTHER INFORMATION: Synthesized peptide

<400> SEQUENCE: 42

Lys Asp Asp Leu
1

<210> SEQ ID NO 43
<211> LENGTH: 4
<212> TYPE: PRT
<213> ORGANISM: Artificial Sequence
<220> FEATURE:
<223> OTHER INFORMATION: Synthesized peptide

<400> SEQUENCE: 43

Ser Asp Glu Leu
1

<210> SEQ ID NO 44
<211> LENGTH: 4
<212> TYPE: PRT
<213> ORGANISM: Artificial Sequence
```

```
<220> FEATURE:
<223> OTHER INFORMATION: Synthesized peptide

<400> SEQUENCE: 44

Lys Asp Glu Ile
1

<210> SEQ ID NO 45
<211> LENGTH: 4
<212> TYPE: PRT
<213> ORGANISM: Artificial Sequence
<220> FEATURE:
<223> OTHER INFORMATION: Synthesized peptide

<400> SEQUENCE: 45

Lys Asp Glu Val
1

<210> SEQ ID NO 46
<211> LENGTH: 348
<212> TYPE: PRT
<213> ORGANISM: Coffea canephora

<400> SEQUENCE: 46

Met Met Met Thr Ser Gly Gly Leu Met Leu Thr Cys Thr Leu Ala Ile
1               5                   10                  15

Thr Leu Leu Ser Cys Ala Leu Ile Ser Ser Thr Thr Phe Gln His Glu
            20                  25                  30

Ile Gln Tyr Arg Val Gln Asp Pro Leu Met Ile Arg Gln Val Thr Asp
        35                  40                  45

Asn His His Arg His His Pro Gly Arg Ser Ser Ala Asn His Arg
    50                  55                  60

Leu Leu Gly Thr Thr Thr Glu Val His Phe Lys Ser Phe Val Glu Glu
65                  70                  75                  80

Tyr Glu Lys Thr Tyr Ser Thr His Glu Glu Tyr Val His Arg Leu Gly
                85                  90                  95

Ile Phe Ala Lys Asn Leu Ile Lys Ala Ala Glu His Gln Ala Met Asp
            100                 105                 110

Pro Ser Ala Ile His Gly Val Thr Gln Phe Ser Asp Leu Thr Glu Glu
        115                 120                 125

Glu Phe Glu Ala Thr Tyr Met Gly Leu Lys Gly Gly Ala Gly Val Gly
    130                 135                 140

Gly Thr Thr Gln Leu Gly Lys Asp Asp Gly Asp Glu Ser Ala Ala Glu
145                 150                 155                 160

Val Met Met Asp Val Ser Asp Leu Pro Glu Ser Phe Asp Trp Arg Glu
                165                 170                 175

Lys Gly Ala Val Thr Glu Val Lys Thr Gln Gly Arg Cys Gly Ser Cys
            180                 185                 190

Trp Ala Phe Ser Thr Thr Gly Ala Ile Glu Gly Ala Asn Phe Ile Ala
        195                 200                 205

Thr Gly Lys Leu Leu Ser Leu Ser Glu Gln Gln Leu Val Asp Cys Asp
    210                 215                 220

His Met Cys Asp Leu Lys Glu Lys Asp Asp Cys Asp Gly Cys Ser
225                 230                 235                 240

Gly Gly Leu Met Thr Thr Ala Phe Asn Tyr Leu Ile Glu Ala Gly Gly
                245                 250                 255

Ile Glu Glu Glu Val Thr Tyr Pro Tyr Thr Gly Lys Arg Gly Glu Cys
            260                 265                 270
```

```
Lys Phe Asn Pro Glu Ile Cys Asp Lys Lys Arg Ile Asn His Gly Val
            275                 280                 285

Leu Leu Val Gly Tyr Gly Ser Arg Gly Phe Ser Ile Leu Arg Leu Gly
        290                 295                 300

Tyr Lys Pro Tyr Trp Ile Ile Lys Asn Ser Trp Gly Lys Arg Trp Gly
305                 310                 315                 320

Glu His Gly Cys Tyr Arg Leu Cys Arg Gly His Asn Met Cys Gly Met
                325                 330                 335

Ser Thr Met Val Ser Ala Val Val Thr Gln Thr Ser
            340                 345

<210> SEQ ID NO 47
<211> LENGTH: 367
<212> TYPE: PRT
<213> ORGANISM: Arabidopsis thaliana

<400> SEQUENCE: 47

Met Val Ala Lys Ala Leu Ala Gln Leu Ile Thr Cys Ile Ile Leu Phe
1               5                   10                  15

Cys His Val Val Ala Ser Val Glu Asp Leu Thr Ile Arg Gln Val Thr
            20                  25                  30

Ala Asp Asn Arg Arg Ile Arg Pro Asn Leu Leu Gly Thr His Thr Glu
        35                  40                  45

Ser Lys Phe Arg Leu Phe Met Ser Asp Tyr Gly Lys Asn Tyr Ser Thr
    50                  55                  60

Arg Glu Glu Tyr Ile His Arg Leu Gly Ile Phe Ala Lys Asn Val Leu
65                  70                  75                  80

Lys Ala Ala Glu His Gln Met Met Asp Pro Ser Ala Val His Gly Val
                85                  90                  95

Thr Gln Phe Ser Asp Leu Thr Glu Glu Phe Lys Arg Met Tyr Thr
            100                 105                 110

Gly Val Ala Asp Val Gly Gly Ser Arg Gly Gly Thr Val Gly Ala Glu
        115                 120                 125

Ala Pro Met Val Glu Val Asp Gly Leu Pro Glu Asp Phe Asp Trp Arg
130                 135                 140

Glu Lys Gly Gly Val Thr Glu Val Lys Asn Gln Gly Ala Cys Gly Ser
145                 150                 155                 160

Cys Trp Ala Phe Ser Thr Thr Gly Ala Ala Glu Gly Ala His Phe Val
                165                 170                 175

Ser Thr Gly Lys Leu Leu Ser Leu Ser Glu Gln Gln Leu Val Asp Cys
            180                 185                 190

Asp Gln Ala Cys Asp Pro Lys Asp Lys Ala Cys Asp Asn Gly Cys
        195                 200                 205

Gly Gly Gly Leu Met Thr Asn Ala Tyr Glu Tyr Leu Met Glu Ala Gly
210                 215                 220

Gly Leu Glu Glu Glu Arg Ser Tyr Pro Tyr Thr Gly Lys Arg Gly His
225                 230                 235                 240

Cys Lys Phe Asp Pro Glu Lys Val Ala Val Arg Val Leu Asn Phe Thr
                245                 250                 255

Thr Ile Pro Leu Asp Glu Asn Gln Ile Ala Ala Asn Leu Val Arg His
            260                 265                 270

Gly Pro Leu Ala Val Gly Leu Asn Ala Val Phe Met Gln Thr Tyr Ile
        275                 280                 285

Gly Gly Val Ser Cys Pro Leu Ile Cys Ser Lys Arg Asn Val Asn His
290                 295                 300
```

Gly Val Leu Leu Val Gly Tyr Gly Ser Lys Gly Phe Ser Ile Leu Arg
305                 310                 315                 320

Leu Ser Asn Lys Pro Tyr Trp Ile Ile Lys Asn Ser Trp Gly Lys Lys
            325                 330                 335

Trp Gly Glu Asn Gly Tyr Tyr Lys Leu Cys Arg Gly His Asp Ile Cys
                340                 345                 350

Gly Ile Asn Ser Met Val Ser Ala Val Ala Thr Gln Val Ser Ser
            355                 360                 365

<210> SEQ ID NO 48
<211> LENGTH: 380
<212> TYPE: PRT
<213> ORGANISM: Glycine max

<400> SEQUENCE: 48

Met Glu Ala Lys Arg Gly His Ala Leu Met Cys Leu Ala Arg Val Ser
1               5                   10                  15

Leu Phe Leu Cys Ala Leu Thr Leu Ser Ala Ala His Gly Ser Thr Thr
                20                  25                  30

Val Gln Asp Ile Ala Arg Lys Leu Lys Leu Gly Asp Asn Glu Leu Leu
            35                  40                  45

Arg Thr Glu Lys Lys Phe Lys Val Phe Met Glu Asn Tyr Gly Arg Ser
50                  55                  60

Tyr Ser Thr Glu Glu Glu Tyr Leu Arg Arg Leu Gly Ile Phe Ala Gln
65                  70                  75                  80

Asn Met Val Arg Ala Ala Glu His Gln Ala Leu Asp Pro Thr Ala Val
                85                  90                  95

His Gly Val Thr Gln Phe Ser Asp Leu Thr Glu Asp Glu Phe Glu Lys
            100                 105                 110

Leu Tyr Thr Gly Val Asn Gly Gly Phe Pro Ser Ser Asn Asn Ala Ala
        115                 120                 125

Gly Gly Ile Ala Pro Pro Leu Glu Val Asp Gly Leu Pro Glu Asn Phe
    130                 135                 140

Asp Trp Arg Glu Lys Gly Ala Val Thr Glu Val Lys Leu Gln Gly Arg
145                 150                 155                 160

Cys Gly Ser Cys Trp Ala Phe Ser Thr Thr Gly Ser Ile Glu Gly Ala
                165                 170                 175

Asn Phe Leu Ala Thr Gly Lys Leu Val Ser Leu Ser Glu Gln Gln Leu
            180                 185                 190

Leu Asp Cys Asp Asn Lys Cys Asp Ile Thr Glu Lys Thr Ser Cys Asp
        195                 200                 205

Asn Gly Cys Asn Gly Gly Leu Met Thr Asn Ala Tyr Asn Tyr Leu Leu
    210                 215                 220

Glu Ser Gly Gly Leu Glu Glu Ser Ser Tyr Pro Tyr Thr Gly Glu
225                 230                 235                 240

Arg Gly Glu Cys Lys Phe Asp Pro Glu Lys Ile Ala Val Lys Ile Thr
                245                 250                 255

Asn Phe Thr Asn Ile Pro Ala Asp Glu Asn Gln Ile Ala Ala Tyr Leu
            260                 265                 270

Val Lys Asn Gly Pro Leu Ala Met Gly Val Asn Ala Ile Phe Met Gln
        275                 280                 285

Thr Tyr Ile Gly Gly Val Ser Cys Pro Leu Ile Cys Ser Lys Lys Arg
    290                 295                 300

Leu Asn His Gly Val Leu Leu Val Gly Tyr Gly Ala Lys Gly Phe Ser
305                 310                 315                 320

```
Ile Leu Arg Leu Gly Asn Lys Pro Tyr Trp Ile Ile Lys Asn Ser Trp
            325                 330                 335

Gly Glu Lys Trp Gly Glu Asp Gly Tyr Tyr Lys Leu Cys Arg Gly His
            340                 345                 350

Gly Met Cys Gly Ile Asn Thr Met Val Ser Ala Ala Met Val Pro Gln
            355                 360                 365

Pro Gln Thr Thr Pro Thr Lys Asn Tyr Ala Ser Tyr
            370                 375                 380

<210> SEQ ID NO 49
<211> LENGTH: 379
<212> TYPE: PRT
<213> ORGANISM: Vicia sativa

<400> SEQUENCE: 49

Met Val Ala Lys Gln Asn Pro Pro Leu Thr Arg Tyr Ala Arg Val Ala
1               5                   10                  15

Ile Phe Leu Cys Ala Leu Thr Leu Ser Ser Ser Leu His His Glu Thr
            20                  25                  30

Leu Ile Gln Asp Val Ala Arg Lys Leu Glu Leu Lys Asp Asn Asp Leu
        35                  40                  45

Leu Thr Thr Glu Lys Lys Phe Lys Leu Phe Met Lys Asp Tyr Ser Lys
    50                  55                  60

Lys Tyr Ser Thr Thr Glu Glu Tyr Leu Leu Arg Leu Gly Ile Phe Ala
65                  70                  75                  80

Lys Asn Met Val Lys Ala Ala Glu His Gln Ala Leu Asp Pro Thr Ala
                85                  90                  95

Ile His Gly Val Thr Gln Phe Ser Asp Leu Ser Glu Glu Phe Glu
            100                 105                 110

Arg Phe Tyr Thr Gly Phe Lys Gly Gly Phe Pro Ser Ser Asn Ala Ala
            115                 120                 125

Gly Gly Val Ala Pro Pro Leu Asp Val Lys Gly Phe Pro Glu Asn Phe
        130                 135                 140

Asp Trp Arg Glu Lys Gly Ala Val Thr Gly Ile Lys Thr Gln Gly Lys
145                 150                 155                 160

Cys Gly Ser Cys Trp Ala Phe Thr Thr Thr Gly Ser Ile Glu Gly Ala
                165                 170                 175

Asn Phe Leu Ala Thr Gly Lys Leu Val Ser Leu Ser Glu Gln Gln Leu
            180                 185                 190

Val Asp Cys Asp Asn Lys Cys Asp Ile Thr Lys Thr Ser Cys Asp Asn
        195                 200                 205

Gly Cys Asn Gly Gly Leu Met Thr Thr Ala Tyr Asp Tyr Leu Met Glu
    210                 215                 220

Ala Gly Gly Leu Glu Glu Glu Thr Ser Tyr Pro Tyr Thr Gly Ala Gln
225                 230                 235                 240

Gly Glu Cys Lys Phe Asp Pro Asn Lys Val Ala Val Arg Val Ser Asn
                245                 250                 255

Phe Thr Asn Ile Pro Ala Asp Glu Asn Gln Ile Ala Ala Tyr Leu Val
            260                 265                 270

Asn His Gly Pro Leu Ala Ile Ala Val Asn Ala Val Phe Met Gln Thr
        275                 280                 285

Tyr Val Gly Gly Val Ser Cys Pro Leu Ile Cys Ser Lys Arg Arg Leu
    290                 295                 300

Asn His Gly Val Leu Leu Val Gly Tyr Asn Ala Glu Gly Phe Ser Ile
305                 310                 315                 320
```

Leu Arg Leu Arg Lys Lys Pro Tyr Trp Thr Ile Lys Asn Ser Trp Gly
            325                 330                 335

Glu Gln Trp Gly Glu Lys Gly Tyr Tyr Lys Leu Cys Arg Gly His Gly
            340                 345                 350

Met Cys Gly Met Asn Thr Met Val Ser Ala Ala Met Val Thr Gln Ile
            355                 360                 365

Gln Pro Ala Asp Asn Lys Ser Tyr Ala Ser Tyr
            370                 375

<210> SEQ ID NO 50
<211> LENGTH: 375
<212> TYPE: PRT
<213> ORGANISM: Glycine max

<400> SEQUENCE: 50

Met Glu Ala Lys Arg Gly His Ala Leu Met Cys Leu Ala Arg Val Ser
1               5                   10                  15

Leu Phe Leu Cys Ala Leu Thr Leu Ser Ala Ala His Gly Ser Thr Thr
            20                  25                  30

Val Gln Asp Ile Ala Arg Lys Leu Lys Leu Gly Asp Asn Phe Thr Glu
            35                  40                  45

Leu Leu Arg Thr Glu Lys Lys Phe Lys Val Phe Met Glu Asn Tyr Gly
50                  55                  60

Arg Ser Tyr Ser Thr Glu Glu Tyr Leu Arg Leu Gly Ile Phe
65                  70                  75                  80

Ala Gln Asn Met Val Arg Ala Ala Glu His Gln Ala Leu Asp Pro Thr
            85                  90                  95

Ala Val His Gly Val Thr Gln Phe Ser Leu Phe Thr Pro Val Ser Asn
            100                 105                 110

Asn Ala Ala Gly Gly Ile Ala Pro Pro Leu Glu Val Asp Gly Leu Pro
            115                 120                 125

Glu Asn Phe Asp Trp Arg Glu Lys Gly Ala Val Thr Glu Val Lys Leu
            130                 135                 140

Gln Gly Arg Cys Gly Ser Cys Trp Ala Phe Ser Thr Thr Gly Ser Ile
145                 150                 155                 160

Glu Gly Ala Asn Phe Leu Ala Phe Thr Thr Gly Lys Leu Val Ser Leu
            165                 170                 175

Ser Asp Gln Gln Leu Leu Asp Cys Asp Asn Lys Cys Asp Ile Thr Glu
            180                 185                 190

Lys Thr Ser Cys Asp Asn Gly Cys Asn Gly Gly Leu Met Thr Asn Ala
            195                 200                 205

Tyr Asn Tyr Leu Leu Glu Ser Gly Gly Leu Glu Glu Glu Ser Ser Tyr
            210                 215                 220

Pro Tyr Thr Gly Phe Thr Glu Arg Gly Glu Cys Lys Phe Asp Pro Glu
225                 230                 235                 240

Lys Ile Ala Val Lys Ile Thr Asn Phe Thr Asn Ile Pro Ala Asp Glu
            245                 250                 255

Asn Gln Ile Ala Ala Tyr Leu Val Lys Asn Gly Pro Leu Ala Met Gly
            260                 265                 270

Val Asn Ala Ile Phe Met Gln Thr Tyr Ile Gly Gly Val Ser Cys Pro
            275                 280                 285

Leu Phe Thr Ile Cys Ser Lys Lys Arg Leu Asn His Gly Val Leu Leu
            290                 295                 300

Val Gly Tyr Gly Ala Lys Gly Phe Ser Ile Leu Arg Leu Gly Asn Lys
305                 310                 315                 320

```
Pro Tyr Trp Ile Ile Lys Asn Ser Trp Gly Glu Lys Trp Gly Glu Asp
            325                 330                 335

Gly Tyr Tyr Lys Leu Cys Arg Gly His Gly Met Cys Gly Ile Phe Thr
            340                 345                 350

Asn Thr Met Val Ser Ala Ala Met Val Pro Gln Pro Gln Thr Thr Pro
            355                 360                 365

Thr Lys Asn Tyr Ala Ser Tyr
        370                 375

<210> SEQ ID NO 51
<211> LENGTH: 377
<212> TYPE: PRT
<213> ORGANISM: Phaseolus vulgaris

<400> SEQUENCE: 51

Met Val Ala Lys Arg Gly His Ala Leu Thr Cys Phe Ala Arg Ile Ser
1               5                   10                  15

Leu Val Leu Phe Ala Leu Thr Leu Ser Ser Ala Arg Gln Thr Thr Val
            20                  25                  30

His Asp Ile Ala Lys Lys Leu Lys Leu Gln Asp Asn Gln Leu Leu Arg
        35                  40                  45

Thr Glu Lys Lys Phe Asn Val Phe Met Glu Asn Tyr Gly Lys Lys Tyr
    50                  55                  60

Ser Thr Arg Glu Glu Tyr Leu Gln Arg Leu Glu Ile Phe Ala Gly Asn
65                  70                  75                  80

Met Leu Arg Ala Pro Glu Asn Gln Ala Leu Asp Pro Thr Ala Ile His
                85                  90                  95

Gly Val Thr Gln Phe Ser Asp Leu Thr Glu Asp Glu Phe Gln Arg His
            100                 105                 110

Tyr Thr Gly Val Asn Gly Gly Phe Pro Trp Asn Asn Gly Val Arg Asp
        115                 120                 125

Val Ala Pro Pro Leu Lys Val Asp Gly Leu Pro Glu Asp Phe Asp Trp
    130                 135                 140

Arg Glu Lys Gly Ala Val Thr Glu Val Lys Met Gln Gly Lys Cys Gly
145                 150                 155                 160

Ser Cys Trp Ala Phe Ser Thr Thr Gly Ser Ile Glu Gly Ala Asn Phe
                165                 170                 175

Ile Ala Thr Gly Lys Leu Leu Asn Leu Ser Glu Gln Gln Leu Val Asp
            180                 185                 190

Cys Asp Ser Gln Cys Asp Ile Thr Glu Ser Thr Thr Cys Asp Asn Gly
        195                 200                 205

Cys Met Gly Gly Leu Met Thr Asn Ala Tyr Lys Tyr Leu Leu Gln Ser
    210                 215                 220

Gly Gly Leu Glu Glu Glu Ser Ser Tyr Pro Tyr Thr Gly Ala Lys Gly
225                 230                 235                 240

Glu Cys Lys Phe Asp Pro Gly Lys Val Ala Val Arg Ile Thr Asn Phe
                245                 250                 255

Thr Asn Ile Pro Val Asp Glu Asn Gln Ile Ala Ala Tyr Leu Val Lys
            260                 265                 270

His Gly Pro Leu Ala Val Gly Leu Asn Ala Ile Phe Met Gln Thr Tyr
        275                 280                 285

Ile Gly Gly Val Ser Cys Pro Leu Ile Cys Ser Lys Lys Trp Leu Asn
    290                 295                 300

His Gly Val Leu Leu Val Gly Tyr Arg Ala Lys Gly Phe Ser Ile Leu
305                 310                 315                 320
```

```
Arg Leu Gly Asn Lys Pro Tyr Trp Ile Ile Lys Asn Ser Trp Gly Lys
                325                 330                 335

Arg Trp Gly Val Asp Gly Tyr Tyr Leu Cys Arg Gly His Gly Met
            340                 345                 350

Cys Gly Met Asn Thr Met Val Ser Thr Ala Met Val Thr Gln Thr Gln
        355                 360                 365

Thr Ala Ser His Asn Tyr Ala Ser Tyr
        370                 375

<210> SEQ ID NO 52
<211> LENGTH: 363
<212> TYPE: PRT
<213> ORGANISM: Solanum melongea

<400> SEQUENCE: 52

Met Asp Arg Leu Phe Leu Leu Ser Leu Leu Ala Phe Ala Leu Phe Ser
1               5                   10                  15

Ser Ala Ile Ala Phe Ser Asp Asp Pro Leu Ile Arg Gln Val Val
            20                  25                  30

Ser Glu Thr Asp Asp Asn His Met Leu Asn Ala Glu His His Phe Ser
        35                  40                  45

Leu Phe Lys Ser Lys Tyr Gly Lys Ile Tyr Ala Ser Gln Glu Glu His
    50                  55                  60

Asp His Arg Leu Lys Val Phe Lys Ala Asn Leu Arg Arg Ala Arg Arg
65                  70                  75                  80

His Gln Leu Leu Asp Pro Thr Ala Glu His Gly Ile Thr Gln Phe Ser
                85                  90                  95

Asp Leu Thr Pro Ser Glu Phe Arg Arg Thr Tyr Leu Gly Leu His Lys
            100                 105                 110

Pro Arg Pro Lys Leu Asn Ala Gln Lys Ala Pro Ile Leu Pro Thr Ser
        115                 120                 125

Asp Leu Pro Glu Asp Phe Asp Trp Arg Glu Lys Gly Ala Val Thr Gly
    130                 135                 140

Val Lys Asn Gln Gly Ser Cys Gly Ser Cys Trp Ser Phe Ser Thr Thr
145                 150                 155                 160

Gly Ala Val Glu Gly Ala His Phe Leu Ala Thr Gly Glu Leu Val Ser
                165                 170                 175

Leu Ser Glu Gln Gln Leu Val Asp Cys Asp His Glu Cys Asp Ala Glu
            180                 185                 190

Glu Lys Ser Glu Cys Asp Ala Gly Cys Asn Gly Gly Leu Met Thr Thr
        195                 200                 205

Ala Phe Glu Tyr Thr Leu Lys Ala Gly Gly Leu Gln Arg Glu Lys Asp
    210                 215                 220

Tyr Pro Tyr Thr Gly Arg Asp Gly Lys Cys His Phe Asp Lys Ser Lys
225                 230                 235                 240

Ile Ala Ala Ser Val Ala Asn Phe Ser Val Ile Gly Leu Asp Glu Asp
                245                 250                 255

Gln Ile Ala Ala Asn Leu Val Lys His Gly Pro Leu Ala Val Gly Ile
            260                 265                 270

Asn Ala Ala Trp Met Gln Thr Tyr Met Arg Gly Val Ser Cys Pro Leu
        275                 280                 285

Ile Cys Phe Lys Arg Gln Asp His Gly Val Leu Leu Val Gly Tyr Gly
    290                 295                 300

Ser Ala Gly Phe Ala Pro Ile Arg Leu Lys Glu Lys Pro Tyr Trp Ile
305                 310                 315                 320
```

```
Ile Lys Asn Ser Trp Gly Glu Asn Trp Gly His Gly Tyr Tyr Lys
            325                 330                 335

Ile Cys Arg Gly His Asn Ile Cys Gly Val Asp Ala Met Val Ser Thr
            340                 345                 350

Val Thr Ala Thr His Thr Asn Pro Asn Leu
            355                 360

<210> SEQ ID NO 53
<211> LENGTH: 365
<212> TYPE: PRT
<213> ORGANISM: Nicotiana tabacum

<400> SEQUENCE: 53

Met Asp Arg Leu Phe Leu Leu Ser Leu Pro Arg Phe Ala Leu Phe Ser
1               5                   10                  15

Ser Ala Ile Ala Phe Pro Asp Glu Asp Pro Leu Ile Arg Gln Val Val
            20                  25                  30

Ser Glu Thr Glu Thr Asp Asp Ser His Leu Leu Asn Ala Glu His His
            35                  40                  45

Phe Ser Leu Phe Lys Ser Lys Phe Gly Lys Ile Tyr Ala Ser Glu Glu
50                  55                  60

Glu His Asp His Arg Phe Lys Val Phe Lys Ala Asn Leu Arg Arg Ala
65                  70                  75                  80

Arg Leu Asn Gln Leu Leu Asp Pro Ser Ala Glu His Gly Ile Thr Lys
                85                  90                  95

Phe Ser Asp Leu Thr Pro Ser Glu Phe Arg Arg Thr Tyr Leu Gly Leu
            100                 105                 110

His Lys Pro Lys Pro Lys Val Asn Ala Glu Lys Ala Pro Ile Leu Pro
            115                 120                 125

Thr Ser Asp Leu Pro Ala Asp Tyr Asp Trp Arg Asp His Gly Ala Val
            130                 135                 140

Thr Gly Val Lys Asn Gln Gly Ser Cys Gly Ser Cys Trp Ser Phe Ser
145                 150                 155                 160

Thr Thr Gly Ala Val Glu Gly Ala His Phe Leu Ala Thr Gly Glu Leu
            165                 170                 175

Val Ser Leu Ser Glu Gln Gln Leu Val Asp Cys Asp His Glu Cys Asp
            180                 185                 190

Ser Glu Gln Gln Asp Ser Cys Asp Ala Gly Cys Gly Gly Leu Met
            195                 200                 205

Thr Thr Ala Phe Glu Tyr Thr Leu Lys Ala Gly Gly Leu Gln Leu Glu
            210                 215                 220

Lys Asp Tyr Pro Tyr Thr Gly Lys Asp Gly Lys Cys His Phe Asp Lys
225                 230                 235                 240

Ser Lys Ile Ala Ala Ala Val Thr Asn Phe Ser Val Ile Gly Leu Asp
            245                 250                 255

Glu Asp Gln Ile Ala Ala Asn Leu Val Lys His Gly Pro Leu Ala Val
            260                 265                 270

Gly Ile Asn Ala Ala Trp Met Gln Thr Tyr Val Gly Gly Val Ser Cys
            275                 280                 285

Pro Leu Ile Cys Phe Lys Arg Gln Asp His Gly Val Leu Leu Val Gly
            290                 295                 300

Tyr Gly Ser His Gly Phe Ala Pro Ile Arg Leu Lys Glu Lys Ala Tyr
305                 310                 315                 320

Trp Ile Ile Lys Asn Ser Trp Gly Glu Asn Trp Gly His Gly Tyr
            325                 330                 335
```

```
Tyr Lys Ile Cys Arg Gly His Asn Ile Cys Gly Val Asp Ala Met Val
            340                 345                 350

Ser Thr Val Thr Ala Ala His Thr Thr Asn Pro Asn Leu
            355                 360                 365

<210> SEQ ID NO 54
<211> LENGTH: 361
<212> TYPE: PRT
<213> ORGANISM: Lycopersicon esculentum

<400> SEQUENCE: 54

Arg Leu Phe Leu Leu Ser Phe Leu Ala Phe Ala Leu Phe Ser Ser Ala
1               5                   10                  15

Ile Ala Phe Ser Asp Asp Pro Leu Ile Arg Gln Val Val Ser Gly
            20                  25                  30

Asn Asp Asp Asn His Met Leu Asn Ala Glu His His Phe Ser Leu Phe
            35                  40                  45

Lys Ala Lys Phe Gly Lys Ile Tyr Ala Ser Gln Glu Glu His Asp His
50                  55                  60

Arg Leu Lys Val Phe Lys Ala Asn Leu His Arg Ala Lys Arg His Gln
65                  70                  75                  80

Leu Leu Asp Pro Ser Ala Glu His Gly Ile Thr Gln Phe Ser Asp Leu
                85                  90                  95

Thr Pro Ser Glu Phe Arg Arg Thr Tyr Leu Gly Leu Asn Lys Pro Arg
            100                 105                 110

Pro Asn Leu Asn Ala Glu Lys Ala Pro Ile Leu Pro Thr Lys Asp Leu
            115                 120                 125

Pro Ser Asp Phe Asp Trp Arg Glu Lys Gly Ala Val Thr Asp Val Lys
            130                 135                 140

Asn Gln Gly Ser Cys Gly Ser Cys Trp Ser Phe Ser Thr Thr Gly Ala
145                 150                 155                 160

Val Glu Gly Ala His Phe Leu Ala Thr Gly Glu Leu Val Ser Leu Ser
                165                 170                 175

Glu Gln Gln Leu Val Asp Cys Asp His Glu Cys Asp Pro Val Glu Lys
            180                 185                 190

Asn Asp Cys Asp Ala Gly Cys Asn Gly Gly Leu Met Thr Thr Ala Phe
            195                 200                 205

Glu Tyr Thr Leu Lys Ala Gly Gly Leu Gln Leu Glu Lys Asp Tyr Pro
            210                 215                 220

Tyr Thr Gly Arg Asn Gly Lys Cys His Phe Asp Lys Ser Arg Ile Ala
225                 230                 235                 240

Ala Ser Val Ser Asn Phe Ser Val Val Gly Leu Asp Glu Asp Gln Ile
                245                 250                 255

Ala Ala Asn Leu Leu Lys His Gly Pro Leu Ala Val Gly Ile Asn Ala
            260                 265                 270

Ala Trp Met Gln Thr Tyr Val Arg Gly Val Ser Cys Pro Leu Ile Cys
            275                 280                 285

Phe Lys Arg Gln Asp His Gly Val Leu Leu Val Gly Tyr Gly Ser Glu
            290                 295                 300

Gly Phe Ala Pro Ile Arg Leu Lys Asn Lys Pro Tyr Trp Ile Ile Lys
305                 310                 315                 320

Asn Ser Trp Gly Lys Thr Trp Gly Glu His Gly Tyr Tyr Lys Ile Cys
                325                 330                 335

Arg Gly His His Ile Cys Gly Val Asp Ala Met Val Ser Thr Val Thr
            340                 345                 350
```

```
Ala Thr His Thr Thr Asn Pro Asn Leu
        355                 360

<210> SEQ ID NO 55
<211> LENGTH: 363
<212> TYPE: PRT
<213> ORGANISM: Vicia faba

<400> SEQUENCE: 55

Met Asp Arg Arg Phe Ile Phe Ala Ile Val Leu Phe Ala Ala Val Ala
1               5                   10                  15

Thr Ser Ser Thr Asp Asn Thr Asn Thr Asp Asp Phe Ile Ile Arg Gln
            20                  25                  30

Val Val Asp Asn Glu Glu Asp His Leu Leu Asn Ala Glu His His Phe
        35                  40                  45

Thr Ser Phe Lys Ser Lys Phe Ser Lys Ser Tyr Ser Thr Lys Glu Glu
    50                  55                  60

His Asp Tyr Arg Phe Gly Val Phe Lys Ser Asn Leu Ile Lys Ala Lys
65                  70                  75                  80

Leu His Gln Lys Leu Asp Pro Thr Ala Glu His Gly Ile Thr Lys Phe
                85                  90                  95

Ser Asp Leu Thr Ala Ser Glu Phe Arg Arg Gln Phe Leu Gly Leu Lys
            100                 105                 110

Lys Arg Leu Arg Leu Pro Ala His Ala Gln Lys Ala Pro Ile Leu Pro
        115                 120                 125

Thr Thr Asn Leu Pro Glu Asp Phe Asp Trp Arg Glu Lys Gly Ala Val
    130                 135                 140

Thr Pro Val Lys Asp Gln Gly Ser Cys Gly Ser Cys Trp Ala Phe Ser
145                 150                 155                 160

Thr Thr Gly Ala Leu Glu Gly Ala His Tyr Leu Ala Thr Gly Lys Leu
                165                 170                 175

Val Ser Leu Ser Glu Gln Gln Leu Val Asp Cys Asp His Val Cys Asp
            180                 185                 190

Pro Glu Gln Ala Gly Ser Cys Asp Ser Gly Cys Asn Gly Gly Leu Met
        195                 200                 205

Asn Asn Ala Phe Glu Tyr Leu Leu Gln Ser Gly Gly Val Val Gln Glu
    210                 215                 220

Lys Asp Tyr Ala Tyr Thr Gly Arg Asp Gly Ser Cys Lys Phe Asp Lys
225                 230                 235                 240

Ser Lys Val Val Ala Ser Val Ser Asn Phe Ser Val Val Ser Leu Asp
                245                 250                 255

Glu Glu Gln Ile Ala Ala Asn Leu Val Lys Asn Gly Pro Leu Ala Val
            260                 265                 270

Gly Ile Asn Ala Ala Trp Met Gln Thr Tyr Met Ser Gly Val Ser Cys
        275                 280                 285

Pro Tyr Val Cys Ala Lys Ser Arg Leu Asp His Gly Val Leu Leu Val
    290                 295                 300

Gly Phe Gly Lys Gly Ala Tyr Ala Pro Ile Arg Leu Lys Glu Lys Pro
305                 310                 315                 320

Tyr Trp Ile Val Lys Asn Ser Trp Gly Gln Asn Trp Gly Glu Gln Gly
                325                 330                 335

Tyr Tyr Lys Ile Cys Arg Gly Arg Asn Val Cys Gly Val Asp Ser Met
            340                 345                 350

Val Ser Thr Val Ala Ala Gln Ser Asn Asn
        355                 360
```

<210> SEQ ID NO 56
<211> LENGTH: 138
<212> TYPE: PRT
<213> ORGANISM: Coffea arabica

<400> SEQUENCE: 56

Met Ala Lys Pro Ser Ser Leu Leu Thr Leu Pro Ser Phe Leu Leu
1               5                   10                  15

Ile Phe Phe Ile Leu Ala Leu Phe Ser Thr Thr Leu Gln Val Asn Ala
                20                  25                  30

Leu Gly Arg Lys Val Gly Ala Arg Glu Lys Ile Glu Asp Val Lys Ser
            35                  40                  45

Asn Lys Glu Val Gln Glu Leu Gly Tyr Cys Val Ser Glu Tyr Asn
    50                  55                  60

Lys Ser Leu Arg Lys Lys Asn Asn Glu Ser Gly Ala Pro Ile Ile Phe
65                  70                  75                  80

Thr Ser Val Val Glu Ala Glu Lys Gln Val Val Ala Ile Lys Tyr Tyr
                85                  90                  95

Leu Lys Ile Lys Ala Thr Thr Ser Ser Gly Val Pro Lys Val Tyr Asp
            100                 105                 110

Ala Ile Val Val Arg Pro Trp Val His Thr Lys Pro Arg Gln Leu
        115                 120                 125

Leu Asn Phe Ser Pro Ser Pro Ala Thr Lys
    130                 135

<210> SEQ ID NO 57
<211> LENGTH: 123
<212> TYPE: PRT
<213> ORGANISM: Malus xdomestica

<400> SEQUENCE: 57

Met Met Lys Val Pro Ile Phe Ala Leu Leu Ile Cys Leu Leu Phe Val
1               5                   10                  15

Ala Ser Asn Gly Tyr Gly Gly Met Val Gly Gly Arg Lys Glu Ile Glu
                20                  25                  30

Asn Val Lys Thr Asn Lys Glu Val Gln Glu Leu Gly Arg Phe Ser Val
            35                  40                  45

Glu Glu Tyr Asn Arg Gln Arg Gly Thr Gln Lys Met Gln Gly Gly Gly
    50                  55                  60

Glu Leu Gln Phe Leu Glu Val Val Glu Ala Gln Ser Gln Val Val Ser
65                  70                  75                  80

Gly Ile Lys Tyr Tyr Leu Lys Val Ser Ala Val Arg Asn Gly Val His
                85                  90                  95

Arg Leu Phe Asp Ser Glu Val Val Val Lys Pro Trp Leu Arg Ser Lys
            100                 105                 110

Gln Leu Leu Asn Phe Ala Pro His Gly Pro Lys
        115                 120

<210> SEQ ID NO 58
<211> LENGTH: 123
<212> TYPE: PRT
<213> ORGANISM: Helianthus annuus

<400> SEQUENCE: 58

Met Ser Ser Lys Leu Pro Ile Thr Phe Phe Ile Ile Ser Leu Ser Leu
1               5                   10                  15

Phe Leu Val Ala Thr Ala Ile Pro Gly Gly Arg Thr Lys Val Lys Asn
                20                  25                  30

Val Lys Thr Asp Thr Glu Ile Gln Gln Leu Gly Ser Tyr Ser Val Asp
                35                  40                  45

Glu Tyr Lys Arg Leu Gln Arg Thr Lys Lys Thr Gly Ala Gly Asp Leu
 50                  55                  60

Lys Phe Ser Gln Val Ile Ala Ala Glu Thr Gln Val Val Ala Gly Thr
 65                  70                  75                  80

Lys Tyr Tyr Leu Lys Ile Glu Ala Ile Tyr Lys Gly Gly Lys Met Lys
                85                  90                  95

Val Phe Asp Ala Glu Val Val Gln Ser Trp Lys His Ser Lys Lys
                100                 105                 110

Leu Leu Gly Phe Lys Pro Ala Pro Val Asp Lys
                115                 120

<210> SEQ ID NO 59
<211> LENGTH: 99
<212> TYPE: PRT
<213> ORGANISM: Rumex obtusifolius

<400> SEQUENCE: 59

Met Ala Thr Ile Gly Gly Ile Lys Gln Val Glu Gly Ser Ala Asn Ser
 1               5                  10                  15

Leu Glu Val Glu Ser Leu Ala Lys Phe Ala Val Glu Asp His Asn Lys
                20                  25                  30

Lys Gln Asn Ala Met Leu Glu Phe Ser Lys Val Val Asn Thr Lys Glu
                35                  40                  45

Gln Val Val Ala Gly Thr Met Tyr Tyr Ile Thr Leu Glu Ala Thr Asp
 50                  55                  60

Gly Gly Lys Lys Val Tyr Glu Ala Lys Val Trp Val Lys Pro Trp
 65                  70                  75                  80

Met Asn Phe Lys Gln Val Gln Glu Phe Lys Leu Leu Gly Asp Gln Gly
                85                  90                  95

Ser Thr Ser

<210> SEQ ID NO 60
<211> LENGTH: 144
<212> TYPE: PRT
<213> ORGANISM: Arabidopsis thaliana

<400> SEQUENCE: 60

Met Leu Lys Val Ser Leu Val Leu Ser Leu Leu Gly Phe Leu Val Ile
 1               5                  10                  15

Ala Val Val Thr Pro Ser Ala Ala Asn Pro Phe Arg Lys Ser Val Val
                20                  25                  30

Leu Gly Gly Lys Ser Gly Val Pro Asn Ile Arg Thr Asn Arg Glu Ile
                35                  40                  45

Gln Gln Leu Gly Arg Tyr Cys Val Glu Gln Phe Asn Gln Gln Ala Gln
 50                  55                  60

Asn Glu Gln Gly Asn Ile Gly Ser Ile Ala Lys Thr Asp Thr Ala Ile
 65                  70                  75                  80

Ser Asn Pro Leu Gln Phe Ser Arg Val Val Ser Ala Gln Lys Gln Val
                85                  90                  95

Val Ala Gly Leu Lys Tyr Tyr Leu Arg Ile Glu Val Thr Gln Pro Asn
                100                 105                 110

Gly Ser Thr Arg Met Phe Asp Ser Val Val Ile Gln Pro Trp Leu
                115                 120                 125

His Ser Lys Gln Leu Leu Gly Phe Thr Pro Val Val Ser Pro Val Tyr

<210> SEQ ID NO 61
<211> LENGTH: 98
<212> TYPE: PRT
<213> ORGANISM: Coffea arabica

<400> SEQUENCE: 61

Met Ala Lys Val Gly Gly Ile Ser Glu Ser Lys Gly Asn Glu Asn Ser
1               5                   10                  15

Leu Glu Ile Glu Ser Leu Ala Lys Phe Ala Val Asp Asp Tyr Asn Lys
                20                  25                  30

Lys Gln Asn Ala Leu Leu Glu Phe Gln Lys Val Ile Asn Ser Lys Glu
            35                  40                  45

Gln Val Val Ala Gly Thr Val Tyr Tyr Leu Thr Ile Glu Val Lys Asp
        50                  55                  60

Gly Asn Glu Lys Lys Leu Tyr Glu Ala Lys Val Trp Val Lys Pro Trp
65                  70                  75                  80

Leu Asn Phe Lys Glu Val Gln Glu Phe Lys Pro Ala Ala Gly Asp Thr
                85                  90                  95

Ser Ala

<210> SEQ ID NO 62
<211> LENGTH: 99
<212> TYPE: PRT
<213> ORGANISM: Rumex obtusifolius

<400> SEQUENCE: 62

Met Ala Thr Ile Gly Gly Ile Lys Gln Val Glu Gly Ser Ala Asn Ser
1               5                   10                  15

Leu Glu Val Glu Ser Leu Ala Lys Phe Ala Val Glu Asp His Asn Lys
                20                  25                  30

Lys Gln Asn Ala Met Leu Glu Phe Ser Lys Val Val Asn Thr Lys Glu
            35                  40                  45

Gln Val Val Ala Gly Thr Met Tyr Tyr Ile Thr Leu Glu Ala Thr Asp
        50                  55                  60

Gly Gly Lys Lys Lys Val Tyr Glu Ala Lys Val Trp Val Lys Pro Trp
65                  70                  75                  80

Met Asn Phe Lys Gln Val Gln Glu Phe Lys Leu Leu Gly Asp Gln Gly
                85                  90                  95

Ser Thr Ser

<210> SEQ ID NO 63
<211> LENGTH: 98
<212> TYPE: PRT
<213> ORGANISM: Dianthus caryophyllus

<400> SEQUENCE: 63

Met Ala Thr Val Gly Gly Ile Lys Asp Ser Gly Gly Ser Ser Ala Asn
1               5                   10                  15

Ser Leu Glu Ile Asp Glu Leu Ala Lys Phe Ala Val Asp His Tyr Asn
                20                  25                  30

Ser Lys Glu Asn Ala Leu Leu Glu Phe Gln Arg Val Val Asn Thr Lys
            35                  40                  45

Glu Gln Val Val Ala Gly Thr Ile Tyr Tyr Ile Thr Leu Glu Ala Thr
        50                  55                  60

Asp Gly Gly Val Lys Lys Leu Tyr Glu Ala Lys Val Trp Val Lys Pro
65                  70                  75                  80

Trp Val Asn Phe Lys Glu Val Gln Asp Phe Lys Tyr Val Gly Asp Ala
            85                  90                  95

Ser Ala

<210> SEQ ID NO 64
<211> LENGTH: 101
<212> TYPE: PRT
<213> ORGANISM: Manihot esculenta

<400> SEQUENCE: 64

Met Ala Thr Leu Gly Gly Ile Lys Glu Val Glu Ser Ala Asn Ser
1               5                   10                  15

Val Glu Ile Asp Asn Leu Ala Arg Phe Ala Val Asp Asp Tyr Asn Lys
            20                  25                  30

Lys Gln Asn Ala Leu Leu Glu Phe Lys Arg Val Val Ser Thr Lys Gln
        35                  40                  45

Gln Val Val Ala Gly Thr Met Tyr Tyr Ile Thr Leu Glu Val Ala Asp
    50                  55                  60

Gly Gly Gln Thr Lys Val Tyr Glu Ala Lys Val Trp Glu Lys Pro Trp
65                  70                  75                  80

Leu Asn Phe Lys Glu Val Gln Glu Phe Lys Pro Ile Gly Val Ala Pro
                85                  90                  95

Ser Asp Ser Thr Ala
            100

<210> SEQ ID NO 65
<211> LENGTH: 124
<212> TYPE: PRT
<213> ORGANISM: Coffea arabica

<400> SEQUENCE: 65

Met Ala Ser Ala Phe Pro His Leu Leu Leu Thr Thr Leu Ala Ala
1               5                   10                  15

Ile Cys Leu Phe Ser Asp Val Pro Ser Ala Ala Leu Gly Gly Arg Pro
            20                  25                  30

Lys Asp Ala Leu Val Gly Gly Trp Ser Lys Ala Asp Pro Lys Asp Pro
        35                  40                  45

Glu Val Leu Glu Asn Gly Lys Phe Ala Ile Asp Glu His Asn Lys Glu
    50                  55                  60

Ala Gly Thr Lys Leu Glu Phe Lys Thr Val Val Glu Ala Gln Lys Gln
65                  70                  75                  80

Val Val Ala Gly Thr Asn Tyr Lys Ile Val Ile Lys Ala Leu Asp Gly
                85                  90                  95

Thr Ala Ser Asn Leu Tyr Glu Ala Ile Val Trp Val Lys Pro Trp Leu
            100                 105                 110

Lys Phe Lys Lys Leu Thr Ser Phe Arg Lys Leu Pro
        115                 120

<210> SEQ ID NO 66
<211> LENGTH: 118
<212> TYPE: PRT
<213> ORGANISM: Citrusxparadisi

<400> SEQUENCE: 66

Met Asn Gln Arg Phe Cys Cys Leu Ile Val Leu Phe Leu Ser Val Val
1               5                   10                  15

Pro Leu Leu Ala Ala Gly Asp Arg Lys Gly Ala Leu Val Gly Gly Trp
            20                  25                  30

```
Lys Pro Ile Glu Asp Pro Lys Glu Lys His Val Met Glu Ile Gly Gln
            35                  40                  45

Phe Ala Val Thr Glu Tyr Asn Lys Gln Ser Lys Ser Ala Leu Lys Phe
     50                  55                  60

Glu Ser Val Glu Lys Gly Glu Thr Gln Val Val Ser Gly Thr Asn Tyr
 65                  70                  75                  80

Arg Leu Ile Leu Val Val Lys Asp Gly Pro Ser Thr Lys Lys Phe Glu
                 85                  90                  95

Ala Val Val Trp Glu Lys Pro Trp Glu His Phe Lys Ser Leu Thr Ser
            100                 105                 110

Phe Lys Pro Met Val Lys
            115

<210> SEQ ID NO 67
<211> LENGTH: 116
<212> TYPE: PRT
<213> ORGANISM: Actinidia deliciosa

<400> SEQUENCE: 67

Met Val Pro Lys Pro Leu Ser Leu Leu Phe Leu Leu Leu Ala Leu
 1               5                  10                  15

Ser Ala Ala Val Val Gly Gly Arg Lys Leu Val Ala Ala Gly Gly Trp
            20                  25                  30

Arg Pro Ile Glu Ser Leu Asn Ser Ala Glu Val Gln Asp Val Ala Gln
            35                  40                  45

Phe Ala Val Ser Glu His Asn Lys Gln Ala Asn Asp Glu Leu Gln Tyr
     50                  55                  60

Gln Ser Val Val Arg Gly Tyr Thr Gln Val Val Ala Gly Thr Asn Tyr
 65                  70                  75                  80

Arg Leu Val Ile Ala Ala Lys Asp Gly Ala Val Val Gly Asn Tyr Glu
                 85                  90                  95

Ala Val Val Trp Asp Lys Pro Trp Met His Phe Arg Asn Leu Thr Ser
            100                 105                 110

Phe Arg Lys Val
            115

<210> SEQ ID NO 68
<211> LENGTH: 122
<212> TYPE: PRT
<213> ORGANISM: Arabidopsis thaliana

<400> SEQUENCE: 68

Met Thr Ser Lys Val Val Phe Leu Leu Leu Ser Leu Val Val Leu
 1               5                  10                  15

Leu Leu Pro Leu Tyr Ala Ser Ala Ala Arg Val Gly Gly Trp Ser
            20                  25                  30

Pro Ile Ser Asn Val Thr Asp Pro Gln Val Val Glu Ile Gly Glu Phe
            35                  40                  45

Ala Val Ser Glu Tyr Asn Lys Arg Ser Glu Ser Gly Leu Lys Phe Glu
     50                  55                  60

Thr Val Val Ser Gly Glu Thr Gln Val Val Ser Gly Thr Asn Tyr Arg
 65                  70                  75                  80

Leu Lys Val Ala Ala Asn Asp Gly Asp Val Ser Lys Asn Tyr Leu
                 85                  90                  95

Ala Ile Val Trp Asp Lys Pro Trp Met Lys Phe Arg Asn Leu Thr Ser
            100                 105                 110
```

```
Phe Glu Pro Ala Asn Asn Gly Arg Phe Leu
            115                 120

<210> SEQ ID NO 69
<211> LENGTH: 119
<212> TYPE: PRT
<213> ORGANISM: Coffea arabica

<400> SEQUENCE: 69

Met Ala Thr Val Ala Ala Lys Ser Ala Thr Ala Ile Gly Ala Gly
1               5                   10                  15

Gln Lys Asn Met Val Gly Gly Gly Leu Ser Ser Thr Val Pro Pro Arg
                20                  25                  30

Ser Ser Thr Val Asn Pro Lys Asp Pro His Val Ile Gln Ile Ala Gln
            35                  40                  45

Phe Ala Val Ala Asn Tyr Asn Ala Lys Ala Gly Thr Thr Val Val Trp
    50                  55                  60

Leu Asn Val Glu Tyr Gly Phe Trp Trp Ile Asp Asp Thr Tyr Tyr
65                  70                  75                  80

Met Leu Ala Ile Lys Thr Gln Asp Leu Thr Gly Thr His Cys Asp Val
                85                  90                  95

Ala Leu Val Arg Glu Ile Ser Glu Ser Asn Gly Thr Tyr Ser Leu Lys
            100                 105                 110

Trp Tyr Asn His Asn Asn Lys
            115

<210> SEQ ID NO 70
<211> LENGTH: 118
<212> TYPE: PRT
<213> ORGANISM: Citrusxparadisi

<400> SEQUENCE: 70

Met Asn Gln Arg Phe Cys Cys Leu Ile Val Ile Phe Leu Ser Val Val
1               5                   10                  15

Pro Leu Leu Ala Ala Gly Asp Arg Lys Gly Ala Leu Val Gly Gly Trp
                20                  25                  30

Lys Pro Ile Glu Asp Pro Lys Glu Lys His Val Met Glu Ile Gly Gln
            35                  40                  45

Phe Ala Val Thr Glu Tyr Asn Lys Gln Ser Lys Ser Ala Leu Lys Phe
    50                  55                  60

Glu Ser Val Glu Lys Gly Glu Thr Gln Val Val Ser Gly Thr Asn Tyr
65                  70                  75                  80

Arg Leu Ile Leu Val Val Lys Asp Gly Pro Ser Thr Lys Lys Phe Glu
                85                  90                  95

Ala Val Val Trp Glu Lys Pro Trp Glu His Phe Lys Ser Leu Thr Ser
            100                 105                 110

Phe Lys Pro Met Val Lys
            115

<210> SEQ ID NO 71
<211> LENGTH: 122
<212> TYPE: PRT
<213> ORGANISM: Arabidopsis thaliana

<400> SEQUENCE: 71

Met Thr Ser Lys Val Val Phe Leu Leu Leu Ser Leu Val Val Leu
1               5                   10                  15

Leu Leu Pro Leu Tyr Ala Ser Ala Ala Ala Arg Val Gly Gly Trp Ser
                20                  25                  30
```

Pro Ile Ser Asn Val Thr Asp Pro Gln Val Val Glu Ile Gly Glu Phe
            35                  40                  45

Ala Val Ser Glu Tyr Asn Lys Arg Ser Glu Ser Gly Leu Lys Phe Glu
 50                  55                  60

Thr Val Val Ser Gly Glu Thr Gln Val Val Ser Gly Thr Asn Tyr Arg
 65                  70                  75                  80

Leu Lys Val Ala Ala Asn Asp Gly Asp Gly Val Ser Lys Asn Tyr Leu
                 85                  90                  95

Ala Ile Val Trp Asp Lys Pro Trp Met Lys Phe Arg Asn Leu Thr Ser
                100                 105                 110

Phe Glu Pro Ala Asn Asn Gly Arg Phe Leu
            115                 120

<210> SEQ ID NO 72
<211> LENGTH: 359
<212> TYPE: PRT
<213> ORGANISM: Coffea arabica

<400> SEQUENCE: 72

Met Lys Met Gly Lys Ala Phe Leu Phe Ala Val Val Leu Ala Val Ile
 1               5                  10                  15

Leu Val Ala Ala Met Ser Met Glu Ile Thr Glu Arg Asp Leu Ala Ser
                 20                  25                  30

Glu Glu Ser Leu Trp Asp Leu Tyr Glu Arg Trp Arg Ser His His Thr
             35                  40                  45

Val Ser Arg Asp Leu Ser Glu Lys Arg Lys Arg Phe Asn Val Phe Lys
 50                  55                  60

Ala Asn Val His His Ile His Lys Val Asn Gln Lys Asp Lys Pro Tyr
 65                  70                  75                  80

Lys Leu Lys Leu Asn Ser Phe Ala Asp Met Thr Asn His Glu Phe Arg
                 85                  90                  95

Glu Phe Tyr Ser Ser Lys Val Lys His Tyr Arg Met Leu His Gly Ser
                100                 105                 110

Arg Ala Asn Thr Gly Phe Met His Gly Lys Thr Glu Ser Leu Pro Ala
            115                 120                 125

Ser Val Asp Trp His Lys Gln Gly Ala Val Thr Gly Val Lys Asn Gln
130                 135                 140

Gly Lys Cys Gly Ser Cys Trp Ala Phe Ser Thr Val Val Gly Val Glu
145                 150                 155                 160

Gly Ile Asn Lys Ile Lys Thr Gly Gln Leu Val Ser Leu Ser Glu Gln
                165                 170                 175

Glu Leu Val Asp Cys Glu Thr Asp Asn Glu Gly Cys Asn Gly Gly Leu
            180                 185                 190

Met Glu Asn Ala Tyr Glu Phe Ile Lys Lys Ser Gly Gly Ile Thr Thr
            195                 200                 205

Glu Arg Leu Tyr Pro Tyr Lys Ala Arg Asp Gly Ser Cys Asp Ser Ser
210                 215                 220

Lys Met Asn Ala Pro Ala Val Thr Ile Asp Gly His Glu Met Val Pro
225                 230                 235                 240

Ala Asn Asp Glu Asn Ala Leu Met Lys Ala Val Ala Asn Gln Pro Val
                245                 250                 255

Ser Val Ala Ile Asp Ala Ser Gly Ser Asp Met Gln Phe Tyr Ser Glu
            260                 265                 270

Gly Val Tyr Ala Gly Asp Ser Cys Gly Asn Glu Leu Asp His Gly Val
            275                 280                 285

```
Ala Val Val Gly Tyr Gly Thr Ala Leu Asp Gly Thr Lys Tyr Trp Ile
    290                 295                 300

Val Lys Asn Ser Trp Gly Thr Gly Trp Gly Glu Gln Gly Tyr Ile Arg
305                 310                 315                 320

Met Gln Arg Gly Val Asp Ala Ala Glu Gly Val Cys Gly Ile Ala
                325                 330                 335

Met Glu Ala Ser Tyr Pro Leu Lys Leu Ser Ser His Asn Pro Lys Pro
                340                 345                 350

Ser Pro Pro Lys Asp Asp Leu
        355

<210> SEQ ID NO 73
<211> LENGTH: 358
<212> TYPE: PRT
<213> ORGANISM: Dacus carrota

<400> SEQUENCE: 73

Met Lys Thr Gly Leu Val Leu Val Phe Leu Ser Gly Ala Leu Val
1               5                   10                  15

Phe Thr Val Ala Glu Asn Phe Glu Val Thr Glu His Asp Leu Ala Thr
                20                  25                  30

Asp Glu Ser Leu Trp Asp Leu Tyr Glu Arg Trp Arg Ser His His Thr
                35                  40                  45

Val Ser Arg Asp Leu Thr Glu Lys Gln Ile Arg Phe Asn Val Phe Lys
    50                  55                  60

Thr Asn Val Lys His Ile His Lys Val Asn Gln Met Asn Lys Pro Tyr
65                  70                  75                  80

Lys Leu Glu Val Asn Lys Phe Ala Asp Met Thr Tyr His Glu Phe Arg
                85                  90                  95

Asn Ser Tyr Gly Gly Ser Lys Val Lys His Phe Arg Ser Leu Arg Gly
                100                 105                 110

Asp Arg Ala Arg Thr Gly Phe Met His Glu Asn Thr Lys His Leu Pro
            115                 120                 125

Ser Ser Val Asp Trp Arg Lys His Gly Ala Val Thr Pro Ile Lys Asn
        130                 135                 140

Gln Gly Arg Cys Gly Ser Cys Trp Ala Phe Ser Ala Ile Val Gly Val
145                 150                 155                 160

Glu Gly Ile Asn Lys Ile Lys Thr Asn Gln Leu Val Ser Leu Ser Glu
                165                 170                 175

Gln Glu Leu Val Asp Cys Glu Ser Asp Asn Gln Gly Cys Asn Gly Gly
                180                 185                 190

Leu Met Glu Asn Ala Leu Glu Phe Ile Lys Arg Ser Gly Gly Val Thr
            195                 200                 205

Thr Glu Arg Val Tyr Pro Tyr Arg Ala Arg Asp Glu Arg Cys Asp Ala
    210                 215                 220

Thr Lys Met Asn Ala Pro Val Val Lys Ile Asp Gly His Glu Asn Val
225                 230                 235                 240

Pro Glu Asn Asn Glu Tyr Ala Leu Ala Gln Ala Val Ala Asn Gln Pro
                245                 250                 255

Val Ser Val Ala Ile Asp Ala Gly Gly Ser Asp Met Gln Phe Tyr Arg
                260                 265                 270

Glu Gly Val Tyr Thr Gly Glu Cys Gly Thr Glu Leu Asp His Gly Val
            275                 280                 285

Ala Val Val Gly Tyr Gly Ala Thr Asn Asp Gly Thr Lys Tyr Trp Ile
        290                 295                 300
```

Val Lys Asn Ser Trp Gly Thr Asp Trp Gly Glu Arg Gly Tyr Ile Arg
305                 310                 315                 320

Met Val Arg Asp Ile Asn Ala Ala Glu Gly Ile Cys Gly Ile Ala Met
            325                 330                 335

Glu Ala Ser Tyr Pro Val Lys Leu Thr Ala Asp Asn Pro Lys Ala Val
            340                 345                 350

Pro Gln Lys Asp Glu Leu
        355

<210> SEQ ID NO 74
<211> LENGTH: 372
<212> TYPE: PRT
<213> ORGANISM: Ricinus communis

<400> SEQUENCE: 74

Met Gln Lys Phe Ile Leu Leu Ala Leu Ser Leu Ala Leu Val Leu Ala
1               5                   10                  15

Ile Thr Glu Ser Phe Asp Phe His Glu Lys Leu Glu Ser Glu Glu
            20                  25                  30

Ser Leu Trp Gly Leu Tyr Glu Arg Trp Arg Ser His His Phe Thr Thr
        35                  40                  45

Val Ser Arg Ser Leu His Glu Lys Gln Lys Arg Phe Asn Val Phe Lys
    50                  55                  60

His Asn Ala Met His Val His Asn Ala Asn Lys Met Asp Lys Pro Tyr
65                  70                  75                  80

Lys Leu Lys Leu Asn Lys Phe Ala Asp Met Thr Asn His Glu Phe Arg
                85                  90                  95

Asn Thr Tyr Ser Gly Ser Lys Val Lys His Phe Thr His Arg Met Phe
            100                 105                 110

Arg Gly Gly Pro Arg Gly Asn Gly Thr Phe Met Tyr Glu Lys Val Asp
        115                 120                 125

Thr Val Pro Ala Ser Val Asp Trp Arg Lys Lys Gly Ala Val Thr Ser
    130                 135                 140

Val Lys Asp Gln Gly Gln Cys Gly Ser Cys Trp Ala Phe Ser Thr Ile
145                 150                 155                 160

Val Ala Val Glu Gly Ile Asn Phe Thr Gln Ile Lys Thr Asn Lys Leu
                165                 170                 175

Val Ser Leu Ser Glu Gln Glu Leu Val Asp Cys Asp Thr Asp Gln Asn
            180                 185                 190

Gln Gly Cys Asn Gly Gly Leu Met Asp Tyr Ala Phe Glu Phe Ile Lys
        195                 200                 205

Gln Arg Gly Gly Ile Thr Thr Glu Ala Asn Tyr Pro Tyr Glu Ala Tyr
    210                 215                 220

Asp Gly Thr Cys Phe Thr Asp Val Ser Lys Glu Lys Ala Pro Ala Val
225                 230                 235                 240

Ser Ile Asp Gly His Glu Asn Val Pro Glu Asn Asp Glu Asn Ala Leu
                245                 250                 255

Leu Lys Ala Val Ala Asn Gln Pro Tyr Ser Val Ala Ile Asp Ala Gly
            260                 265                 270

Gly Ser Asp Phe Gln Phe Tyr Ser Glu Gly Val Phe Thr Gly Ser Cys
        275                 280                 285

Gly Phe Thr Thr Glu Leu Asp His Gly Val Ala Ile Val Gly Tyr Gly
    290                 295                 300

Thr Thr Ile Asp Gly Thr Lys Tyr Trp Thr Val Lys Asn Ser Trp Gly
305                 310                 315                 320

```
Pro Glu Trp Gly Glu Lys Gly Tyr Ile Arg Met Glu Arg Gly Ile Ser
                325                 330                 335

Asp Lys Glu Gly Leu Cys Gly Ile Ala Met Glu Ala Ser Tyr Phe Thr
            340                 345                 350

Pro Ile Lys Lys Ser Ser Asn Asn Pro Ser Gly Ile Lys Ser Ser Pro
        355                 360                 365

Lys Asp Glu Leu
    370

<210> SEQ ID NO 75
<211> LENGTH: 360
<212> TYPE: PRT
<213> ORGANISM: Helianthus annuus

<400> SEQUENCE: 75

Met Ala Lys Pro Lys Phe Ile Ala Leu Ala Leu Val Ala Leu Ser Phe
1               5                   10                  15

Leu Ser Ile Ala Gln Ser Ile Pro Phe Thr Glu Lys Asp Leu Ala Ser
            20                  25                  30

Glu Asp Ser Leu Trp Asn Leu Tyr Glu Lys Trp Arg Thr His His Thr
        35                  40                  45

Val Ala Arg Asp Leu Asp Glu Lys Asn Arg Arg Phe Asn Val Phe Lys
    50                  55                  60

Glu Asn Val Lys Phe Ile His Glu Phe Asn Gln Lys Lys Asp Ala Pro
65                  70                  75                  80

Tyr Lys Leu Ala Leu Asn Lys Phe Gly Asp Met Thr Asn Gln Glu Phe
                85                  90                  95

Arg Ser Lys Tyr Ala Gly Ser Lys Ile Gln His Ser Arg Ser Gln Arg
            100                 105                 110

Gly Ile Gln Lys Asn Thr Gly Ser Phe Met Tyr Glu Asn Val Gly Ser
        115                 120                 125

Leu Pro Ala Ala Ser Ile Asp Trp Arg Ala Lys Gly Ala Val Thr Gly
    130                 135                 140

Val Lys Asp Gln Gly Gln Cys Gly Ser Cys Trp Ala Phe Ser Thr Ile
145                 150                 155                 160

Ala Ser Val Glu Gly Ile Asn Gln Ile Lys Thr Gly Glu Leu Val Ser
                165                 170                 175

Leu Ser Glu Gln Glu Leu Val Asp Cys Asp Thr Ser Tyr Asn Glu Gly
            180                 185                 190

Cys Asn Gly Gly Leu Met Asp Tyr Ala Phe Glu Phe Ile Gln Lys Asn
        195                 200                 205

Gly Ile Thr Thr Glu Asp Ser Tyr Pro Tyr Ala Glu Gln Asp Gly Thr
    210                 215                 220

Cys Ala Ser Asn Leu Leu Asn Ser Pro Val Val Ser Ile Val Gly His
225                 230                 235                 240

Gln Asp Val Pro Ala Asn Asn Glu Asn Ala Leu Met Gln Ala Val Ala
                245                 250                 255

Asn Gln Pro Ile Ser Val Ser Ile Glu Ala Ser Gly Tyr Gly Phe Gln
            260                 265                 270

Phe Tyr Ser Glu Gly Val Phe Thr Gly Arg Cys Gly Thr Glu Leu Asp
        275                 280                 285

His Gly Val Ala Ile Val Gly Tyr Gly Ala Thr Arg Asp Gly Thr Lys
    290                 295                 300

Tyr Gly Ile Val Lys Asn Ser Trp Gly Glu Glu Trp Gly Glu Ser Gly
305                 310                 315                 320
```

```
Tyr Ile Arg Met Gln Arg Gly Ile Ser Asp Lys Arg Gly Lys Cys Gly
                325                 330                 335

Ile Ala Met Glu Ala Ser Tyr Pro Ile Lys Thr Ser Ala Asn Pro Lys
            340                 345                 350

Asn Ser Ser Thr Arg Asp Glu Leu
        355                 360

<210> SEQ ID NO 76
<211> LENGTH: 357
<212> TYPE: PRT
<213> ORGANISM: Vicia sativa

<400> SEQUENCE: 76

Met Glu Met Lys Lys Leu Leu Phe Ile Ser Leu Ser Leu Ala Leu Ile
1               5                   10                  15

Phe Thr Val Ala Asn Thr Phe Asp Phe Asn Glu His Asp Leu Glu Ser
            20                  25                  30

Glu Lys Ser Leu Trp Asn Leu Tyr Glu Arg Trp Arg Ser His His Thr
        35                  40                  45

Val Thr Arg Asn Leu Asp Glu Lys His Asn Arg Phe Asn Val Phe Lys
50                  55                  60

Ala Asn Val Met His Val His Asn Thr Asn Lys Leu Asp Lys Pro Tyr
65                  70                  75                  80

Lys Leu Lys Leu Asn Lys Phe Gly Asp Met Thr Asn Tyr Glu Phe Arg
                85                  90                  95

Arg Ile Tyr Ala Asp Ser Lys Ile Ser His His Arg Met Phe Arg Gly
            100                 105                 110

Met Ser His Glu Asn Gly Thr Phe Met Tyr Glu Asn Val Asp Val Pro
        115                 120                 125

Ser Ser Ile Asp Trp Arg Asn Lys Gly Ala Val Thr Gly Val Lys Asp
130                 135                 140

Gln Gly Gln Cys Gly Ser Cys Trp Ala Phe Ser Thr Ile Ala Ala Val
145                 150                 155                 160

Glu Gly Ile Asn Gln Ile Lys Thr Gln Lys Leu Val Ser Leu Ser Glu
                165                 170                 175

Gln Gln Leu Val Asp Cys Asp Thr Glu Glu Asn Glu Gly Cys Asn Gly
            180                 185                 190

Gly Leu Met Glu Tyr Ala Phe Glu Phe Ile Lys Gln Asn Gly Ile Thr
        195                 200                 205

Thr Glu Ser Asn Tyr Pro Tyr Ala Ala Lys Asp Asp Thr Cys Asp Val
210                 215                 220

Glu Lys Glu Asp Lys Ala Val Ser Ile Asp Gly His Glu Asn Glx Pro
225                 230                 235                 240

Ile Asn Asn Glu Ala Ala Leu Lys Ala Ala Lys Gln Pro Val Ser
                245                 250                 255

Val Ala Ile Asp Ala Gly Gly Tyr Asn Phe Gln Phe Tyr Ser Glu Gly
            260                 265                 270

Val Phe Thr Gly His Cys Asp Thr Asp Leu His Gly Val Ala Ile
        275                 280                 285

Val Gly Tyr Gly Val Thr Gln Asp Arg Thr Lys Tyr Trp Ile Met Lys
        290                 295                 300

Asn Ser Trp Gly Ser Glu Trp Gly Glu Gln Gly Tyr Ile Arg Met Gln
305                 310                 315                 320

Arg Gly Ile Ser Ser Arg Glu Gly Leu Cys Gly Ile Ala Met Glu Ala
                325                 330                 335
```

<210> SEQ ID NO 77
<211> LENGTH: 360
<212> TYPE: PRT
<213> ORGANISM: Pisum sativum

<400> SEQUENCE: 77

Met Glu Met Lys Lys Leu Leu Leu Phe Ser Leu Ser Leu Ala Leu Ile
1               5                   10                  15

Phe Arg Ala Thr Asn Thr Phe Asp Phe Asn Glu His Asp Leu Asp Ser
            20                  25                  30

Glu Lys Ser Leu Trp Asp Leu Tyr Glu Arg Trp Arg Ser His His Thr
        35                  40                  45

Val Thr Arg Ser Leu Asp Glu Lys His Asn Arg Phe Asn Val Phe Lys
    50                  55                  60

Ala Asn Val Met His Val His Asn Thr Asn Lys Leu Asp Lys Pro Tyr
65                  70                  75                  80

Lys Leu Lys Leu Asn Lys Phe Ala Asp Met Thr Asn Tyr Glu Phe Arg
                85                  90                  95

Arg Ile Tyr Ala Asp Ser Lys Val Ser His His Arg Met Phe Arg Gly
            100                 105                 110

Met Ser Asn Glu Met Gly Thr Phe Met Tyr Gln Asn Val Lys Asn Val
        115                 120                 125

Pro Ser Ser Ile Asp Trp Arg Lys Lys Gly Ala Val Thr Asp Val Lys
    130                 135                 140

Asp Gln Gly Gln Cys Gly Ser Cys Trp Ala Phe Ser Thr Ile Val Ala
145                 150                 155                 160

Val Glu Gly Ile Asn Gln Ile Lys Thr Gln Lys Leu Val Ser Leu Ser
                165                 170                 175

Glu Gln Glu Leu Val Asp Cys Asp Thr Gly Gly Asn Glu Gly Cys Asn
            180                 185                 190

Gly Gly Leu Met Glu Tyr Ala Phe Glu Phe Ile Lys Gln Asn Gly Ile
        195                 200                 205

Thr Thr Glu Ser Asn Tyr Pro Tyr Ala Ala Lys Asp Gly Thr Cys Asp
    210                 215                 220

Leu Lys Lys Glu Asp Lys Ala Glu Val Ser Ile Asp Gly Tyr Glu Asn
225                 230                 235                 240

Val Pro Ile Asn Asn Glu Ala Ala Leu Leu Lys Ala Ala Ala Lys Gln
                245                 250                 255

Pro Val Ser Val Ala Ile Asp Ala Gly Gly Tyr Asn Phe Gln Phe Tyr
            260                 265                 270

Ser Glu Gly Val Phe Ser Gly His Cys Gly Thr Asp Leu Asn His Gly
        275                 280                 285

Val Ala Val Val Gly Tyr Gly Val Thr Gln Asp Arg Thr Lys Tyr Trp
    290                 295                 300

Ile Val Lys Asn Ser Trp Gly Ser Glu Trp Gly Glu Gln Gly Tyr Ile
305                 310                 315                 320

Arg Met Gln Arg Gly Ile Ser His Lys Glu Gly Leu Cys Gly Ile Ala
                325                 330                 335

Met Glu Ala Ser Tyr Pro Ile Lys Lys Ser Ser Thr Asn Pro Thr Glu
            340                 345                 350

Ser Ser Thr Leu Lys Asp Glu Leu
            355                 360

<210> SEQ ID NO 78
<211> LENGTH: 361
<212> TYPE: PRT
<213> ORGANISM: Vigna mungo

<400> SEQUENCE: 78

Met Ala Met Lys Lys Leu Leu Trp Val Val Leu Ser Leu Ser Leu Val
1               5                   10                  15

Leu Gly Val Ala Asn Ser Phe Asp Phe His Glu Lys Asp Leu Glu Ser
            20                  25                  30

Glu Glu Ser Leu Trp Asp Leu Tyr Glu Arg Trp Arg Ser His His Thr
        35                  40                  45

Val Ser Arg Ser Leu Gly Glu Lys His Lys Arg Phe Asn Val Phe Lys
    50                  55                  60

Ala Asn Val Met His Val His Asn Thr Asn Lys Met Asp Lys Pro Tyr
65                  70                  75                  80

Lys Leu Lys Leu Asn Lys Phe Ala Asp Met Thr Asn His Glu Phe Arg
                85                  90                  95

Ser Thr Tyr Ala Gly Ser Lys Val Asn His His Lys Met Phe Arg Gly
            100                 105                 110

Ser Gln His Gly Ser Gly Thr Phe Met Tyr Glu Lys Val Gly Ser Val
        115                 120                 125

Pro Ala Ser Val Asp Trp Arg Lys Lys Gly Ala Val Thr Asp Val Lys
    130                 135                 140

Asp Gln Gly Gln Cys Gly Ser Cys Trp Ala Phe Ser Thr Ile Val Ala
145                 150                 155                 160

Val Glu Gly Ile Asn Gln Ile Lys Thr Asn Lys Leu Val Ser Leu Ser
                165                 170                 175

Glu Gln Glu Leu Val Asp Cys Asp Lys Glu Glu Asn Gln Gly Cys Asn
            180                 185                 190

Gly Gly Leu Met Glu Ser Ala Phe Glu Phe Ile Lys Gln Lys Gly Gly
        195                 200                 205

Ile Thr Thr Glu Ser Asn Tyr Pro Tyr Thr Ala Gln Glu Gly Thr Cys
    210                 215                 220

Asp Glu Ser Lys Val Asn Asp Leu Ala Val Ser Ile Asp Gly His Glu
225                 230                 235                 240

Asn Val Pro Val Asn Asp Glu Asn Ala Leu Leu Lys Ala Val Ala Asn
                245                 250                 255

Gln Pro Val Ser Val Ala Ile Asp Ala Gly Gly Tyr Asn Phe Gln Phe
            260                 265                 270

Tyr Ser Glu Gly Val Phe Thr Gly His Cys Asp Thr Asp Leu Asn His
        275                 280                 285

Gly Val Ala Ile Val Gly Tyr Gly Val Thr Gln Asp Arg Thr Lys Tyr
    290                 295                 300

Trp Ile Met Lys Asn Ser Trp Gly Ser Glu Trp Gly Glu Gln Gly Tyr
305                 310                 315                 320

Ile Arg Met Gln Arg Gly Ile Ser Ser Arg Glu Gly Leu Cys Gly Ile
                325                 330                 335

Ala Met Glu Ala Ser Tyr Pro Ile Lys Lys Ser Ser Thr Lys Pro Thr
            340                 345                 350

Glu Ser Ser Ile Leu Lys Asp Glu Leu
        355                 360

<210> SEQ ID NO 79
<211> LENGTH: 361
<212> TYPE: PRT
<213> ORGANISM: Phaseolus vulgaris

<400> SEQUENCE: 79

Met Ala Thr Lys Lys Leu Leu Trp Val Val Leu Ser Phe Ser Leu Val
1               5                   10                  15

Leu Gly Val Ala Asn Ser Phe Asp Phe His Asp Lys Asp Leu Ala Ser
            20                  25                  30

Glu Glu Ser Leu Trp Asp Leu Tyr Glu Arg Trp Arg Ser His His Thr
        35                  40                  45

Val Ser Arg Ser Leu Gly Glu Lys His Lys Arg Phe Asn Val Phe Lys
50                  55                  60

Ala Asn Leu Met His Val His Asn Thr Asn Lys Met Asp Lys Pro Tyr
65                  70                  75                  80

Lys Leu Lys Leu Asn Lys Phe Ala Asp Met Thr Asn His Glu Phe Arg
                85                  90                  95

Ser Thr Tyr Ala Gly Ser Lys Val Asn His Pro Arg Met Phe Arg Gly
            100                 105                 110

Thr Pro His Glu Asn Gly Ala Phe Met Tyr Glu Lys Val Ser Val Pro
        115                 120                 125

Pro Ser Val Asp Trp Arg Lys Lys Gly Ala Val Thr Asp Val Lys Asp
130                 135                 140

Gln Gly Gln Cys Gly Ser Cys Trp Ala Phe Ser Thr Val Val Ala Val
145                 150                 155                 160

Glu Gly Ile Asn Gln Ile Lys Thr Asn Lys Leu Val Ala Leu Ser Glu
                165                 170                 175

Gln Glu Leu Val Asp Cys Asp Lys Glu Glu Asn Gln Gly Cys Asn Gly
            180                 185                 190

Gly Leu Met Glu Ser Ala Phe Glu Phe Ile Lys Gln Lys Gly Gly Ile
        195                 200                 205

Thr Thr Glu Ser Asn Tyr Pro Tyr Lys Ala Gln Glu Gly Thr Cys Asp
210                 215                 220

Ala Ser Lys Val Asn Asp Leu Ala Val Ser Ile Asp Gly His Glu Asn
225                 230                 235                 240

Val Pro Ala Asn Asp Glu Asp Ala Leu Leu Lys Ala Val Ala Asn Gln
                245                 250                 255

Pro Val Ser Val Ala Ile Asp Ala Gly Gly Ser Asp Phe Gln Phe Tyr
            260                 265                 270

Ser Glu Gly Val Phe Thr Gly Asp Cys Ser Thr Asp Leu Asn His Gly
        275                 280                 285

Val Ala Ile Val Gly Tyr Gly Thr Thr Val Asp Gly Thr Asn Tyr Gly
290                 295                 300

Ile Val Arg Asn Ser Trp Gly Pro Glu Trp Gly Glu His Gly Tyr Ile
305                 310                 315                 320

Arg Met Gln Arg Asn Ile Ser Lys Lys Glu Gly Leu Cys Gly Ile Ala
                325                 330                 335

Met Leu Pro Ser Tyr Pro Ile Lys Asn Ser Ser Asp Asn Pro Thr Gly
            340                 345                 350

Ser Phe Ser Ser Pro Lys Asp Glu Leu
        355                 360

<210> SEQ ID NO 80

```
<211> LENGTH: 374
<212> TYPE: PRT
<213> ORGANISM: Glycine max

<400> SEQUENCE: 80
```

| | | | | | | | | | | | | | | |
|---|---|---|---|---|---|---|---|---|---|---|---|---|---|---|
| Met | Ala | Met | Lys | Lys | Leu | Leu | Trp | Val | Val | Leu | Ser | Leu | Ser | Leu | Val |
| 1 | | | | 5 | | | | | 10 | | | | | 15 | |
| Leu | Gly | Ser | Ala | Asn | Ser | Phe | Asp | Phe | His | Asp | Lys | Asp | Leu | Ala | Ser |
| | | | 20 | | | | | 25 | | | | | 30 | | |
| Glu | Glu | Ser | Phe | Trp | Asp | Leu | Tyr | Glu | Arg | Trp | Arg | Ser | Phe | Thr | His |
| | | 35 | | | | | 40 | | | | | 45 | | | |
| His | Thr | Val | Ser | Arg | Ser | Leu | Gly | Asp | Lys | His | Lys | Arg | Phe | Asn | Val |
| | 50 | | | | | 55 | | | | | 60 | | | | |
| Phe | Lys | Ala | Asn | Val | Met | His | Val | His | Asn | Thr | Asn | Lys | Met | Asp | Lys |
| 65 | | | | | 70 | | | | | 75 | | | | | 80 |
| Pro | Tyr | Lys | Leu | Lys | Leu | Asn | Lys | Phe | Ala | Asp | Met | Thr | Asn | His | Glu |
| | | | | 85 | | | | | 90 | | | | | 95 | |
| Phe | Arg | Ser | Thr | Tyr | Ala | Gly | Ser | Lys | Val | Phe | Thr | Asn | His | His | Arg |
| | | | 100 | | | | | 105 | | | | | 110 | | |
| Met | Phe | Gln | Gly | Thr | Pro | Arg | Gly | Asn | Gly | Thr | Phe | Met | Tyr | Glu | Lys |
| | | 115 | | | | | 120 | | | | | 125 | | | |
| Val | Gly | Ser | Val | Pro | Pro | Ser | Val | Asp | Trp | Arg | Lys | Asn | Gly | Ala | Val |
| | 130 | | | | | 135 | | | | | 140 | | | | |
| Thr | Gly | Val | Lys | Asp | Gln | Gly | Gln | Cys | Gly | Ser | Cys | Trp | Ala | Phe | Ser |
| 145 | | | | | 150 | | | | | 155 | | | | | 160 |
| Thr | Val | Trp | Ala | Val | Glu | Gly | Phe | Thr | Ile | Asn | Gln | Ile | Lys | Thr | Asn |
| | | | | 165 | | | | | 170 | | | | | 175 | |
| Lys | Leu | Val | Ser | Leu | Ser | Glu | Gln | Glu | Leu | Val | Asp | Cys | Asp | Thr | Lys |
| | | | 180 | | | | | 185 | | | | | 190 | | |
| Lys | Asn | Ala | Gly | Cys | Asn | Gly | Gly | Leu | Met | Glu | Ser | Ala | Phe | Glu | Phe |
| | | | 195 | | | | | 200 | | | | | 205 | | |
| Ile | Lys | Gln | Lys | Gly | Gly | Ile | Thr | Thr | Glu | Ser | Asn | Tyr | Pro | Tyr | Thr |
| | 210 | | | | | 215 | | | | | 220 | | | | |
| Ala | Gln | Asp | Gly | Phe | Thr | Thr | Cys | Asp | Ala | Ser | Lys | Ala | Asn | Asp | Leu |
| 225 | | | | | 230 | | | | | 235 | | | | | 240 |
| Ala | Val | Ser | Ile | Asp | Gly | His | Glu | Asn | Val | Pro | Ala | Asn | Asp | Glu | Asn |
| | | | | 245 | | | | | 250 | | | | | 255 | |
| Ala | Leu | Leu | Lys | Ala | Val | Ala | Asn | Gln | Pro | Val | Ser | Val | Ala | Ile | Asp |
| | | | 260 | | | | | 265 | | | | | 270 | | |
| Ala | Gly | Gly | Ser | Asp | Phe | Gln | Phe | Tyr | Ser | Glu | Gly | Val | Phe | Thr | Gly |
| | | | 275 | | | | | 280 | | | | | 285 | | |
| Asp | Phe | Thr | Cys | Ser | Thr | Glu | Leu | Asn | His | Gly | Val | Ala | Ile | Val | Gly |
| | | 290 | | | | | 295 | | | | | 300 | | | |
| Tyr | Gly | Thr | Thr | Val | Asp | Gly | Thr | Asn | Tyr | Trp | Thr | Val | Arg | Asn | Ser |
| 305 | | | | | 310 | | | | | 315 | | | | | 320 |
| Trp | Gly | Pro | Glu | Trp | Gly | Glu | Gln | Gly | Tyr | Ile | Arg | Met | Gln | Arg | Ser |
| | | | | 325 | | | | | 330 | | | | | 335 | |
| Ile | Ser | Lys | Lys | Glu | Gly | Leu | Cys | Gly | Ile | Ala | Met | Met | Ala | Phe | Thr |
| | | | 340 | | | | | 345 | | | | | 350 | | |
| Ser | Tyr | Pro | Ile | Lys | Asn | Ser | Ser | Asn | Pro | Thr | Gly | Pro | Ser | Ser | |
| | | 355 | | | | | 360 | | | | | 365 | | | |
| Ser | Pro | Lys | Asp | Glu | Leu | | | | | | | | | | |
| | 370 | | | | | | | | | | | | | | |

```
<210> SEQ ID NO 81
```

```
<211> LENGTH: 363
<212> TYPE: PRT
<213> ORGANISM: Glycine max

<400> SEQUENCE: 81

Met Ala Met Lys Lys Phe Leu Trp Val Val Leu Ser Leu Ser Leu Val
1               5                   10                  15

Leu Gly Val Ala Asn Ser Phe Asp Phe His Asp Lys Asp Leu Glu Ser
            20                  25                  30

Glu Glu Ser Leu Trp Asp Leu Tyr Glu Arg Trp Arg Ser His His Thr
        35                  40                  45

Val Ser Arg Ser Leu Gly Asp Lys His Lys Arg Phe Asn Val Phe Lys
    50                  55                  60

Ala Asn Met Met His Val His Asn Thr Asn Lys Met Asp Lys Pro Tyr
65                  70                  75                  80

Lys Leu Lys Leu Asn Lys Phe Ala Asp Met Thr Asn His Glu Phe Arg
                85                  90                  95

Ser Thr Tyr Ala Gly Ser Lys Val Asn His His Arg Met Phe Arg Asp
            100                 105                 110

Met Pro Arg Gly Asn Gly Thr Phe Met Tyr Glu Lys Val Gly Ser Val
        115                 120                 125

Pro Ala Ser Val Asp Trp Arg Lys Lys Gly Ala Val Thr Asp Val Lys
    130                 135                 140

Asp Gln Gly His Cys Gly Ser Cys Trp Ala Phe Ser Thr Val Val Ala
145                 150                 155                 160

Val Glu Gly Ile Asn Gln Ile Lys Thr Asn Lys Leu Val Ser Leu Ser
                165                 170                 175

Glu Gln Glu Leu Val Asp Cys Asp Thr Glu Glu Asn Ala Gly Cys Asn
            180                 185                 190

Gly Gly Leu Met Glu Ser Ala Phe Gln Phe Ile Lys Gln Lys Gly Gly
        195                 200                 205

Ile Thr Thr Glu Ser Tyr Tyr Pro Tyr Thr Ala Gln Asp Gly Thr Cys
    210                 215                 220

Asp Ala Ser Lys Ala Asn Asp Leu Ala Val Ser Ile Asp Gly His Glu
225                 230                 235                 240

Asn Val Pro Gly Asn Asp Glu Asn Ala Leu Leu Lys Ala Val Ala Asn
                245                 250                 255

Gln Pro Val Ser Val Ala Ile Asp Ala Asp Gly Ser Asp Phe Gln Phe
            260                 265                 270

Tyr Ser Glu Phe Val Phe Thr Gly Asp Cys Ser Thr Glu Leu Asn His
        275                 280                 285

Gly Val Ala Ile Val Gly Tyr Gly Ala Thr Val Asp Gly Thr Ser Tyr
    290                 295                 300

Trp Ile Val Arg Asn Ser Trp Gly Pro Glu Trp Gly Glu Leu Gly Tyr
305                 310                 315                 320

Ile Arg Met Gln Arg Asn Ile Ser Lys Lys Glu Gly Leu Cys Gly Ala
                325                 330                 335

Ile Ala Met Leu Ala Ser Tyr Pro Ile Lys Asn Ser Ser Asn Asn Pro
            340                 345                 350

Thr Gly Pro Ser Ser Ser Pro Lys Asp Glu Leu
        355                 360

<210> SEQ ID NO 82
<211> LENGTH: 389
<212> TYPE: PRT
<213> ORGANISM: Oryza sativa
```

<400> SEQUENCE: 82

```
Met Leu Arg Cys Phe Leu Val Ala Ala Ala Val Ala Leu Ala Ala
1               5                   10                  15

Ala Ala Ala Ala Pro Ala Arg Ala Ile Pro Phe Thr Glu Ser Asp Leu
            20                  25                  30

Ser Ser Glu Glu Ser Leu Arg Ala Leu Tyr Glu Arg Trp Arg Ser Arg
        35                  40                  45

Tyr Thr Val Ser Arg Pro Ala Ala Ser Gly Gly Val Gly Asn Asp Asp
    50                  55                  60

Gly Glu Ala Arg Arg Phe Asn Val Glu Val Glu Asn Ala Arg Tyr
65                  70                  75                  80

Ile His Glu Ala Asn Arg Arg Gly Gly Arg Pro Phe Arg Leu Ala Leu
                85                  90                  95

Asn Lys Phe Ala Asp Met Thr Thr Asp Glu Phe Arg Arg Thr Tyr Ala
            100                 105                 110

Gly Ser Arg Ala Arg His His Arg Ser Leu Ser Gly Arg Gly Gly
        115                 120                 125

Glu Gly Gly Ser Phe Gly Tyr Gly Gly Asp Asp Glu Asp Asn Leu Pro
    130                 135                 140

Pro Ala Val Asp Trp Arg Glu Arg Gly Ala Val Thr Gly Ile Lys Asp
145                 150                 155                 160

Gln Gly Gln Cys Gly Ser Cys Trp Ala Phe Ser Thr Val Ala Ala Val
                165                 170                 175

Glu Gly Val Asn Lys Ile Lys Thr Gly Arg Leu Val Thr Leu Ser Glu
            180                 185                 190

Gln Glu Leu Val Asp Cys Asp Thr Gly Asp Asn Gln Gly Cys Asp Gly
        195                 200                 205

Gly Leu Met Asp Tyr Ala Phe Gln Phe Ile Lys Arg Asn Gly Gly Ile
    210                 215                 220

Thr Thr Glu Ser Asn Tyr Pro Tyr Arg Ala Glu Gln Gly Arg Cys Asn
225                 230                 235                 240

Lys Ala Lys Ala Ser Ser His Asp Val Thr Ile Gly Gly Tyr Glu Asp
                245                 250                 255

Val Pro Ala Asn Asp Glu Ser Ala Leu Gln Lys Ala Val Ala Asn Gln
            260                 265                 270

Pro Val Ala Val Ala Val Glu Ala Ser Gly Gln Asp Phe Gln Phe Tyr
        275                 280                 285

Ser Glu Gly Val Phe Thr Gly Glu Cys Gly Thr Asp Leu Asp His Gly
    290                 295                 300

Val Ala Ala Val Gly Tyr Gly Ile Thr Arg Asp Gly Thr Lys Tyr Gly
305                 310                 315                 320

Ile Val Lys Asn Ser Trp Gly Glu Asp Trp Gly Glu Arg Gly Tyr Ile
                325                 330                 335

Arg Met Gln Arg Gly Val Ser Ser Asp Ser Asn Gly Leu Cys Gly Ile
            340                 345                 350

Ile Ala Met Glu Ala Ser Tyr Pro Val Lys Ser Gly Ala Arg Asn Ala
        355                 360                 365

Ala Ala Ser Asn Arg Val Val Lys Asp Glu Met Arg Tyr Glx Ala Ser
    370                 375                 380

Ala Thr Ile Val Ala
385
```

<210> SEQ ID NO 83

```
<211> LENGTH: 348
<212> TYPE: PRT
<213> ORGANISM: Helianthus annuus

<400> SEQUENCE: 83
```

| | | | | | | | | | | | | | | | |
|---|---|---|---|---|---|---|---|---|---|---|---|---|---|---|---|
| Met | Glu | Cys | Asn | Lys | Val | Phe | Val | Leu | Ser | Ile | Ser | Leu | Ala | Leu | Phe |
| 1 | | | | 5 | | | | | 10 | | | | | 15 | |
| Ile | Gly | Val | Val | Asn | Cys | Ile | Asp | Phe | Thr | Glu | Lys | Asp | Leu | Ala | Thr |
| | | | 20 | | | | | 25 | | | | | 30 | | |
| Asp | Lys | Ser | Leu | Trp | Asp | Leu | Tyr | Glu | Arg | Trp | Gly | Ser | Gln | His | Met |
| | | | 35 | | | | 40 | | | | | 45 | | | |
| Leu | Ser | Arg | Ala | Pro | Asp | Glu | Lys | Lys | Arg | Phe | Asn | Val | Phe | Lys | |
| | 50 | | | | | 55 | | | | | 60 | | | | |
| Tyr | Asn | Val | Asn | His | Ile | Asn | Arg | Val | Asn | Gln | Leu | Gly | Lys | Pro | Tyr |
| 65 | | | | | 70 | | | | | 75 | | | | | 80 |
| Lys | Leu | Lys | Leu | Asn | Glu | Phe | Ala | Asp | Met | Thr | Asn | His | Glu | Phe | Lys |
| | | | | 85 | | | | | 90 | | | | | 95 | |
| Ala | Gly | Phe | Asp | Ser | Lys | Ile | Leu | His | Phe | Arg | Met | Leu | Lys | Gly | Lys |
| | | | 100 | | | | | 105 | | | | | 110 | | |
| Arg | Arg | Gln | Thr | Pro | Phe | Thr | His | Ala | Lys | Thr | Thr | Asp | Pro | Pro | Pro |
| | | | 115 | | | | | 120 | | | | | 125 | | |
| Ser | Ile | Asp | Trp | Arg | Thr | Asn | Gly | Ala | Val | Asn | Pro | Ile | Lys | Asn | Gln |
| | 130 | | | | | 135 | | | | | 140 | | | | |
| Gly | Arg | Cys | Gly | Ser | Gly | Trp | Ala | Phe | Ser | Thr | Ile | Val | Gly | Val | Glu |
| 145 | | | | | 150 | | | | | 155 | | | | | 160 |
| Gly | Ile | Asn | Lys | Ile | Lys | Thr | Asn | Gln | Leu | Val | Ser | Leu | Ser | Glu | Gln |
| | | | | 165 | | | | | 170 | | | | | 175 | |
| Glu | Leu | Val | Asp | Cys | Glu | Thr | Asp | Cys | Glu | Gly | Cys | Asn | Gly | Gly | Leu |
| | | | 180 | | | | | 185 | | | | | 190 | | |
| Met | Glu | Asn | Gly | Tyr | Glu | Phe | Ile | Lys | Glu | Thr | Gly | Gly | Val | Thr | Thr |
| | | | 195 | | | | | 200 | | | | | 205 | | |
| Glu | Gln | Ile | Tyr | Pro | Tyr | Phe | Ala | Arg | Asn | Gly | Arg | Cys | Asp | Ile | Ser |
| | 210 | | | | | 215 | | | | | 220 | | | | |
| Lys | Arg | Asn | Ser | Pro | Val | Val | Lys | Ile | Asp | Gly | Phe | Glu | Asn | Val | Pro |
| 225 | | | | | 230 | | | | | 235 | | | | | 240 |
| Ala | Asn | Asp | Glu | Ser | Ala | Met | Leu | Arg | Ala | Val | Ala | Asn | Gln | Pro | Val |
| | | | | 245 | | | | | 250 | | | | | 255 | |
| Ser | Ile | Ala | Ile | Asp | Ala | Gly | Gly | Leu | Asn | Phe | Gln | Phe | Tyr | Ser | Gln |
| | | | 260 | | | | | 265 | | | | | 270 | | |
| Gly | Val | Phe | Asn | Gly | Ala | Cys | Gly | Thr | Glu | Leu | Asn | His | Gly | Val | Ala |
| | | | 275 | | | | | 280 | | | | | 285 | | |
| Ile | Val | Gly | Tyr | Gly | Thr | Thr | Gln | Asp | Gly | Thr | Asn | Tyr | Trp | Ile | Val |
| | | | | 290 | | | | | 295 | | | | | 300 | |
| Arg | Asn | Ser | Trp | Gly | Thr | Gly | Trp | Gly | Glu | Gly | Tyr | Val | Arg | Met | |
| 305 | | | | | 310 | | | | | 315 | | | | | 320 |
| Gln | Arg | Gly | Val | Asn | Val | Pro | Glu | Gly | Leu | Cys | Gly | Leu | Ala | Met | Asp |
| | | | | 325 | | | | | 330 | | | | | 335 | |
| Ala | Ser | Tyr | Pro | Ile | Lys | Ala | Ser | Ser | Val | Asn | Leu | | | | |
| | | | 340 | | | | | 345 | | | | | | | |

```
<210> SEQ ID NO 84
<211> LENGTH: 846
<212> TYPE: DNA
<213> ORGANISM: Artificial Sequence
<220> FEATURE:
<223> OTHER INFORMATION: Synthesized: CcCP-4 KDDL
<220> FEATURE:
```

```
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (818)..(818)
<223> OTHER INFORMATION: n is a, c, g, or t
<220> FEATURE:
<221> NAME/KEY: misc_feature
<222> LOCATION: (820)..(820)
<223> OTHER INFORMATION: n is a, c, g, or t

<400> SEQUENCE: 84
ggcaaatgtg gcagctgttg ggcattttca actgtggttg gagtcgaggg aatcaacaaa      60
atcaaaacag gccaattagt ttctctgtcc gagcaagaac ttgttgactg tgaaacggac     120
aatgaaggat gcaacggagg actcatggaa aatgcatacg agtttattaa gaaaagtggg     180
ggataacaa ctgagaggct atatccctac aaggcaagag atggcagctg tgattcatca      240
aagatgaatg cccctgctgt gaccattgat gggcatgaaa tggtacccgc aaacgatgag     300
aatgccttga tgaaagctgt tgctaaccag cctgtatcag tagctataga tgcgtctggc     360
tctgacatgc aattttattc agagggtgta tacactggag actcatgtgg caatgagctt     420
gatcatggcg tggcggtcgt cggctatgga actgctcttg acggtactaa atactggata     480
gtgaagaact catggggaac aggatgggga gaacagggct atatcaggat gcaacgtggt     540
gttgatgctg ctgaaggcgg agtttgtggg atagcaatgg aggcctccta tccacttaaa     600
ttgtcctccc acaatccaaa accatcccca cctaaggacg agctctagat tgatcctctt     660
atatatatac atacatatat atatatatat atatatttct gtagattcat tgaattttag     720
ttacagacta cgcgcttntg aagacttaga tcatctctag gcatagattt atgtaatcct     780
gctcctgtga tggtttgaat aaataataag tagtaccntn taaaaaaaaa aaaaaaaaaa     840
aaaaaa                                                                 846

<210> SEQ ID NO 85
<211> LENGTH: 1367
<212> TYPE: DNA
<213> ORGANISM: Artificial Sequence
<220> FEATURE:
<223> OTHER INFORMATION: Synthesized: CcCP-4 KDDL

<400> SEQUENCE: 85
ggcttacatc ttaaatcctg attttatag attcgccttt cgtgaagttc aatcttcgca      60
gtcgctcact aacatttggt agacatactt cgattatgaa aatggggaag gctttccttt     120
ttgccgttgt attggctgtg atcttagtgg cggctatgag catggagatc acagaaagag     180
atttggcttc tgaggaaagc ttgtgggact tgtacgaaag atggaggagc catcatactg     240
tttctcgaga cctttctgag aaacgaaagc gctttaatgt tttcaaggca aatgtccatc     300
acattcacaa ggtgaaccag aaggacaagc cttacaagct gaaactcaac agtttcgctg     360
atatgaccaa ccacgagttc agggaattct acagttctaa ggtgaaacat taccggatgc     420
tccacggcag tcgtgctaat actggattta tgcatgggaa gactgaaagt ttgccagcct     480
ccgttgattg gagaaagcaa ggagccgtga ctggcgtcaa gaatcaaggc aaatgtggta     540
gctgttgggc attttcaact gtggttggag tcgaggaat caacaaaatc aaaacaggcc      600
aattagtttc tctgtccgag caagaacttg ttgactgtga acggacaat gaaggatgca      660
acggaggact catggaaaat gcatacgagt ttattaagaa aagtggggga ataacaactg     720
agaggctata tccctacaag gcaagagatg gcagctgtga ttcgtcaaag atgaatgccc     780
```

```
ctgctgtgac tattgatggg catgaaatgg tacccgcaaa cgatgagaat gccttgatga   840
aagctgttgc taaccagcct gtatcagtag ctatagatgc gtctggctct gacatgcaat   900
tttattcaga gggtgtatac gctggagact cgtgtggcaa tgagcttgat catggcgtgg   960
cggtcgtcgg ctacgggact gctcttgacg gtactaaata ctggatagtg aagaactcat  1020
ggggaacagg atggggagaa cagggctata tcaggatgca acgtggtgtt gatgctgctg  1080
aaggcggagt tgtgggata gcaatggagg cctcctatcc acttaaattg tcctcccaca  1140
atccaaaacc atccccacct aaggacgacc tctagattga tcctcttata tatatacata  1200
tatatatata tttcagtaga ttcattgaat tttagttaca gactacgcgc ttctgaagac  1260
ttagatcatc tctaggcata gatttatgta atcctgctcc tgtgatggtt tgaataaaca  1320
ataagtagta ctaataaaaa aaaaaaaaaa aaaaaaaaaa aaaaaaa             1367
```

<210> SEQ ID NO 86
<211> LENGTH: 359
<212> TYPE: PRT
<213> ORGANISM: Artificial Sequence
<220> FEATURE:
<223> OTHER INFORMATION: Synthesized: CcCp-4 KDDL

<400> SEQUENCE: 86

```
Met Lys Met Gly Lys Ala Phe Leu Phe Ala Val Val Leu Ala Val Ile
1               5                   10                  15

Leu Val Ala Ala Met Ser Met Glu Ile Thr Glu Arg Asp Leu Ala Ser
            20                  25                  30

Glu Glu Ser Leu Trp Asp Leu Tyr Glu Arg Trp Arg Ser His His Thr
        35                  40                  45

Val Ser Arg Asp Leu Ser Glu Lys Arg Lys Arg Phe Asn Val Phe Lys
    50                  55                  60

Ala Asn Val His His Ile His Lys Val Asn Gln Lys Asp Lys Pro Tyr
65                  70                  75                  80

Lys Leu Lys Leu Asn Ser Phe Ala Asp Met Thr Asn His Glu Phe Arg
                85                  90                  95

Glu Phe Tyr Ser Ser Lys Val Lys His Tyr Arg Met Leu His Gly Ser
            100                 105                 110

Arg Ala Asn Thr Gly Phe Met His Gly Lys Thr Glu Ser Leu Pro Ala
        115                 120                 125

Ser Val Asp Trp Arg Lys Gln Gly Ala Val Thr Gly Val Lys Asn Gln
    130                 135                 140

Gly Lys Cys Gly Ser Cys Trp Ala Phe Ser Thr Val Val Gly Val Glu
145                 150                 155                 160

Gly Ile Asn Lys Ile Lys Thr Gly Gln Leu Val Ser Leu Ser Glu Gln
                165                 170                 175

Glu Leu Val Asp Cys Glu Thr Asp Asn Glu Gly Cys Asn Gly Gly Leu
            180                 185                 190

Met Glu Asn Ala Tyr Glu Phe Ile Lys Lys Ser Gly Gly Ile Thr Thr
        195                 200                 205

Glu Arg Leu Tyr Pro Tyr Lys Ala Arg Asp Gly Ser Cys Asp Ser Ser
    210                 215                 220

Lys Met Asn Ala Pro Ala Val Thr Ile Asp Gly His Glu Met Val Pro
225                 230                 235                 240

Ala Asn Asp Glu Asn Ala Leu Met Lys Ala Val Ala Asn Gln Pro Val
                245                 250                 255

Ser Val Ala Ile Asp Ala Ser Gly Ser Asp Met Gln Phe Tyr Ser Glu
            260                 265                 270
```

-continued

```
Gly Val Tyr Ala Gly Asp Ser Cys Gly Asn Glu Leu Asp His Gly Val
            275                 280                 285
Ala Val Val Gly Tyr Gly Thr Ala Leu Asp Gly Thr Lys Tyr Trp Ile
            290                 295                 300
Val Lys Asn Ser Trp Gly Thr Gly Trp Gly Glu Gln Gly Tyr Ile Arg
305                 310                 315                 320
Met Gln Arg Gly Val Asp Ala Ala Glu Gly Gly Val Cys Gly Ile Ala
            325                 330                 335
Met Glu Ala Ser Tyr Pro Leu Lys Leu Ser Ser His Asn Pro Lys Pro
            340                 345                 350
Ser Pro Pro Lys Asp Asp Leu
            355

<210> SEQ ID NO 87
<211> LENGTH: 215
<212> TYPE: PRT
<213> ORGANISM: Artificial Sequence
<220> FEATURE:
<223> OTHER INFORMATION: Synthesized: CcCP-4 KDEL

<400> SEQUENCE: 87

Gly Lys Cys Gly Ser Cys Trp Ala Phe Ser Thr Val Val Gly Val Glu
1               5                   10                  15
Gly Ile Asn Lys Ile Lys Thr Gly Gln Leu Val Ser Leu Ser Glu Gln
            20                  25                  30
Glu Leu Val Asp Cys Glu Thr Asp Asn Glu Gly Cys Asn Gly Gly Leu
        35                  40                  45
Met Glu Asn Ala Tyr Glu Phe Ile Lys Lys Ser Gly Gly Ile Thr Thr
    50                  55                  60
Glu Arg Leu Tyr Pro Tyr Lys Ala Arg Asp Gly Ser Cys Asp Ser Ser
65                  70                  75                  80
Lys Met Asn Ala Pro Ala Val Thr Ile Asp Gly His Glu Met Val Pro
                85                  90                  95
Ala Asn Asp Glu Asn Ala Leu Met Lys Ala Val Ala Asn Gln Pro Val
            100                 105                 110
Ser Val Ala Ile Asp Ala Ser Gly Ser Asp Met Gln Phe Tyr Ser Glu
        115                 120                 125
Gly Val Tyr Thr Gly Asp Ser Cys Gly Asn Glu Leu Asp His Gly Val
    130                 135                 140
Ala Val Val Gly Tyr Gly Thr Ala Leu Asp Gly Thr Lys Tyr Trp Ile
145                 150                 155                 160
Val Lys Asn Ser Trp Gly Thr Gly Trp Gly Glu Gln Gly Tyr Ile Arg
                165                 170                 175
Met Gln Arg Gly Val Asp Ala Ala Glu Gly Gly Val Cys Gly Ile Ala
            180                 185                 190
Met Glu Ala Ser Tyr Pro Leu Lys Leu Ser Ser His Asn Pro Lys Pro
        195                 200                 205
Ser Pro Pro Lys Asp Glu Leu
    210                 215

<210> SEQ ID NO 88
<211> LENGTH: 430
<212> TYPE: PRT
<213> ORGANISM: Coffea arabica
<220> FEATURE:
<221> NAME/KEY: misc_feature
<222> LOCATION: (308)..(308)
<223> OTHER INFORMATION: Xaa can be any naturally occurring amino acid
```

<400> SEQUENCE: 88

```
Met Leu Ala Ala Leu Asp Met Pro Leu Gly Gly Asn Gly Ser Pro Thr
1               5                   10                  15

Asp Ala Ala Leu Tyr Phe Thr Lys Leu Ser Ile Gly Thr Pro Pro Gln
            20                  25                  30

Asp Tyr Tyr Val Gln Val Asp Thr Gly Ser Asp Ile Ile Trp Val Asn
        35                  40                  45

Cys Ala Gly Cys Val Arg Cys Pro Lys Lys Ser Ser Leu Gly Ile Asp
50                  55                  60

Ile Thr Leu Tyr Asp Met Lys Ala Ser Ser Thr Gly Arg Leu Val Thr
65                  70                  75                  80

Cys Asp Gln Asp Phe Cys Leu Ser Ala Ile Asn Ala Pro Ala Ser Asp
                85                  90                  95

Cys Lys Val Gly Asn Pro Cys Ala Tyr Ser Val Thr Tyr Gly Asp Gly
            100                 105                 110

Ser Ser Thr Gly Gly Tyr Ile Val Arg Asp Tyr Ala Lys Leu Asn Gln
        115                 120                 125

Leu Thr Gly Asn Leu Gln Thr Ile Pro Met Asn Gly Ser Leu Val Phe
130                 135                 140

Gly Cys Ser Ser Gln Gln Ser Gly Glu Leu Gly Ser Ser Thr Glu Ala
145                 150                 155                 160

Val Asp Gly Ile Ile Gly Phe Gly Gln Ala Asn Ser Ser Ile Ile Ser
                165                 170                 175

Gln Leu Ala Ser Ala Gly Lys Val Lys Lys Ile Phe Ser His Cys Leu
            180                 185                 190

Asp Gly Ile Asn Gly Gly Ile Phe Ala Ile Gly Gln Val Val Gln
        195                 200                 205

Pro Lys Leu Lys Thr Thr Pro Leu Val Pro Asn Glu Ala His Tyr Asn
210                 215                 220

Val Val Leu Asn Ala Ile Glu Val Gly Gly Asp Val Leu Asn Leu Pro
225                 230                 235                 240

Ser Asp Val Leu Gly Gly Ser Gly Ser Gly Thr Ile Ile Asp Ser
                245                 250                 255

Gly Thr Ile Leu Ala Tyr Leu Pro Asp Asp Val Tyr Thr Pro Leu Met
            260                 265                 270

Leu Lys Ile Thr Ala Ser Gln Ser Asn Leu Lys Ile His Ile Val Glu
        275                 280                 285

Asn Gln Phe Lys Cys Thr Val Tyr Ser Gly Asn Val Asp Asp Gly Phe
290                 295                 300

Pro Val Val Xaa Phe His Phe Glu Asp Ser Leu Ser Leu Thr Val Val
305                 310                 315                 320

Pro His Glu Tyr Leu Phe Asp Leu His Asp Asp Gln Trp Cys Ile Gly
                325                 330                 335

Trp Gln Asn Lys Gly Met Gln Thr Arg Asp Gly Arg Glu Val Thr Leu
            340                 345                 350

Leu Gly Asp Leu Val Leu Ala Asn Lys Leu Val Ser Tyr Asp Ile Glu
        355                 360                 365

Asn Gln Thr Ile Gly Trp Ala Glu Tyr Asn Cys Ser Ser Ser Ile Lys
370                 375                 380

Leu Arg Asp Glu Lys Ser Gly Asn Val Tyr Ala Val Gly Ser Glu Ile
385                 390                 395                 400

Ile Ser Ser Ala Arg Gly Leu Asn Ala Gly Lys Ala Leu Arg Phe Leu
                405                 410                 415
```

```
Leu Ile Ile Ile Thr Ser Leu Leu His Ala Leu Leu Ile Pro
            420                 425                 430
```

<210> SEQ ID NO 89
<211> LENGTH: 320
<212> TYPE: PRT
<213> ORGANISM: Arabidopsis thaliana

<400> SEQUENCE: 89

```
Met Tyr Gly Asp Gly Ser Ser Thr Asn Gly Tyr Leu Val Lys Asp Val
1               5                   10                  15

Val His Leu Asp Leu Val Thr Gly Asn Arg Gln Thr Gly Ser Thr Asn
            20                  25                  30

Gly Thr Ile Ile Phe Gly Cys Gly Ser Lys Gln Ser Gly Gln Leu Gly
            35                  40                  45

Glu Ser Gln Ala Ala Val Asp Gly Ile Met Gly Phe Gly Gln Ser Asn
    50                  55                  60

Ser Ser Phe Ile Ser Gln Leu Ala Ser Gln Gly Lys Val Lys Arg Ser
65                  70                  75                  80

Phe Ala His Cys Leu Asp Asn Asn Gly Gly Ile Phe Ala Ile
                85                  90                  95

Gly Glu Val Val Ser Pro Lys Val Lys Thr Thr Pro Met Leu Ser Lys
            100                 105                 110

Ser Ala His Tyr Ser Val Asn Leu Asn Ala Ile Glu Val Gly Asn Ser
            115                 120                 125

Val Leu Glu Leu Ser Ser Asn Ala Phe Asp Ser Asp Asp Lys Gly
        130                 135                 140

Val Ile Ile Asp Ser Gly Thr Thr Leu Val Tyr Leu Pro Asp Ala Val
145                 150                 155                 160

Tyr Asn Pro Leu Leu Asn Glu Ile Leu Ala Ser His Pro Glu Leu Thr
                165                 170                 175

Leu Glu Thr Val Gln Glu Ser Phe Thr Cys Phe His Tyr Ile Asp Lys
            180                 185                 190

Leu Asp Arg Phe Pro Thr Val Thr Phe Gln Phe Asp Lys Ser Val Ser
            195                 200                 205

Leu Ala Val Tyr Pro Arg Glu Tyr Leu Phe Gln Val Arg Glu Asp Thr
        210                 215                 220

Trp Cys Phe Gly Trp Gln Asn Gly Leu Gln Thr Lys Gly Gly Ala
225                 230                 235                 240

Ser Leu Thr Ile Leu Gly Asp Met Ala Leu Ser Asn Lys Leu Val Val
                245                 250                 255

Tyr Asp Ile Phe Asn Gln Val Ile Gly Trp Thr Asn His Asn Cys Ser
            260                 265                 270

Gly Gly Ile Gln Val Arg Asp Glu Glu Ser Gly Ala Ile Tyr Thr Val
        275                 280                 285

Gly Ala Glu Asn Leu Ser Trp Ser Ser Ser Leu Ala Ile Thr Lys Leu
    290                 295                 300

Leu Thr Leu Val Ser Leu Leu Ile Pro Phe Thr Cys Asn Val Ala Leu
305                 310                 315                 320
```

<210> SEQ ID NO 90
<211> LENGTH: 478
<212> TYPE: PRT
<213> ORGANISM: Arabidopsis thaliana

<400> SEQUENCE: 90

```
Met Asp Pro Ser Arg Ile Ser Arg Ile Val Ala Val Phe Val Leu
1               5                   10                  15

Val Ile Gln Val Val Ser Gly Asn Phe Val Phe Asn Val Thr His Lys
            20                  25                  30

Phe Ala Gly Lys Glu Lys Gln Leu Ser Glu Leu Lys Ser His Asp Ser
        35                  40                  45

Phe Arg His Ala Arg Met Leu Ala Asn Ile Asp Met Pro Leu Gly Gly
    50                  55                  60

Asn Gly Ser Pro Thr Asp Ala Ala Leu Tyr Phe Thr Lys Leu Ser Ile
65              70                  75                  80

Gly Ser Pro Pro Lys Glu Tyr Tyr Val Gln Val Asp Thr Gly Ser Asp
            85                  90                  95

Ile Ile Trp Val Asn Cys Ala Pro Cys Pro Lys Cys Pro Val Lys Thr
                100                 105                 110

Asp Leu Gly Ile Pro Leu Ser Leu Tyr Asp Ser Lys Thr Ser Ser Thr
            115                 120                 125

Ser Lys Asn Val Gly Cys Glu Asp Phe Cys Ser Ile Ile Met Gln
    130                 135                 140

Ser Glu Thr Cys Gly Ala Lys Lys Pro Cys Ser Tyr His Val Val Tyr
145                 150                 155                 160

Gly Asp Gly Ser Thr Ser Asp Gly Asp Phe Ile Lys Asp Asn Ile Thr
                165                 170                 175

Leu Glu Gln Val Thr Gly Asn Leu Arg Thr Ala Pro Leu Ala Gln Glu
            180                 185                 190

Val Val Phe Gly Cys Gly Lys Asn Gln Ser Gly Gln Leu Gly Gln Thr
        195                 200                 205

Asp Ser Ala Val Asp Gly Ile Met Gly Phe Gly Gln Ser Asn Thr Ser
210                 215                 220

Ile Ile Ser Gln Leu Ala Ala Gly Ser Thr Lys Arg Ile Phe Ser
225                 230                 235                 240

His Cys Leu Asp Asn Asn Asn Gly Gly Gly Ile Phe Ala Val Gly Glu
                245                 250                 255

Val Glu Ser Pro Val Val Lys Thr Thr Pro Ile Val Pro Asn Gln Val
            260                 265                 270

His Tyr Asn Val Ile Leu Lys Gly Met Asp Val Asp Gly Asp Pro Ile
    275                 280                 285

Asp Leu Pro Pro Ser Leu Ala Ser Thr Asn Gly Asp Gly Thr Ile
    290                 295                 300

Ile Asp Ser Gly Thr Thr Leu Ala Tyr Leu Pro Gln Asn Leu Tyr Asn
305                 310                 315                 320

Ser Leu Ile Leu Lys Ile Thr Ala Lys Gln Gln Val Lys Leu Glu Met
            325                 330                 335

Val Gln Glu Thr Phe Ala Cys Phe Ser Phe Thr Ser Asn Thr Asp Lys
            340                 345                 350

Ala Phe Pro Val Val Asn Leu Glu Phe Glu Asp Ser Leu Lys Leu Ser
        355                 360                 365

Val Tyr Pro His Asp Tyr Leu Phe Ser Leu Lys Leu Asp Met Tyr Cys
    370                 375                 380

Phe Gly Trp Gln Ser Gly Gly Met Thr Ile Gln Asp Gly Ala Asp Val
385                 390                 395                 400

Ile Leu Leu Gly Asp Leu Val Leu Ser Asn Lys Leu Val Val Tyr Asp
                405                 410                 415

Leu Glu Asn Glu Val Ile Gly Trp Ala Asp His Asn Cys Ser Ser Ser
            420                 425                 430
```

```
Ile Lys Val Arg Asp Gly Ser Gly Ala Ala Tyr Gln Leu Gly Ala Glu
        435                 440                 445

Asn Leu Ile Ser Ala Ala Ser Ser Val Met Asn Gly Thr Leu Val Thr
        450                 455                 460

Leu Leu Ser Ile Leu Ile Trp Val Phe His Ser Phe Thr Ser
465                 470                 475

<210> SEQ ID NO 91
<211> LENGTH: 507
<212> TYPE: PRT
<213> ORGANISM: Coffea arabica

<400> SEQUENCE: 91

Met Glu Arg Arg Tyr Leu Trp Ala Ala Phe Val Leu Gly Ala Ile Val
1               5                   10                  15

Cys Ser Leu Phe Pro Leu Pro Ser Glu Gly Leu Lys Arg Ile Ser Leu
            20                  25                  30

Lys Lys Lys Pro Leu Asp Ile Gln Ser Ile Arg Ala Ala Lys Leu Ala
        35                  40                  45

His Leu Glu Ser Thr His Gly Ala Gly Arg Lys Glu Met Asp Asn Asn
    50                  55                  60

Leu Gly Ser Ser Asn Glu Asp Ile Leu Pro Leu Lys Asn Tyr Leu Asp
65                  70                  75                  80

Ala Gln Tyr Tyr Gly Glu Ile Gly Ile Gly Thr Pro Pro Gln Lys Phe
                85                  90                  95

Thr Val Ile Phe Asp Thr Gly Ser Ser Asn Leu Trp Val Pro Ser Ala
            100                 105                 110

Lys Cys Tyr Phe Ser Ile Ala Cys Trp Leu His Ser Lys Tyr Lys Ala
        115                 120                 125

Lys Lys Ser Ser Thr Tyr Thr Ala Ile Gly Lys Ser Cys Ser Ile Arg
    130                 135                 140

Tyr Gly Ser Gly Ser Ile Ser Gly Phe Ser Ser Gln Asp Asn Val Glu
145                 150                 155                 160

Val Gly Asp Leu Val Val Lys Asp Gln Val Phe Ile Glu Ala Ser Arg
                165                 170                 175

Glu Gly Ser Leu Thr Phe Val Ile Ala Lys Phe Asp Gly Ile Lys Gly
            180                 185                 190

Lys Gly Phe Gly Glu Asp Ala Val Asp Asn Met Val Pro Val Trp Tyr
        195                 200                 205

Asn Met Val Asp Gln Gly Leu Val Asp Phe Gln Val Phe Ser Phe Trp
    210                 215                 220

Leu Asn Arg Asp Pro Asn Ala Glu Asp Gly Gly Glu Leu Val Glu Gly
225                 230                 235                 240

Gly Val Asp Thr Asn His Phe Lys Gly Lys His Thr Tyr Val Pro Val
                245                 250                 255

Thr Gln Lys Gly Tyr Trp Gln Phe Lys Met Gly Asp Phe Leu Ile Gly
            260                 265                 270

Asn Val Ser Thr Gly Phe Cys Glu Gly Gly Cys Ala Ala Ile Val Asp
        275                 280                 285

Ser Gly Thr Ser Leu Leu Ala Gly Phe Thr Thr Val Thr Gln Ile
    290                 295                 300

Asn His Ala Ile Cys Ala Glu Gly Val Val Ser Thr Glu Cys Lys Glu
305                 310                 315                 320

Ile Val Ser Gln Tyr Gly Glu Leu Ile Trp Asp Ile Ile Val Ser Gly
                325                 330                 335
```

```
Val Leu Phe Asp Arg Val Cys Lys Gln Ala Gly Leu Cys Pro Leu Arg
                340                 345                 350

Gly Ala Gln Asn Glu Asn Ala Tyr Ile Lys Ser Val Val Asp Glu Glu
            355                 360                 365

Asn Lys Glu Glu Ala Ser Val Gly Glu Ser Phe Met Cys Thr Ala Cys
370                 375                 380

Glu Met Ala Val Val Trp Met Gln Asn Gln Leu Lys Gln Gln Gly Thr
385                 390                 395                 400

Lys Glu Lys Val Leu Ala Tyr Val Asn Gln Leu Cys Glu Ser Ile Pro
                405                 410                 415

Ser Pro Met Gly Glu Ser Ile Ile Asp Cys Asn Ser Leu Ser Thr Leu
                420                 425                 430

Pro Asn Val Ser Phe Thr Ile Gly Gly Lys Ser Phe Glu Leu Thr Leu
                435                 440                 445

Lys Glu Tyr Val Leu Arg Thr Gly Glu Gly Phe Ala Glu Val Cys Ile
450                 455                 460

Ser Gly Phe Met Ala Met Asp Val Pro Pro Arg Gly Pro Ile Trp
465                 470                 475                 480

Val Leu Gly Asp Val Phe Met Gly Val Tyr His Thr Val Phe Asp Tyr
                485                 490                 495

Gly Asn Leu Arg Met Gly Phe Ala Arg Ala Ala
                500                 505

<210> SEQ ID NO 92
<211> LENGTH: 508
<212> TYPE: PRT
<213> ORGANISM: Glycine max

<400> SEQUENCE: 92

Met Gly Gln Lys His Leu Val Thr Val Phe Cys Leu Trp Ala Leu Thr
1               5                   10                  15

Cys Ser Leu Leu Pro Ser Phe Ser Phe Gly Ile Leu Arg Ile Gly Leu
                20                  25                  30

Lys Lys Arg Pro Leu Asp Leu Asp Ser Ile Asn Ala Ala Arg Lys Ala
            35                  40                  45

Arg Glu Gly Leu Arg Ser Val Arg Pro Met Met Gly Ala His Asp Gln
50                  55                  60

Phe Ile Gly Lys Ser Lys Gly Glu Asp Ile Val Pro Leu Lys Asn Tyr
65                  70                  75                  80

Leu Asp Ala Gln Tyr Phe Gly Glu Ile Gly Ile Gly Ile Pro Pro Gln
                85                  90                  95

Pro Phe Thr Val Val Phe Asp Thr Gly Ser Ser Asn Leu Trp Val Pro
                100                 105                 110

Ser Ser Lys Cys Tyr Phe Thr Leu Ala Cys Tyr Thr His Asn Trp Tyr
                115                 120                 125

Thr Ala Lys Lys Ser Lys Thr His Val Asn Asn Gly Thr Ser Cys Lys
            130                 135                 140

Ile Asn Tyr Gly Thr Gly Ser Ile Ser Gly Phe Glu Ser Gln Asp Asn
145                 150                 155                 160

Val Lys Val Gly Ser Ala Val Val Lys His Gln Asp Phe Ile Glu Ala
                165                 170                 175

Thr His Glu Gly Ser Ile Thr Phe Leu Ser Ala Lys Phe Asp Gly Ile
            180                 185                 190

Leu Gly Leu Gly Phe Gln Glu Ile Ser Val Glu Asn Ala Val Pro Val
                195                 200                 205
```

Trp Phe Lys Met Val Glu Gln Lys Leu Ile Ser Glu Lys Val Phe Ser
    210                 215                 220

Phe Trp Leu Asn Gly Asp Pro Asn Ala Asn Lys Gly Gly Glu Leu Val
225                 230                 235                 240

Phe Gly Gly Val Asp Phe Lys His Phe Lys Gly Asn His Thr Tyr Val
                245                 250                 255

Pro Ile Thr Glu Lys Gly Tyr Trp Gln Ile Glu Met Gly Asp Phe Phe
            260                 265                 270

Val Gly Gly Val Ser Thr Gly Val Cys Glu Gly Gly Cys Ala Ala Ile
        275                 280                 285

Val Asp Ser Gly Thr Ser Leu Leu Ala Gly Phe Thr Pro Val Val Ala
    290                 295                 300

Phe Ile Asn His Ala Thr Gly Ala Glu Gly Val Leu Ser Val Glu Cys
305                 310                 315                 320

Lys Glu Val Val Ser Gln Tyr Gly Glu Leu Ile Trp Asp Leu Leu Val
                325                 330                 335

Ser Gly Val Lys Pro Asp Asp Ile Cys Ser Gln Val Gly Leu Cys Ser
            340                 345                 350

Ser Lys Arg His Gln Ser Lys Ser Ala Gly Ile Glu Met Val Thr Glu
        355                 360                 365

Lys Glu Gln Glu Glu Leu Ala Ala Arg Asp Thr Pro Leu Cys Ser Ser
    370                 375                 380

Cys Gln Met Leu Val Leu Trp Ile Gln Asn Gln Leu Lys Gln Lys Ala
385                 390                 395                 400

Thr Lys Asp Arg Val Phe Asn Tyr Val Asn Gln Ile Cys Glu Ser Ile
                405                 410                 415

Pro Ser Pro Ser Gly Glu Ser Val Ile Ser Cys Asn Ser Leu Ser Lys
            420                 425                 430

Met Phe Asn Ile Thr Phe Thr Ile Gly Asn Lys Pro Phe Val Leu Thr
        435                 440                 445

Pro Glu Gln Tyr Ile Leu Arg Thr Gly Glu Gly Ile Thr Cys Val Cys
    450                 455                 460

Leu Ser Gly Phe Ile Ala Phe Asp Val Pro Pro Lys Gly Phe Leu
465                 470                 475                 480

Trp Ile Leu Gly Asp Val Phe Met Arg Ala Tyr His Thr Val Phe Asp
                485                 490                 495

Tyr Gly Asn Leu Gln Val Gly Phe Ala Glu Ala Val
            500                 505

<210> SEQ ID NO 93
<211> LENGTH: 503
<212> TYPE: PRT
<213> ORGANISM: Ipomoea batatas

<400> SEQUENCE: 93

Met Gly Arg Lys Tyr Leu Cys Asn Ala Phe Leu Leu Trp Ala Val Val
1               5                   10                  15

Cys Thr Ala Leu Pro Ala Ala Tyr Ser Asp Asn Asn Leu Leu Arg Val
            20                  25                  30

Gly Leu Lys Lys Arg Pro Leu Asp Leu Glu Ser Ile Lys Ala Ala Lys
        35                  40                  45

Gly Ala Arg Leu Gly Gly Lys Tyr Gly Lys Val Asn Lys Lys Leu
    50                  55                  60

Gly Asp Ser Asp Glu Gly Ile Val Ser Leu Asn Asn Tyr Leu Asp Ala
65                  70                  75                  80

```
Gln Tyr Tyr Gly Glu Ile Ser Ile Gly Ser Pro Pro Asp Asn Phe Thr
                85                  90                  95
Val Ile Phe Asp Thr Gly Ser Ser Asn Leu Trp Val Phe Ser Ser Lys
            100                 105                 110
Cys Tyr Leu Ser Ile Ala Cys Tyr Phe His Ser Lys Tyr Lys Ser Ser
            115                 120                 125
Lys Ser Ser Thr Tyr Thr Gln Ile Gly Lys Ser Cys Ser Ile Thr Tyr
130                 135                 140
Gly Ser Val Ser Thr Ser Gly Phe Leu Ser Gln Asp Val Gln Leu
145                 150                 155                 160
Gly Asp Leu Leu Val Lys Asp Gln Val Phe Ile Glu Thr Thr Arg Glu
                165                 170                 175
Pro Ser Leu Thr Phe Ile Ile Ala Lys Phe Asp Gly Ile Leu Gly Leu
            180                 185                 190
Gly Phe Glu Ile Ser Val Glu Asn Val Val Pro Val Trp Tyr Asn Met
            195                 200                 205
Val Glu Gln Gly Leu Val Asp Glu Pro Val Phe Ser Phe Trp Leu Asn
210                 215                 220
Arg Asp Asp Lys Ala Glu Val Gly Gly Glu Leu Val Phe Gly Gly Val
225                 230                 235                 240
Asp Pro Lys His Phe Lys Gly Glu His Thr Tyr Val Pro Val Thr Gln
                245                 250                 255
Lys Gly Tyr Trp Gln Ile Asp Leu Gly Asp Phe Leu Ile Gly Asn Ser
            260                 265                 270
Ser Thr Gly Tyr Cys Glu Gly Cys Ala Val Ile Val Asp Ser Gly
            275                 280                 285
Thr Ser Leu Leu Thr Gly Pro Thr Ala Val Val Thr Glu Ile Asn Tyr
290                 295                 300
Ala Ile Gly Pro Glu Gly Val Val Cys Ala Glu Cys Lys Glu Val Val
305                 310                 315                 320
Ser Glu Tyr Gly Glu Met Ile Trp Asp Leu Leu Val Ser Gly Leu Arg
                325                 330                 335
Ala Asp Asp Val Cys Ser Glu Leu Gly Leu Cys Phe Leu Asn Gly Ala
            340                 345                 350
Trp His Glu Ser Ser Ile Ile Lys Thr Val Val Glu Lys Glu Ala Glu
            355                 360                 365
Gly Asn Leu Thr Ser Asn Pro Leu Cys Thr Thr Cys Glu Met Ala Val
370                 375                 380
Ile Trp Leu Gln Asn Gln Leu Lys Gln Lys Gly Ile Asn Glu Lys Val
385                 390                 395                 400
Phe Glu Tyr Val Asp Gln Leu Cys Glu Lys Leu Pro Ser Pro Asp Gly
                405                 410                 415
Glu Ser Val Ile Asp Cys Asn Ser Ile Ser Ser Met Pro Asn Val Thr
            420                 425                 430
Phe Val Ile Gly Asp Lys Asp Phe Val Leu Thr Pro Glu Gln Tyr Ile
            435                 440                 445
Leu Lys Thr Gly Glu Gly Ile Ala Ala Val Cys Val Ser Gly Phe Leu
450                 455                 460
Ala Leu Asp Val Pro Pro Gln Gly Pro Leu Trp Ile Leu Gly Asp
465                 470                 475                 480
Val Phe Met Gly Ala Tyr His Thr Val Phe Asp Tyr Gly Asn Leu Gln
                485                 490                 495
Val Gly Phe Ala Glu Ala Ala
```

500

<210> SEQ ID NO 94
<211> LENGTH: 506
<212> TYPE: PRT
<213> ORGANISM: Lycopersicon esculentum

<400> SEQUENCE: 94

Met Asp Lys Lys His Leu Cys Ala Ala Leu Leu Trp Ala Ile Ala
1               5                   10                  15

Cys Ser Ala Ile Pro Ala Ser Ser Gly Asp Leu Phe Arg Ile Gly Leu
            20                  25                  30

Lys Lys His Arg Leu Asp Val Asp Ser Ile Lys Ala Ala Arg Val Ala
        35                  40                  45

Lys Leu Gln Asp Arg Tyr Gly Lys His Val Asn Gly Ile Glu Lys Lys
    50                  55                  60

Ser Ser Asp Ser Asp Ile Tyr Lys Val Pro Leu Lys Asn Tyr Leu Asp
65                  70                  75                  80

Ala Gln Tyr Tyr Gly Glu Ile Cys Ile Gly Ser Pro Pro Gln Lys Phe
                85                  90                  95

Lys Val Ile Phe Asp Thr Gly Ser Ser Asn Leu Trp Val Pro Ser Ser
            100                 105                 110

Lys Cys Tyr Phe Ser Thr Ala Cys Trp Ile His Ser Lys Tyr Gln Ala
        115                 120                 125

Ser Lys Ser Ser Thr Tyr Thr Arg Asp Gly Glu Ser Cys Ser Ile Arg
    130                 135                 140

Tyr Gly Thr Gly Ser Ile Ser Gly His Phe Ser Met Asp Asn Val Gln
145                 150                 155                 160

Val Gly Asp Leu Val Val Lys Asp Gln Val Phe Ile Glu Ala Thr Arg
                165                 170                 175

Glu Pro Ser Ile Thr Phe Ile Val Ala Arg Phe Asp Cys Ile Leu Gly
            180                 185                 190

Leu Gly Phe Gln Glu Ile Ser Val Gly Asn Thr Thr Pro Val Trp Tyr
        195                 200                 205

Asn Met Val Gly Gln Gly Leu Val Lys Glu Pro Val Phe Ser Phe Trp
210                 215                 220

Glu Asn Arg Asp Ala Asn Ala Lys Glu Gly Gly Glu Leu Val Phe Gly
225                 230                 235                 240

Gly Val Asp Pro Lys His Glu Lys Gly Asn His Thr Cys Val Pro Leu
                245                 250                 255

Thr Gln Lys Gly Tyr Trp Gln Phe Asn Met Gly Asp Phe Leu Ile Gly
            260                 265                 270

Asn Thr Ser Thr Gly Tyr Cys Ala Gly Gly Cys Ala Ala Ile Val Asp
        275                 280                 285

Ser Gly Thr Ser Leu Leu Ala Gly Pro Thr Thr Ile Val Thr Gln Ile
    290                 295                 300

Asn His Ala Ile Gly Ala Glu Gly Ile Val Ser Met Glu Cys Lys Thr
305                 310                 315                 320

Ile Val Ser Gln Tyr Gly Glu Met Ile Trp Asp Leu Leu Val Ser Gly
                325                 330                 335

Ile Arg Phe Asp Gln Val Cys Ser Gln Ala Gly Ile Cys Phe Leu Asp
            340                 345                 350

Gly Ser Gln His Val Ser Ser Asn Ile Arg Thr Val Val Glu Arg Glu
        355                 360                 365

Thr Glu Gly Ser Ser Val Gly Glu Ala Pro Leu Cys Thr Ala Cys Glu

-continued

```
                370                 375                 380
Met Ala Val Val Trp Met Gln Asn Gln Leu Lys Gln Glu Gln Thr Lys
385                 390                 395                 400

Glu Lys Val Leu Glu Tyr Val Asn Gln Leu Cys Glu Lys Ile Pro Ser
                405                 410                 415

Pro Met Gly Glu Ser Ala Ile Asp Cys Asn Arg Ile Ser Ser Met Pro
                420                 425                 430

Asp Ile Thr Phe Thr Ile Lys Asp Thr Ala Phe Val Leu Thr Pro Glu
                435                 440                 445

Gln Tyr Ile Leu Lys Thr Gly Glu Gly Val Ala Thr Ile Cys Val Ser
                450                 455                 460

Gly Phe Ala Ala Leu Asp Val Pro Pro Arg Gly Pro Leu Trp Ile
465                 470                 475                 480

Leu Gly Asp Val Phe Met Gly Pro Tyr His Thr Val Phe Asp Tyr Gly
                485                 490                 495

Lys Ser Gln Val Gly Phe Ala Glu Ala Ala
                500                 505

<210> SEQ ID NO 95
<211> LENGTH: 505
<212> TYPE: PRT
<213> ORGANISM: Nepenthes alata

<400> SEQUENCE: 95

Met Gly His Arg Asn Leu Trp Val Ile Phe Cys Phe Cys Ala Leu Ile
1               5                   10                  15

Ser Cys Phe Phe Ser Thr Ser Ala Asp Gly Leu Val Arg Ile Gly Leu
                20                  25                  30

Lys Arg Gln Phe Ser Asp Ser Asn Ser Ile Arg Ala Val Arg Ile Ala
                35                  40                  45

Arg Lys Ala Gly Met Asn Gln Gly Leu Lys Arg Phe Gln Tyr Ser Phe
                50                  55                  60

Gly Asp Ser Asp Thr Asp Ile Val Tyr Leu Lys Asn Tyr Leu Asp Ala
65              70                  75                  80

Gln Tyr Tyr Gly Glu Ile Gly Ile Gly Ser Pro Pro Gln Lys Phe Ser
                85                  90                  95

Val Ile Phe Asp Thr Gly Ser Ser Asn Leu Trp Val Pro Ser Ser Lys
                100                 105                 110

Cys Tyr Phe Ser Val Ala Cys Tyr Phe His Ser Lys Tyr Asn Ser Ser
                115                 120                 125

Lys Ser Ser Thr Tyr Thr Lys Ile Gly Lys Ser Cys Glu Ile Asp Tyr
                130                 135                 140

Gly Ser Gly Ser Ile Ser Gly Phe Glu Ser Gln Asp Ile Val Glu Val
145             150                 155                 160

Gly Asn Leu Ala Val Lys Asn Gln Val Phe Ile Glu Ala Ser Arg Glu
                165                 170                 175

Lys Ser Leu Thr Phe Ala Leu Ala Lys Phe Asp Gly Ile Leu Gly Ile
                180                 185                 190

Gly Phe Gln Glu Ile Ser Val Gly Asp Val Pro Val Trp Tyr Asn
                195                 200                 205

Met Val Glu Gln Gly Leu Val Ser Glu Lys Val Phe Ser Phe Trp Glu
                210                 215                 220

Asn Arg Asp Phe Lys Ala Glu Ile Gly Gly Glu Ile Val Phe Gly Gly
225             230                 235                 240

Ile Asp Glu Lys His Phe Val Gly Glu His Ile Tyr Val Pro Ile Thr
```

```
                    245                 250                 255
Arg Lys Gly Tyr Trp Gln Phe Glu Met Gly Asn Phe Leu Ile Gly Asn
            260                 265                 270

Tyr Ser Thr Gly Phe Cys Arg Gly Gly Cys Asp Ala Ile Val Asp Ser
            275                 280                 285

Gly Thr Ser Leu Leu Ala Gly Pro Met His Val Val Thr Glu Val Asn
            290                 295                 300

His Ala Ile Gly Ala Glu Gly Ile Ala Ser Met Glu Cys Lys Glu Val
305                 310                 315                 320

Val Tyr Gln Tyr Gly Asp Met Ile Trp Asp Leu Leu Val Ser Gly Val
                325                 330                 335

Gln Pro Asp Lys Ile Cys Ser Gln Leu Ala Leu Cys Phe Asn Asp Ala
            340                 345                 350

Gln Phe Leu Ser Ile Gly Ile Lys Thr Val Ile Glu Arg Glu Asn Arg
            355                 360                 365

Lys Asn Ser Ser Val Ala Asp Asp Phe Leu Cys Thr Ala Cys Glu Met
370                 375                 380

Ala Val Val Trp Ile Gln Met Gln Leu Arg Arg Glu Val Thr Lys Glu
385                 390                 395                 400

Lys Val Leu Asn Tyr Ile Asn Glu Leu Cys Asp Ser Leu Pro Ser Pro
                405                 410                 415

Met Gly Glu Ser Val Ile Asp Cys Asp Ser Ile Pro Tyr Met Pro Asn
            420                 425                 430

Val Thr Phe Thr Ile Gly Glu Lys Pro Phe Lys Leu Thr Phe Glu Gln
            435                 440                 445

Tyr Val Leu Lys Ala Gly Glu Gly Asp Ala Met Val Cys Leu Ser Gly
            450                 455                 460

Phe Ile Ala Leu Asp Val Pro Pro Ser Gly Pro Leu Trp Ile Leu
465                 470                 475                 480

Gly Asp Val Phe Met Gly Val Tyr His Thr Val Phe Asp Phe Gly Asn
                485                 490                 495

Leu Lys Leu Gly Phe Ala Glu Ser Ala
            500                 505

<210> SEQ ID NO 96
<211> LENGTH: 43
<212> TYPE: DNA
<213> ORGANISM: Artificial Sequence
<220> FEATURE:
<223> OTHER INFORMATION: Synthesized: PCR amplified fragment (FRT07)

<400> SEQUENCE: 96
caaaaccatc cccacctaag gacgacctct agattgatcc tct                43

<210> SEQ ID NO 97
<211> LENGTH: 43
<212> TYPE: DNA
<213> ORGANISM: Artificial Sequence
<220> FEATURE:
<223> OTHER INFORMATION: Synthesized: PCR amplified fragment (GPFA57)

<400> SEQUENCE: 97
caaaaccatc cccacctaag gacgagctct agattgatcc tct                43

<210> SEQ ID NO 98
<211> LENGTH: 43
<212> TYPE: DNA
<213> ORGANISM: Artificial Sequence
<220> FEATURE:
```

```
<223> OTHER INFORMATION: Synthesized: PCR amplified fragment (CCCA2)

<400> SEQUENCE: 98
caaaaccatc cccacctaag gacgagctct agattgatcc tct                43

<210> SEQ ID NO 99
<211> LENGTH: 44
<212> TYPE: DNA
<213> ORGANISM: Artificial Sequence
<220> FEATURE:
<223> OTHER INFORMATION: Synthesized: PCR amplified fragment (FRT32)

<400> SEQUENCE: 99
caaaaccatc cccacctaag gacgacctct agattgatcc ttct               44

<210> SEQ ID NO 100
<211> LENGTH: 44
<212> TYPE: DNA
<213> ORGANISM: Artificial Sequence
<220> FEATURE:
<223> OTHER INFORMATION: Synthesized: PCR amplified fragment (FRT19)

<400> SEQUENCE: 100
caaaaccatc cccacctaag gacgacctct agattgatcc ttct               44
```

POLYNUCLEOTIDE ENCODING A CYSTEINE PROTEASE

CROSS REFERENCE TO RELATED APPLICATIONS

This application is a continuation of U.S. application Ser. No. 10/559,986, filed Sep. 11, 2006, now abandoned, which is a U.S. national stage filing of International Appl. No. PCT/EP2004/006805, filed Jun. 18, 2004, which claims priority to European Appl. No. 03394056.0, filed Jun. 20, 2003, the entire contents of which are expressly incorporated herein by reference thereto.

BACKGROUND

Coffee contains a highly complex mixture of flavour molecules. Extensive research on the composition of instant and fresh ground coffee beverages has, to date, identified more than 850 compounds, many of which are flavour active molecules (Flament, I (2002) Coffee Flavor Chemistry, John Wiley and Sons, UK). However, few of the final coffee flavour molecules found in the cup of coffee are present in the raw material, the green grain (green beans) of the plant species *Coffea arabica* or *Coffea canephora* (*robusta*). In fact, the majority of the coffee flavour compounds are generated during one or more of the multiple processing steps that occur from the harvest of the ripe red coffee cherries to the final roasted ground coffee product, or extracts thereof, for example soluble coffee products.

The various steps in the production of coffee are described in Smith, A. W., in Coffee; Volume 1: Chemistry pp 1-41, Clark, R. J. and Macrea, R. eds, Elsevier Applied Science London and New York, 1985; Clarke, R. J., in Coffee: Botany, Biochemistry, and Production of Beans and Beverage, pp 230-250 and pp 375-393; and Clifford, M. N. and Willson, K. C. eds, Croom Helm Ltd, London. Briefly, the process starts with the collection of mature, ripe red cherries. The outer layer, or pericarp, can then be removed using either the dry or wet process. The dry process is the simplest and involves 1) classification and washing of the cherries, 2) drying the cherries after grading (either air drying or mechanical drying), and 3) dehusking the dried cherries to remove the dried pericarp. The wet process is slightly more complicated, and generally leads to the production of higher quality green beans. The wet process is more often associated with *C. arabica* cherries. The wet process consists of 1) classification of the cherries, 2) pulping of the cherries, this step is done soon after harvest and generally involves mechanical removal of the "pulp", or pericarp, of the mature cherries, 3) "fermentation", the mucilage that remains attached to the grain of the cherries after pulping is removed by allowing the grain plus attached mucilage to be incubated with water in tanks using a batch process. The "fermentation" process is allowed to continue up to 80 hours, although often 24 hours is generally enough to allow an acceptable fermentation and to cause the pH to drop from around 6.8-6.9 to 4.2-4.6, due to various enzymatic activities and the metabolic action of microorganisms which grow during the fermentation, 4) drying, this step involves either air or mechanical hot air drying of the fermented coffee grain and 5) "hulling", this step involves the mechanical removal of the "parch" of the dried coffee grain (dried parchment coffee) and often the silverskin is also removed at this stage. After wet or dry processing, the resulting green coffee grain are often sorted, with most sorting procedures being based on grain size and/or shape.

The next step in coffee processing is the roasting of the green grain after dehusking or dehulling of dry or wet processed coffee, respectively. This is a time-dependent process which induces significant chemical changes in the bean. The first phase of roasting occurs when the supplied heat drives out the remaining water in the grain. When the bulk of the water is gone, roasting proper starts as the temperature rises towards 190-200° C. The degree of roasting, which is usually monitored by the colour development of the beans, plays a major role in determining the flavour characteristics of the final beverage product. Thus, the time and temperature of the roasting are tightly controlled in order to achieve the desired coffee flavour profile. After roasting, the coffee is ground to facilitate extraction during the production of the coffee beverage or coffee extracts (the latter to be used to produce instant coffee products). Again, the type of grinding can influence the final flavour of the beverage.

While a considerable amount of research has been carried out on the identification of the flavour molecules in coffee, much less work has been done regarding the physical and chemical reactions which occur within the coffee grains during each of the processing steps. This latter point is particularly evident for the roasting reaction, where the large number of grain constituents undergo an extremely complex series of heat induced reactions (Homma, S. 2001, In "Coffee: Recent Developments". R. J. Clarke and O. G. Vitzthum eds, Blackwell Science, London; Yeretzian, C., et al ((2002) Eur. Food Res. Technol. 214, 92-104; Flament, I (2002) Coffee Flavor Chemistry, John Wiley and Sons, UK; Reineccius, G. A., "The Maillard Reaction and Coffee Flavor" Conference Proceedings of ASIC, 16$^{th}$ Colloque, Kyoto, Japan 1995).

While the details of most of the reactions that occur during the different steps of coffee processing remain relatively unclear, it is thought that an important flavour generating reaction responsible for many of the flavours associated with coffee aroma is the "Maillard" reaction during coffee roasting. A vigorous Maillard reaction occurs between the grain reducing sugars/polysaccharide degradation products and the amino group containing molecules (particularly the proteins, peptides, and amino acids) during the roasting step.

Because the Maillard reaction apparently makes an important contribution to the generation of coffee flavour and aroma molecules during coffee roasting, there might be an association between the levels of primary Maillard reactants in the green beans and the quality of the flavour/aroma developed after roasting.

As noted above, an important group of substrates in the Maillard reaction are amino acids, peptides and proteins. Using 2-D electrophoresis, it has been shown that differences exist in the levels and amounts of the major storage proteins in arabica and robusta green coffee beans—however, no association between these storage protein differences and flavour quality was noted (Rogers et al, 1999, Plant Physiol. Biochem. Vol 37, 261-272). It has also recently been found that small differences exist between the storage proteins of immature and mature coffee beans, which have different flavour qualities (Montavon, P. et al, 2003, J. Agric and Food Chemistry Vol 51, 2328-2334). Because there are many changes occurring during seed maturation, this latter work suggests a link may exist between the quality improvement caused by maturation and the differences seen in the 2-D gel patterns of the main coffee storage proteins.

It has recently been shown that there are differences in the profiles of peptides isolated from *arabica* and *robusta* green beans (Ludwig et al 2000, Eur. Food Res Technol., Vol 211, 111-116.). Although their results showed that the *arabica* and *robusta* peptide extracts differ in their aroma precursor profile, the data presented in this report do not identify which component(s) in the extracts is/are responsible for these aroma profile differences. These workers also detected at least two different proteinase activities in crude extracts of the green coffee, but they did not correlate any specific activities with aroma/flavour quality (Ludwig et al 2000, Eur. Food Res Technol., Vol 211, 111-116). Finally, it is also thought that the very high temperatures used during the later stages of green coffee grain roasting cause substantial cleavage of the proteins present in the coffee grain (Homma, S. 2001, In "Coffee: Recent Developments". R. J. Clarke and O. G. Vitzthum eds, Blackwell Science, London; Montavon, P., et al 2003, "Changes in green coffee protein profiles during roasting", J. Agric. Food Chem. 51, 2335-2343). However, the overall scheme for this protein degradation is very poorly understood, but presumably depends on, among other things, the precise state of the main coffee proteins in the raw material before the start of roasting. To our knowledge, there are no other significant reports addressing the possibility that peptide profiles in coffee could be involved in the production of coffee aroma/flavour.

In the roasting of the fermented seeds of *Theobroma cacao* (cocoa beans), there would appear to be an involvement of seed amino acids and peptides in the development of Maillard reaction aromas/flavours. Relative to other seeds, *T. cacao* seeds have been shown to have an unusually high level of aspartic proteinase activity (Biehl, B., Voigt, J., Voigt, G., Heinrichs, H., Senyuk, V. and Bytof, G. (1994) "pH dependent enzymatic formation of oligopeptides and amino acids, the aroma precursors in raw cocoa beans". In *The Proceedings of the 11th International Cocoa Research Conference*, 18-24 Jul. 1993, Yamoussoukro, Ivory Coast). In order to produce cocoa beans with a high level of cocoa flavour precursors, it is necessary to carry out a natural fermentation step (unfermented beans develop little flavour when roasted). During this fermentation step, the sugars in the pulp are fermented, generating high levels of acids, particularly acetic acid (Carr, J. G. (1982) Cocoa. In *Fermented Foods*. Economic Microbiology. Vol 7. pages 275-292. (A. H. Rose ed). Academic Press). As the fermentation continues, the pH in the seed decreases and the cell structure becomes disrupted. The low pH triggers the abundant cacao seed aspartic proteinase to become mobilized and/or activated, resulting in a massive degradation of cellular protein (Biehl, B., Passern, D., and Sagemann, W. (1982) "Effect of Acetic Acid on Subcellular Structures of Cocoa Bean Cotylydons". J. Sci. Food Agric. 33, 1101-1109; Biehl, B., Brunner, E., Passern, D., Quesnel, V. C., and Adomako, D. (1985) "Acidification, proteolysis and flavour potential in fermenting cocoa beans". J. Sci. Food Agric. 36, 583-598). Peptides and amino acids have been shown to be cocoa flavour precursors (Rohan, T. (1964) "The precursors of chocolate aroma: a comparative study of fermented and unfermented cocoa beans". J. Food Sci., 29, 456-459; Voigt, J. and Biehl, B. (1995) "Precursors of the cocoa specific aroma components are derived from the vicilin-class (7S) globulin of the cocoa seeds by proteolytic processing". Bot. Acta 108, 283-289). Thus, the *T. cacao* seed asp artic proteinase, together with a seed serine carboxypeptidase, have been proposed to be critical for the generation of cocoa flavour precursors during fermentation (Voigt, J. and Biehl, B. (1995) "Precursors of the cocoa specific aroma components are derived from the vicilin-class (7S) globulin of the cocoa seeds by proteolytic processing". Bot. Acta 108, 283-289; Voigt, J., Heinrichs, H., Voigt, G. and Biehl, B. (1994) "Cocoa-specific aroma precursors are generated by proteolytic digestion of the vicilin-like globulin of cocoa seeds". Food Chemistry, 50, 177-184.) The gene encoding the abundant cacao seed aspartic proteinase has been identified and a method to over-express this protein in cacao seeds which can generate increased levels of cacao flavour precursor amino acids and peptides in fermented cocoa beans has recently been described in International Patent Publication No. 02/04617, the whole contents of which are incorporated herein by reference. However, the teaching of International Patent Publication No. 02/04617 is directed towards cacao seeds, which undergo a specific long acid fermentation step, unlike coffee grains which do not.

An important vacuolar cysteine proteinase (CP) is the KDEL (SEQ ID NO: 17) containing cysteine proteinase. This type of proteinase has been characterized in several plants. To date, three genes encoding cysteine proteinases with C-terminal KDEL (SEQ ID NO: 17) sequences have been found in *arabidopsis* (Gietl, C., and Schmid, M. 2001, Naturwissenschaften 88, 49-58). One is expressed in senescing ovules, one in vascular vessels, and the third in maturing siliques. However, more detailed studies on this protein have been done in other plants. For example, a CP called the sulfhydryl-endoproteinase (SH-EP) has been characterized in the cotyledons of *Vigna mungo* seeds (Toyooka, K., Okamoto, T., and Minamikawa, T. (200) J. Cell Biol. 148, 453-463.). SH-EP is expressed de-novo in germinating cotyledons of V. mungo, and is proposed to be involved in the degradation of storage proteins accumulated in the protein storage vacuoles (Okamato, T. and Minamikawa, T. J. Plant Physiol. 152, 675-682). A key feature of the SH-EP polypeptide is that it possesses a specific COOH terminal sequence KDEL (SEQ ID NO: 17) which directs the transport of this protein from the endoplasmic reticulum (ER) to the protein storage vacuoles (Toyooka et al., 2000). It has also been recently proposed that the SH-EP protein is actually involved, via the presence of its KDEL (SEQ ID NO: 17) sequence, in the formation of specific vesicles called KV (KDEL Vesicles) in a previously undescribed vesicle transport system (Okamato, T., Shimada, T., Hara-Nishimura, I., Nishimura, M., and Minamikawa, T. (2003) Plant Physiology, 132, 1892-1900).

A related proposal has been made for a KDEL (SEQ ID NO: 17) containing CP protein found in germinating castor bean cotyledons (*Ricinus communis*). In this plant, the authors implicate this KDEL (SEQ ID NO: 17) proteinase in the programmed cell death of the endosperm to continue suppling nutrients for the germinating castor bean embryo (Gietl, C., and Schmid, M. 2001, Naturwissenschaften 88, 49-58). These authors propose that, in the castor bean, the KDEL (SEQ ID NO: 17) proteinase is made in the ER of germinating seeds before day 3. When the seed coat is cast off, around day 3, the KDEL (SEQ ID NO: 17) containing CP then gets packaged into a specific vesicle called a ricinosome. Later, as the endosperm becomes soft between day 4-5, the KDEL (SEQ ID NO: 17)—CP has its anchor sequence (KDEL) (SEQ ID NO: 17) cleaved off and this proteinase migrates to the cytoplasm where it assists in the general degradation of the cellular protein.

SUMMARY

It is an object of the present invention to modify protein/peptide/amino acid flavour precursor pools in coffee.

More specifically, it is an object of the present invention to modify the levels of the flavour precursors in the raw material (the green grain) so that, following post harvest treatment and roast-processing, an altered flavour may be achieved. Without being bound by theory, it is believed that, if there are variations in the levels of peptides and protein degradation between coffees with significantly different flavours, then these variations could be due to differences in the endogenous proteinase activities in these different grains This difference might be detectable at the level of mRNA expression by variations in the levels of expression for particular seed proteinase genes.

The present invention involves, therefore, identifying gene sequences encoding for coffee grain (seed) specific proteinases and showing that there are indeed variations in the expression of these genes in *arabica* and *robusta*.

More specifically, the present invention discloses two major coffee cysteine proteinases (CcCP-1 and CcCP-4), four major coffee cysteine proteinase inhibitors (CcCPI-1, CcCPI-2, CcCPI-3 and CcCPI-4) and two coffee aspartic proteinases (CcAP-1 and CcAP-2), all of which are expressed in coffee seeds. We further show how either over-expression of these proteins specifically late in seed development, or the reduced expression of these proteins during late seed development, can alter the amino acid/peptide/protein profile of the mature beans. By using one or more of the disclosed gene sequences and gene constructs to alter the amino acid/peptide/protein profile of the mature beans, we disclose a new method to alter the flavour precursor profile of mature coffee beans.

In a first aspect, the present invention provides an isolated polynucleotide comprising a nucleotide sequence encoding a polypeptide having cysteine proteinase activity, wherein the amino acid sequence of the polypeptide and the amino acid sequence selected from SEQ ID Nos. 2 or 16 have at least 70%, preferably at least 80%, sequence identity based on the ClustalW alignment method; or the complement of the nucleotide sequence, wherein the complement contains the same number of nucleotides as the nucleotide sequence, and the complement and the nucleotide sequence are 100% complementary. Preferably, the amino acid sequence of the polypeptide and the amino acid sequence of SEQ ID Nos. 2 or 16 have at least 85%, preferably at least 90%, optionally at least 95%, sequence identity based on the ClustalW alignment method. Preferably, the nucleotide sequence comprises the nucleotide sequence of SEQ ID Nos. 1 or 15. Preferably, the polypeptide comprises the amino acid sequence of SEQ ID Nos. 2 or 16.

In a second aspect, there is provided an isolated polynucleotide comprising a nucleotide sequence encoding a polypeptide having cysteine proteinase inhibitor activity, wherein the amino acid sequence of the polypeptide and the amino acid sequence selected from SEQ ID Nos. 4, 10, 12 and 14 have at least 70%, preferably at least 80%, sequence identity based on the ClustalW alignment method; or the complement of the nucleotide sequence, wherein the complement contains the same number of nucleotides as the nucleotide sequence, and the complement and the nucleotide sequence are 100% complementary. Preferably, the amino acid sequence of the polypeptide and the amino acid sequence selected from SEQ ID Nos. 4, 10, 12 and 14 have at least 85%, preferably at least 90%, optionally at least 95%, sequence identity based on the ClustalW alignment method. Preferably, the nucleotide sequence comprises the nucleotide sequence selected from SEQ ID Nos. 3, 9, 11 or 13, optionally from SEQ ID Nos. 9, 11 or 13, further optionally from SEQ ID Nos. 9 or 13; still further optionally being SEQ ID No. 9. Preferably, the polypeptide comprises the amino acid sequence selected from SEQ ID Nos. 4, 10, 12 and 14, optionally from SEQ ID Nos. 10, 12 and 14, further optionally from SEQ ID Nos. 10 or 14; still further optionally being SEQ ID No. 10.

In a third aspect, there is provided an isolated polynucleotide comprising a nucleotide sequence encoding a polypeptide having aspartic endoproteinase activity, wherein the amino acid sequence of the polypeptide and the amino acid sequence selected from SEQ ID No. 6 or 8, preferably SEQ ID No. 8, have at least 75%, preferably at least 80%, sequence identity based on the ClustalW alignment method, or the complement of the nucleotide sequence, wherein the complement contains the same number of nucleotides as the nucleotide sequence, and the complement and the nucleotide sequence are 100% complementary. Preferably, the amino acid sequence of the polypeptide and the amino acid sequence selected from SEQ ID No. 6 or 8, preferably SEQ ID No. 8, have at least 85%, preferably at least 90%, optionally at least 95%, sequence identity based on the ClustalW alignment method. Preferably, the nucleotide sequence comprises the nucleotide sequence of SEQ ID No. 5 or 7, preferably SEQ ID No. 7. Preferably, the polypeptide comprises the amino acid sequence of SEQ ID No. 6 or 8, preferably SEQ ID No. 8.

In a further aspect, there is provided a vector comprising the polynucleotide of any one of first to third aspects of the invention.

In a further aspect, there is provided a non-native recombinant DNA construct comprising the polynucleotide of any one of first to third aspects of the invention, operably linked to a regulatory sequence. It will be appreciated that, in the non-native construct, either the polynucleotide is non-native or the regulatory sequence is non-native or both are non-native.

In a further aspect, there is provided a method for transforming a cell comprising transforming the cell with the polynucleotide of any one of first to third aspects of the present invention.

In a further aspect, there is provided a cell comprising the aforementioned non-native recombinant DNA construct, which cell is preferably a prokaryotic cell, an eukaryotic cell or a plant cell, preferably a coffee cell.

In a further aspect, there is provided a transgenic plant comprising such a transformed cell.

In the present application, coffee cherry terms are defined as follows: coffee cherry; entire fruit; exocarp, skin; pericarp, fleshy major outer layer of cherry; and grain, coffee seed. For a fuller explanation of these terms, reference is made to Clarke, R. J., in Coffee: Botany, Biochemistry, and Production of Beans and Beverage, pp 230, Clifford, M. N. and Willson, K. C. eds, Croom Helm Ltd, London, the contents of which are incorporated in their entirety.

The invention can be understood from the following detailed description and the accompanying Sequence Listing which forms part of the present application.

Table 1 hereunder lists the polypeptides that are described herein, along with the corresponding sequence identifier (SEQ ID No) as used in the attached listing.

Table 1:
SEQ ID No 1 (CcCP1: Cysteine proteinase, nucleic acid and its corresponding amino acid)
SEQ ID No 2 (CcCP1: Cysteine proteinase, amino acid)
SEQ ID No 3 (CcCPI-1: Cysteine proteinase Inhibitor, nucleic acid and its corresponding amino acid)
SEQ ID No 4 (CcCPI-1: Cysteine proteinase Inhibitor, amino acid)
SEQ ID No 5 (CcAP1 Aspartic endoproteinase 1, nucleic acid and its corresponding amino acid)
SEQ ID No 6 (CcAP1: Aspartic endoproteinase 1, amino acid)
SEQ ID No 7 (CcAP2: Aspartic proteinase 2, nucleic acid and its corresponding amino acid)
SEQ ID No 8 (CcAP2: Aspartic proteinase 2, amino acid)
SEQ ID No 9 (CcCPI-2: Cysteine proteinase Inhibitor, nucleic acid and its corresponding amino acid)
SEQ ID No 10 (CcCPI-2: Cysteine proteinase Inhibitor, amino acid)

SEQ ID No 11 (CcCPI-3: Cysteine proteinase Inhibitor, nucleic acid and its corresponding amino acid)
SEQ ID No 12 (CcCPI-3: Cysteine proteinase Inhibitor, amino acid)
SEQ ID No 13 (CcCPI-4: Cysteine proteinase Inhibitor, nucleic acid and its corresponding amino acid)
SEQ ID No 14 (CcCPI-4: Cysteine proteinase Inhibitor, amino acid)
SEQ ID No 15 (CcCP-4: Cysteine proteinase, nucleic acid and its corresponding amino acid)
SEQ ID No 16 (CcCP-4: Cysteine proteinase, amino acid)

The sequence listing employs the one letter codes for nucleotide sequence characters and the three letter codes for amino acids as defined for IUPAC-IUBMB Standards and as described in Nucleic Acids Research 13:3021-3030 (1985), which is incorporated herein by reference.

Additional features and advantages are described herein, and will be apparent from, the following Detailed Description and the figures.

BRIEF DESCRIPTION OF THE FIGURES

FIG. 1 shows a Northern blot analysis of cysteine proteinase gene in different tissues of *Coffea arabica*, in which the lanes are labeled R: root, S: stem, L: young leaves; and SG, LG, Y and Red are grain from small green fruit, large green fruit, yellow fruit and red fruit, respectively. Five micrograms of total RNA was loaded in each lane. Panel B illustrates an autoradiogram after 24 hours exposure showing the appearance of CcCP-1 mRNA in the tissues tested and Panel A demonstrates the ethidium bromide staining of the gels prior to blotting.

FIG. 2A shows a Northern blot analysis of the expression of the Cysteine proteinase CcCP-1 gene in different tissues of *Coffea arabica*, in which lanes are labelled R, root; S, stem; L, young leaves; F, flowers. SG (G), LG (G), Y (G) and Red (G) correspond to RNA isolated from the grain of small green, large green, yellow and red cherries, respectively, and lanes which are labelled SG (P), LG (P), Y (P) and Red (P) correspond to RNA isolated from the pericarp tissue of small green, large green, yellow and red cherries, respectively. Five micrograms of total RNA was loaded in each lane. Panel A demonstrates the ethidium bromide staining of the large ribosomal RNA prior to blotting as a loading control, Panel B is an autoradiogram showing the appearance of the CcCP-1 mRNA in the specific tissues tested.

FIG. 2B: Alignment of the full sequence of the protein encoded by CcCP-1 cDNA with other full-length cysteine proteinases available in the NCBI database. This was done in Megalign by the CLUSTAL method in the MegAlign (DNASTAR). Shaded blocks indicate identical amino acids. Accession numbers of the EMBL database are given in parentheses. *Arabidopsis thaliana* (AY070063); *Vicia sativa* (Z99172); *Glycine max* GMCP3 (Z32795); *Glycine max* GmPM33 (AF167986); *Phaseolus vulgaris* Moldavain (Z99955); *Solanum melongena* (AF082181); *Nicotiana tabacum* (AJ242994); *Lycopersicon esculentum* (Z14028); *Vicia faba* (AY 161277).

FIG. 3 shows a Northern blot analysis of Cysteine proteinase inhibitor (CcCPI-1) gene in different tissues of *Coffea arabica*, in which the lanes are labeled R: root, S: stem, L: young leaves and SG, LG, Y and Red for grain from small green fruit, large green fruit, yellow fruit and red fruit, respectively. Five micrograms of total RNA was loaded in each lane. Panel B illustrates an autoradiogram after 24 hours exposure and panel A demonstrates the ethidium bromide staining of the gels prior to blotting.

FIG. 4 shows a Northern blot analysis of Cysteine proteinase inhibitor (CcCPI-1) gene in different stages of development of *Coffea arabica* (ARA) and *Coffea robusta* (ROB) fruit. The lanes are labeled small green fruit (SG), large green fruit (LG), yellow fruit (Y) and red fruit (Red), respectively. Five micrograms of total RNA was loaded in each lane. Panel B illustrates an autoradiogram after 24 hours exposure showing the appearance of CcCPI-1 mRNA in the specific tissues tested. Panel A demonstrates the ethidium bromide staining of the gels prior to blotting.

FIG. 5 shows RT-PCR analysis of the expression of CcCP-1 during *Coffea arabica* grain germination. PCR reaction was carried out using 10 µl of each cDNA diluted 1/100. The cycling conditions were 2 min at 94° C., 35 cycles of 94° C., 61° C. for 1.5 min, and 72° C. for 2.5 min. The final extension step was for 7 min at 72° C. The PCR primers were:

Figure 18:
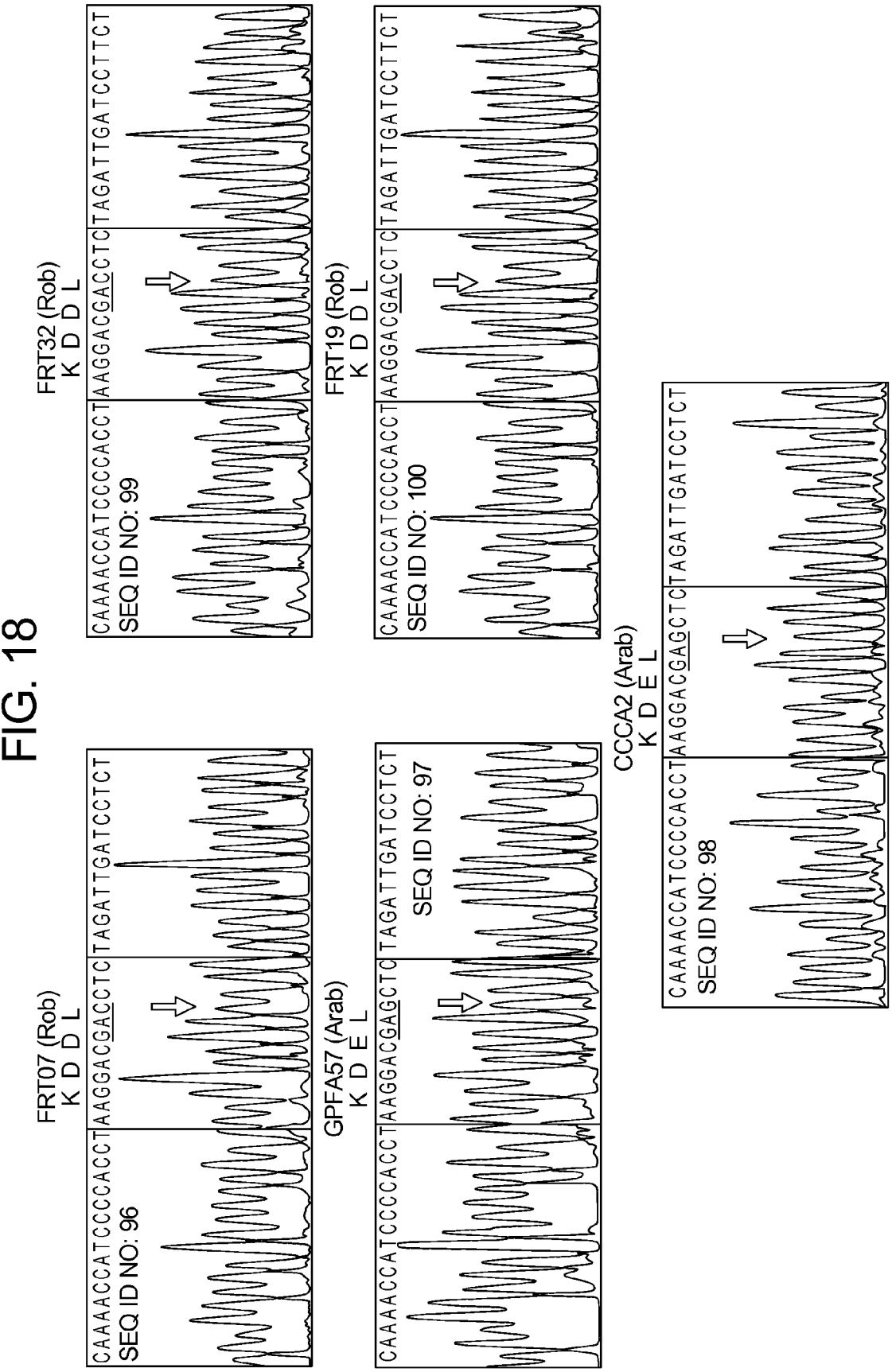

```
                                           (SEQ ID NO: 18)
A4-43-upper:  5'-ACCGAGGAGGAGTTTGAGGCTACG-3'

(SEQ ID NO: 19)
A4-43-lower:  5'-ACGCTTCCCCCATGAGTTCTTGA-3'
``` mRNAs were amplified by RT-PCR using specific primers (CcCP-1 up/CcCP-1 low) on different templates: cDNAs from sterilized seed (TO) and seeds taken after 2 days (2 d), 3 days (3 d), 5 days (5 d), 1 month (1 m) and 2 months (2 m) of germination, respectively. The PCR products were resolved in a 1% (w/v) agarose gel and stained with ethidium bromide. RPL39; amplified fragment of cDNA encoding the L39 protein of the 60S ribosomal large subunit.

FIG. 6A shows Western-blot analysis of the expression of CcCP1 protein (A). Total proteins were extracted from grains (g) and pericarp (p) collected from developing coffee cherries at stages Small Green (SG), Large Green (LG), Yellow (Y) and Red. Panel B—Separation of 50 µg of total protein on a 12% SDS-PAGE gel and stained with Comassie blue. Panel A—Protein detection was performed using a anti-CRP4 polyclonal antibody (rabbit) as described in the methods. Approximate size of bands in panel B are indicated with arrows at left. The large arrow inside each panel indicates the presence of a major storage protein that cross reacts with one of the antibodies.

FIG. 6B shows the optimal alignment of the complete protein encoded by CcCPI-1 cDNA with other homologous full-length cysteine proteinases available in the NCBI. Shaded blocks indicate identical amino acids. Accession numbers of the EMBL database and percentage identities are given in parentheses. *Malus×domestica* (AA018638; 42.3% identity), Common sunflower (JE0308; 41.5% identity), *Arabidopsis thaliana* (AAM64985; 30% identity) and *Rumex obtusifolius* (CAD21441; 29.3% identity).

FIG. 7 shows RT-PCR analysis of the expression of CcCPI-1 gene in different tissues of *Coffea arabica* CCCA2 (A) and *Coffea robusta* FRT-32 (B). PCR reaction was carried out using 10 µl of each cDNA diluted 1/1000. The cycling conditions were 2 min at 94° C., 40 cycles of 94° C. for 1 min, 60° C. for 1.5 min, and 72° C. for 1 min. The final extension step was for 7 min at 72° C. The PCR primers were:

```
                                          (SEQ ID NO: 20)
CcCPI-1 (up)  5' AGGAAAGTGGGAGCAAGGGAGAAGA 3'

(SEQ ID NO: 21)
CcCPI-1 (low) 5' TAGTATGAACCCAAGGCCGAACCAC 3'.
```

The lanes are labeled as follows: −M, Markers; +P, diluted plasmid containing the CcCPI-1 gene; R, root; S, stem; L, young leaves; F, flowers.—SG (G), LG (G), Y (G) and Red (G) are grain isolated from small green, large green, yellow and red cherries, respectively. SG (P), LG (P), Y (P) and Red (P) are pericarp tissue isolated from small green, large green, yellow and red cherries, respectively.

FIG. 8 shows the optimal alignment of the complete protein encoded by CcCPI-2 cDNA with other homologous full-length cysteine proteinases available in the NCBI. Shaded blocks indicate identical amino acids. Accession numbers of the EMBL database and percentage identities are given in parentheses. *Rumex obtusifolius* (CAD21441; 66.7% identity), *Dianthus caryophyllus* (AAK30004; 71.7% identity), *Manihot esculenta* (AAF72202; 65.2% identity).

FIG. 9 shows the RT-PCR analysis of the expression of CcCPI-2 gene in different tissues of *Coffea arabica* CCCA2 (A) and *Coffea robusta* FRT-32 (B). PCR reaction was carried out using 10 µl of each cDNA diluted 1/1000. The cycling conditions were 2 min at 94° C., 40 cycles of 94° C. for 1 min, 57° C. for 1.5 min, and 72° C. for 1 min. The final extension step was for 7 min at 72° C. The PCR primers were:

```
                                         (SEQ ID NO: 22)
CcCPI-2 (up)  5' GTGAAGCCATGGTTGAACTT 3'

(SEQ ID NO: 23)
CcCPI-2 (low) 5' GTAATGATACTCAAGCCAGA 3'.
```

The lanes are labeled as follows: −M, Markers; +P, diluted plasmid containing the CcCPI-2 gene; R, root; S, stem; L, young leaves; F, flowers.—SG (G), LG (G), Y (G) and Red (G) are grain isolated from small green, large green, yellow and red cherries, respectively.—SG (P), LG (P), Y (P) and Red (P) are pericarp tissue isolated from small green, large green, yellow and red cherries, respectively.

FIG. 10 shows the optimal alignment of the complete protein encoded by CcCPI-3 cDNA with other homologous full-length cysteine proteinases available in the NCBI. Shaded blocks indicate identical amino acids. Accession numbers of the EMBL database and percentage identities are given in parentheses. *Citrus×paradisi* (AAG38521; 42.4% identity), *Actinidia deliciosa* (AAR92223; 44.4% identity), and *Arabidopsis thaliana* (AAM64661; 44% identity).

FIG. 11 shows the optimal alignment of the complete protein encoded by CcCPI-4 cDNA with other homologous full-length cysteine proteinases available in the NCBI. Shaded blocks indicate identical amino acids. Accession numbers of the EMBL database and percentage identities are given in parentheses. *Citrus×paradisi* (AAG38521; 23.6% identity), and *Arabidopsis thaliana* (AAM64661; 20% identity).

FIG. 12 shows RT-PCR analysis of the expression of CcCPI-4 gene in different tissues of *Coffea arabica* CCCA2 (A) and *Coffea robusta* FRT-32 (B). The PCR reactions were carried out using 10 µl of each cDNA diluted 1/100. The cycling conditions were 2 min at 94° C., 40 cycles of 94° C. for 1 min, 60° C. for 1.5 min, and 72° C.×1 min. The final extension step was for 7 min at 72° C.

PCR primers were:

```
                                         (SEQ ID NO: 24)
CcCPI-4 (up)  5' CTACGGTCGCAGCCAAATC 3'

(SEQ ID NO: 25)
CcCPI-4 (low) 5' ACAACTGCACCTTCAATGTAC 3'.
```

The lanes are labeled as follows: −M, Markers; +P, diluted plasmid containing the CcCPI-4 gene; R, root; S, stem; L, young leaves; F, flowers.—SG (G), LG (G), Y (G) and Red (G) are grain isolated from small green, large green, yellow and red cherries, respectively.—SG (P), LG (P), Y (P) and Red (P) are pericarp tissue isolated from small green, large green, yellow and red cherries, respectively.

FIG. 13 shows a Northern blot analysis of aspartic proteinase 2 (CcAP2) gene in different tissues of *Coffea arabica*, in which the lanes are labelled R: root, S: stem, L: young leaves, F: flowers; SG(G) and (P), LG(G) and (P), Y(G) and (P) and Red(G) and (P) are for grain and for pericarp, respectively, from small green, large green, yellow and red cherries, and SG(G), LG(G), Y(G) and R(G) for pericarp from small green, large green, yellow and red cherries respectively. Five micrograms of total RNA was loaded in each lane. Panel A demonstrates the ethidium bromide staining of large ribosomal RNA prior to blotting as a loading control and panel B is an autoradiogram showing the appearance of the CcAP2 mRNA in the specific tissues tested.

FIG. 14 shows the cDNA sequence and the deduced amino acid sequence of CcCP-4. Lowercase: 5' and 3', non-translated regions; Uppercase: Open reading frame; Bold character: amino acid sequence; *: stop codon.

Figure 15:
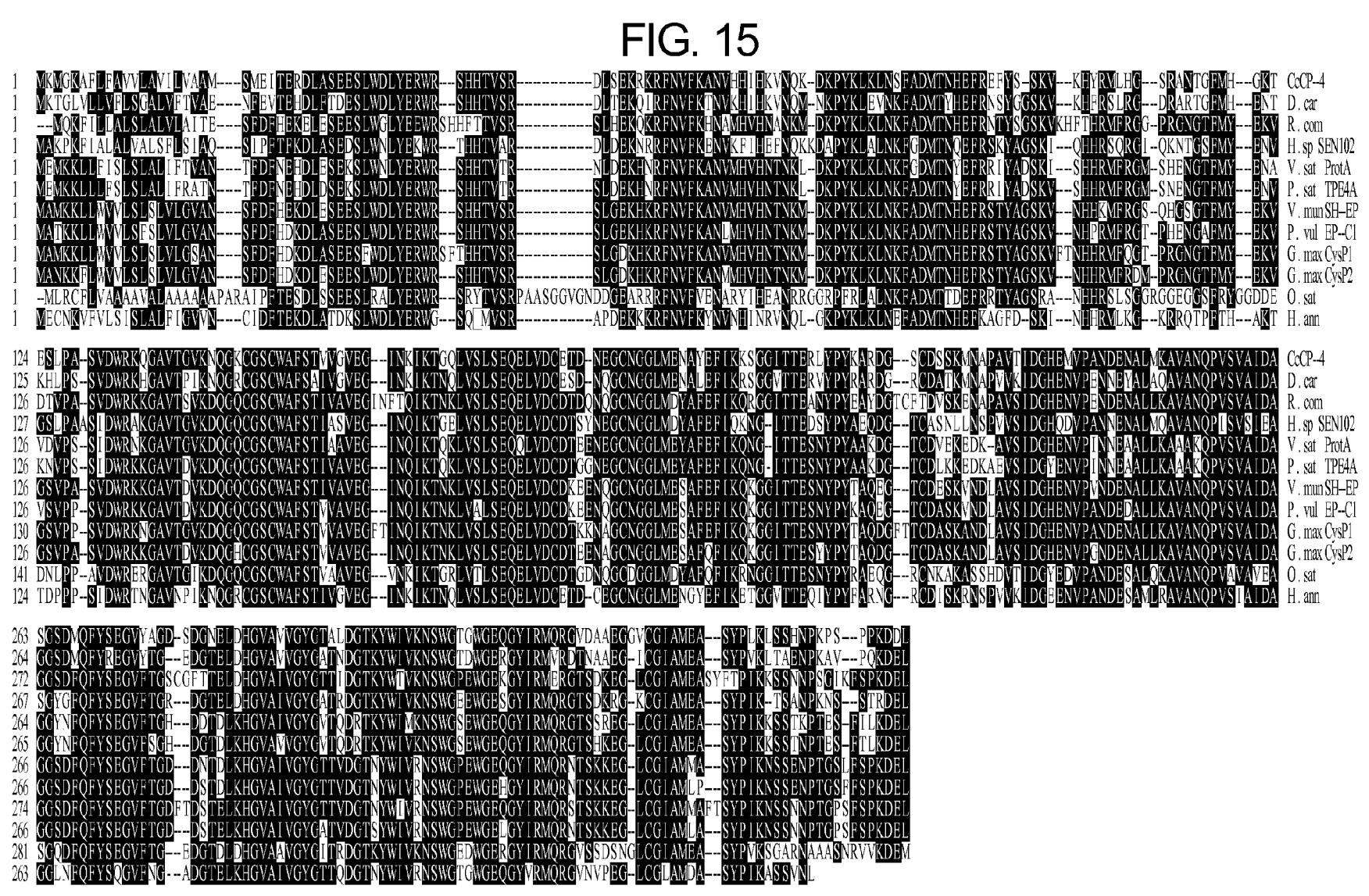

FIG. 15 shows the alignment of the full sequence of the protein encoded by CcCP-4 cDNA with other full-length cysteine proteinases available in the NCBI database. This was done using the CLUSTAL W program in the MegAlign software (Lasergene package, DNASTAR). Shaded blocks indicate identical amino acids. Accession numbers are given in parentheses. *Dacus carrota* (JC7787); *Ricinus communis* (AF050756); *Vicia sativa* (Z34895); *Phaseolus vulgaris* (X56753); *Helianthus annuus* (AB109188); *Glycine max* Cys1 (AB092555); *Glycine max* Cys2 (AB092557); *Canavalia ensiformis* (P49046); *Oryza sativa* (AB004648); *Vigna mungo* (P12412); *Pisum sativum* (AJ004985).

Figure 16:
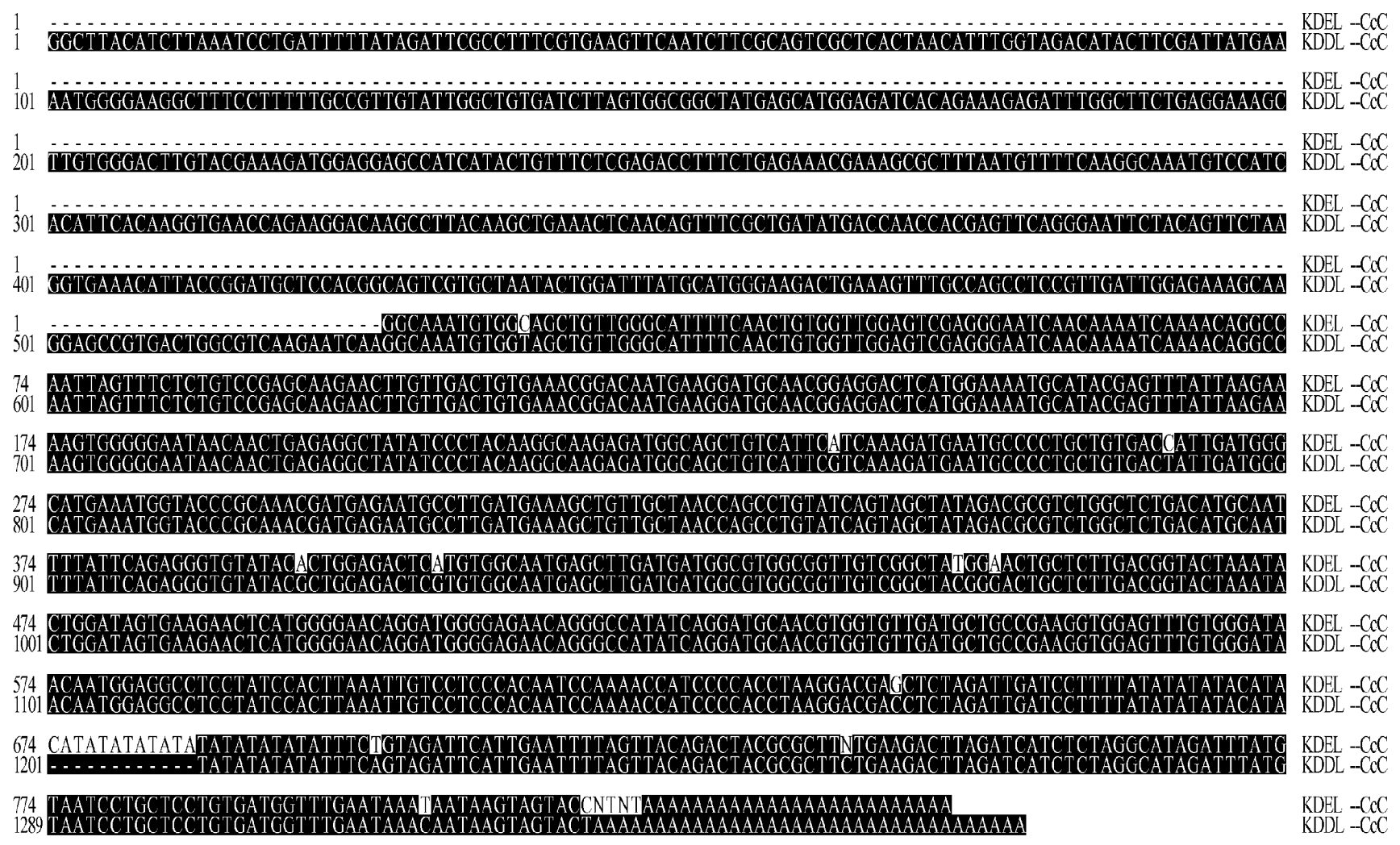

FIG. 16 shows the full length cDNA sequence CcCP-4 KDDL and the partial cDNA sequence CcCP-4 (KDEL) were aligned using the program ClustalW in Megalign.

FIG. 17 shows the complete open reading frame of CcCP-4 (KDDL) and the partial open reading frame of CcCP-4 (KDEL) were aligned using the program ClustalW in Megalign.

FIG. 18 shows the DNA sequence chromatograms for PCR amplified genomic DNA encoding the KDEL (SEQ ID NO: 17)/KDDL (SEQ ID NO: 42) region of the CcCP-4 gene. Rob, indicates a robusta variety and Arab, indicates an arabica variety.

Figure 19:
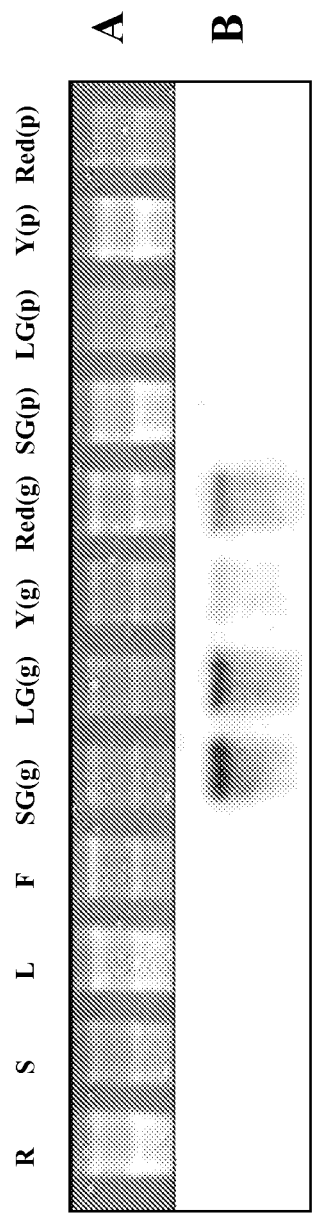

FIG. 19 shows Northern blot analysis of the expression of the Cysteine proteinase CcCP-4 gene in different tissues of *Coffea arabica*. The lanes are labeled as follows:—R, root; S, stem; L, young leaves; F, flowers.—SG (G), LG (G), Y (G) and Red (G) are grain isolated from small green, large green, yellow and red cherries, respectively.—SG (P), LG (P), Y (P) and Red (P) are pericarp tissue isolated from small green, large green, yellow and red cherries, respectively. Five micrograms of total RNA was loaded in each lane. Panel A demonstrates the ethidium bromide staining of the large ribosomal RNA prior to blotting as a loading control, Panel B is an autoradiogram showing the appearance of the CcCP-3 mRNA in the specific tissues tested.

Figure 20:
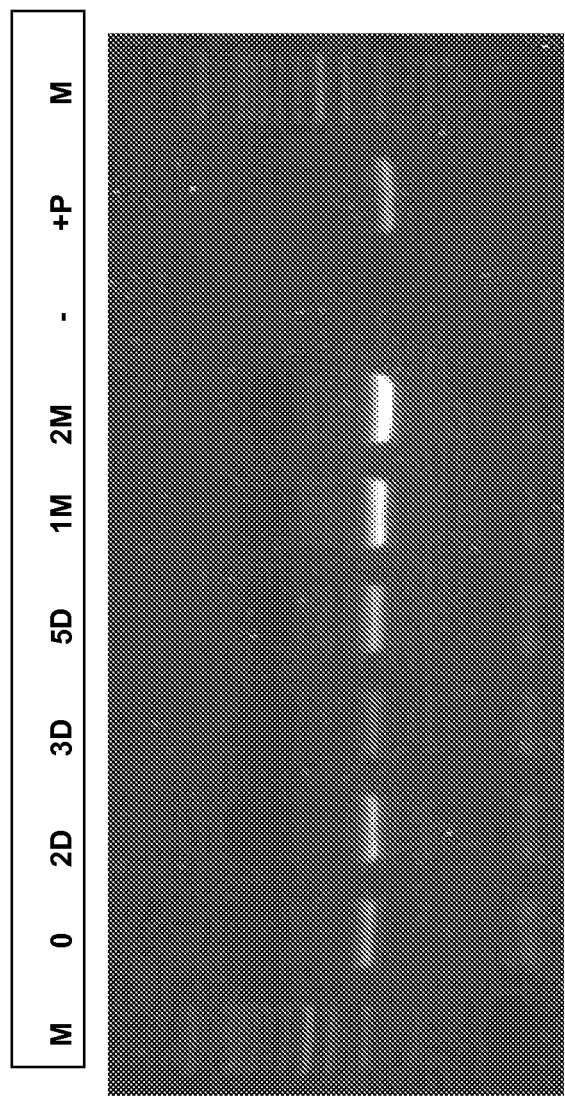

FIG. 20 shows RT-PCR analysis of the expression of CcCP-4 in the whole grain during germination. Sampling times were 0, immediately after sterilization treatment; 2D, 2 days after treatment; 3D, 3 days after treatment; 5D, 5 days after treatment; 1M, one month after treatment, 2M, two months after treatment;—, no DNA control; +P, diluted CcCP-4 plasmid DNA; M, molecular weight markers.

Figure 21:
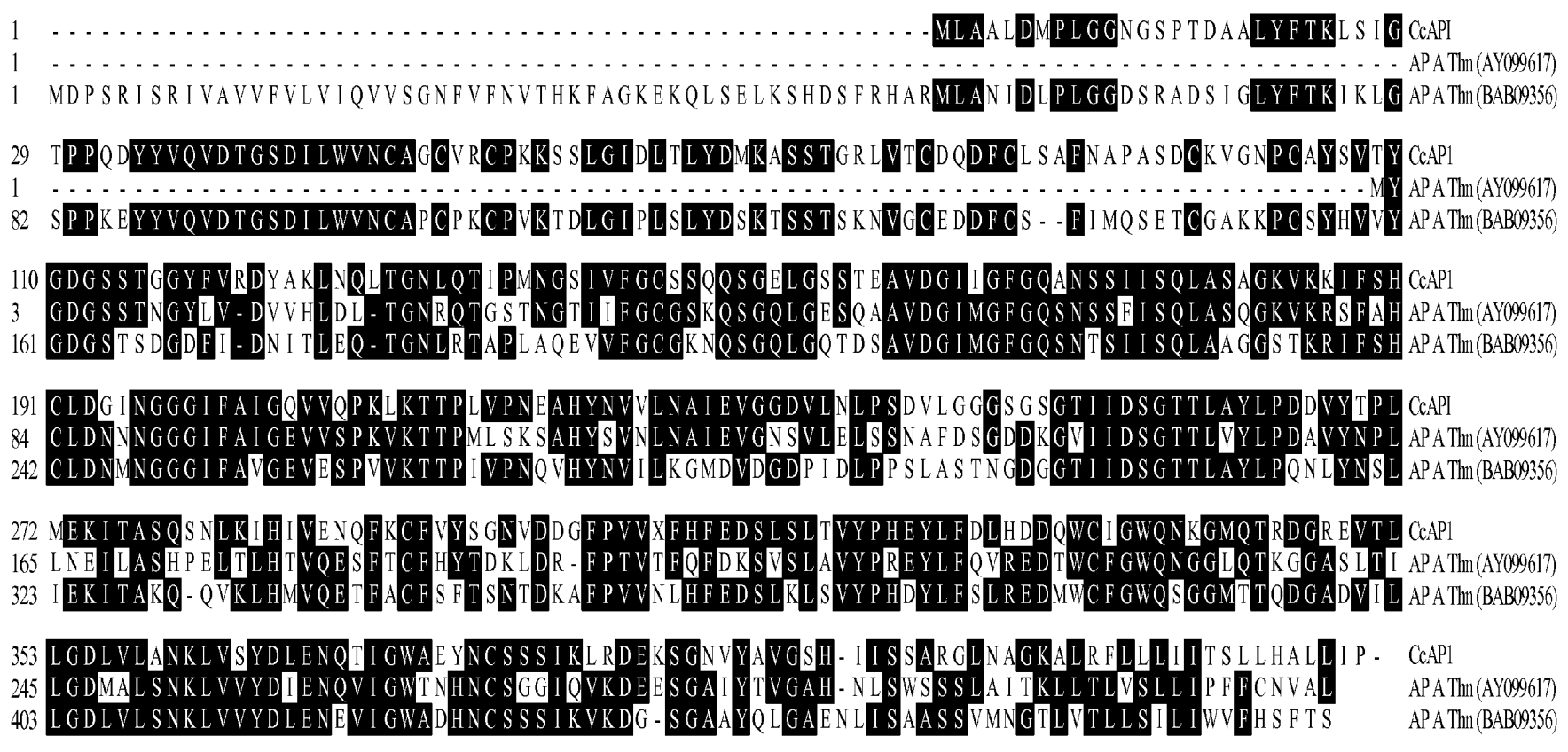

FIG. 21 shows optimal alignment of the complete protein encoded by CcAP-1 cDNA with other homologous full-length aspartic proteinase sequences available in the NCBI. Shaded blocks indicate identical amino acids. Database accession numbers are given in parentheses. *Arabidopsis thaliana* (AY099617) and *Arabidopsis thaliana* (BAB09366).

Figure 22:
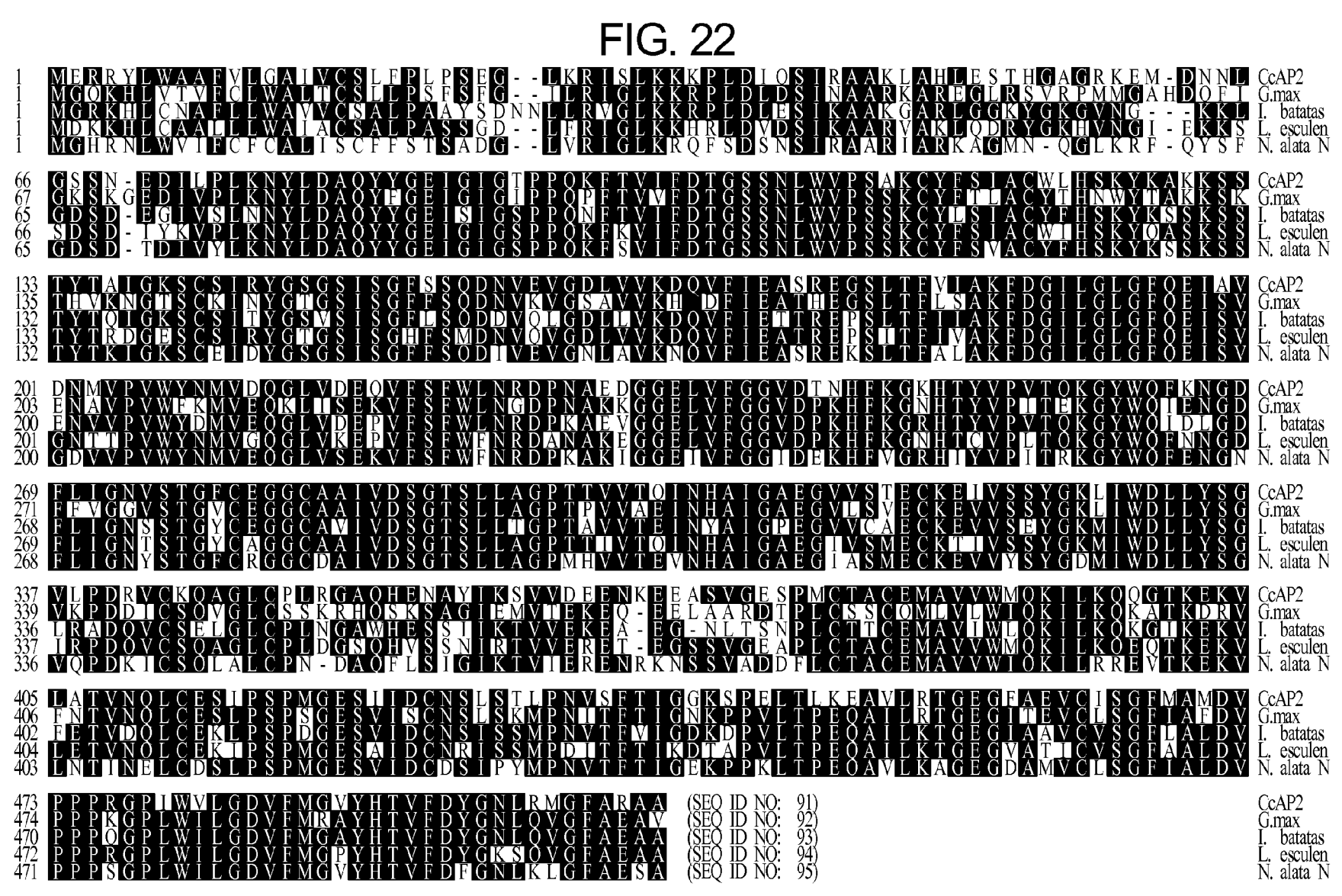

FIG. 22 shows optimal alignment of the complete protein encoded by CcAP-2 cDNA with other homologous full-length aspartic proteinase sequences available in the NCBI. Shaded blocks indicate identical amino acids. Database accession numbers are given in parentheses. *Glycine max* (BAB64296), *Ipomoea batatas* (AAK48494), *Lycopersicon esculentum* (S71591) and *Nepenthes alata* (BAB20972).

DETAILED DESCRIPTION

As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may comprise one or more segments of cDNA, genomic DNA, synthetic DNA or mixtures thereof.

Similar nucleic acid fragments are characterised, in the present invention, by the percent identity of the amino acid sequences that they encode, to the amino acid sequences disclosed herein, as determined by algorithms commonly used by those skilled in the art. Suitable nucleic acid fragments (or isolated polynucleotides of the first to third aspects of the present invention) encode polypeptides that are at least 70% identical, preferably at least 80% identical, to the amino acid sequences disclosed herein. Preferred nucleic acid fragments encode amino acid sequences that are at least 85% identical to the amino acid sequences disclosed herein. More preferred nucleic acid fragments encode amino acid sequences that are at least 90% identical to the amino acid sequences disclosed herein. Still more preferred are nucleic acid fragments that encode amino acid sequences that are at least 95% identical to the amino acid sequences disclosed herein. Multiple alignment of sequences should be performed using the ClustalW method of alignment (Thompson et al, 1994, Nucleic Acids Research, Vol 22, p 4673-4680; Higgins & Sharp 1989 Cabios. 5:151-153).

As used herein, the term "similar nucleic acid fragments" refers to polynucleotide sequences in which changes in one or more nucleotide bases result in substitution of one or more amino acids, but which changes either do not affect the function of the polypeptide encoded by the nucleotide sequence or do not affect the ability of nucleic acid fragment to mediate gene expression by gene silencing via, for example, antisense or co-expression technology. The term "similar nucleic acid fragments" also refers to modified polynucleotide sequences, in which one or more nucleotide bases is/are deleted or inserted, provided that the modifications either do not affect the function of the polypeptide encoded by the nucleotide sequence or do not affect the ability of nucleic acid fragment to mediate gene expression by gene silencing. It will, therefore, be understood that the scope of the present invention extends beyond the polynucleotide and polypeptide sequences specifically disclosed herein.

Similar nucleic acid fragments may be selected by screening nucleic acid fragments in the form of subfragments or modified nucleic acid fragments, for their ability to affect the level of the polypeptide encoded by the unmodified nucleic acid fragments in the plant or plant cell.

The term "operably linked" refers to the association of two or more nucleic acid fragments on a single nucleic acid fragment so that the function of one is affected by the other. "Regulatory sequences" refer to nucleotide sequences located upstream, within, or downstream, of a coding sequence and which influence transcription, RNA processing or stability, or translation of the coding sequence associated therewith. Regulatory sequences may include promoters, translation leader sequences, introns, transcription termination sequences and polyadenylation recognition sequences. When a regulatory sequence in the form of a promoter is operably linked to a coding sequence, the regulatory sequence is capable of affecting the expression of the coding sequence. Coding sequences can be operably linked to regulatory sequences in sense or antisense orientation.

The term "expression" refers to the transcription, and stable accumulation, of sense RNA (mRNA) or antisense RNA derived from the nucleic acid fragments of the present invention. Expression may also refer to the translation of mRNA into a polypeptide. Overexpression refers to the production of a gene product in a transgenic cell, that exceeds the level of production in normal, or non-transformed, cells. "Altered levels" refers to the production of gene product(s) in a transgenic cell in amounts or proportions that differ from that of normal, or non-transformed, cells.

"Transformation" refers to the transfer of a nucleic acid fragment into the genome of a host cell, resulting in genetically stable inheritance. Host cells containing the transformed nucleic acid fragments are referred to herein as "transgenic cells".

Standard recombinant DNA and molecular cloning techniques as used herein are well known in the art and are described more fully in Sambrook et al "Molecular Cloning: A Laboratory Manual"; Cold Spring Harbor Laboratory Press: Cold Spring Harbor, 1989, which is incorporated herein by reference.

EXAMPLES

The following Examples illustrate the invention without limiting the invention to the same. In the examples, all parts and percentages are by weight and degrees are in Celsius, unless this is otherwise specified.

In the following Examples, these abbreviations have been used:

PCR: Polymerase chain reaction
RACE: Rapid amplification cDNA ends

From the above discussion and the Examples below, those skilled in the art can ascertain the essential features of the present invention, and without departing from the scope thereof can make various changes and modifications thereto, to adapt it to various usages and conditions as desired.

Production of cDNA Libraries and Screening

Production of Seed Specific RNA Coffee cherries of the *Robusta* variety Q121 were harvested 30 WAF (weeks after flowering) at the ICCR1, Indonesia. The pericarps of these cherries were then removed and the remaining perisperm/endosperm material was frozen and ground to a powder in liquid nitrogen. The RNA was extracted from the frozen powder material using the method described previously for the RNA extraction of cacao seeds (Guilloteau, M. et al, 2003, Oil bodies in *Theobroma cacao* seeds: cloning and characterisation of cDNA encoding the 15.8 and 16.9 kDa oleosins. Plant Science Vol 164, 597-606). Poly A$^+$RNA was prepared from approximately 250 μg total RNA using the "PolyA Purist™" kit of AMBION (manufactured by Ambion, Inc.) according to their kit instructions.

Production of First Set of Seed cDNA Clones

Approximately 50-100 ng of this poly A+RNA was then employed in the synthesis of the first strand cDNA using "SuperScript™ II RNase H" reverse transcriptase (GIBCO-BRL™) and the SMART™ PCR cDNA synthesis kit (Clontech) as follows. A reaction containing 20 of 30 WAF poly A+RNA, 1 μL CDS oligo (SMART™ PCR cDNA kit, Clontech), 1 μL Smart II oligo (SMART™ PCR cDNA kit, Clontech), and 8 μL deionised H$_2$O. This mixture was heated to 72° C. for 5 minutes and then placed on ice. Then the following was added; 1 μL 10 mM dNTPs, 4 μL SuperScriptII™ 1$^{st}$ stand buffer and 2 μL DTT. This mixture was put at 42° C. for 2 minutes then 1 μL of SuperScriptII™ RNaseif reverse transcriptase (200 units/μL GIBCO BRL™) was added and the mixture was incubated in an air circulating incubator at 42° C. for a further 50 minutes.

After the reverse transcription reaction, the following PCR reaction was carried out. 98 μL of the Master Mix described in the SMART™ PCR cDNA kit (Clontech) containing Advantage™ 2 polymerase (Advantage™ 2 PCR kit, ClonTech) was set up on ice and then 3 of the 1$^{st}$ strand cDNA synthesis reaction described above was added. This 100 μL PCR reaction was then placed in a MJ Research PTC-150 HB apparatus and the following PCR conditions were run: 95° C. for 1 minute, then 16 cycles of 95° C. for 15 seconds, 65° C. for 30 seconds, 68° C. for 6 minutes. The amplified DNA was purified using the Strataprep™ PCR Purification Kit (Stratagene) according to the suppliers' instructions. The DNA, which was eluted in 50 μL deionized water, was then "polished" using the Pfu-1 polymerase reagents contained in the PCR-Script™ Amp cloning kit (Stratagene) as follows; 50 μL DNA, 5 μL 10 mM dNTPs, 6.5 μL 10×Pfu-1 polishing buffer, 5 μL cloned Pfu-1 DNA polymerase (0.5 U/0). This reaction was then incubated at 72° C. for 30 minutes in a PCR apparatus with a heated cover (Perkin Elmer). Using the protocol described in the pPCR-Script™ Amp kit (Stratagene), the polished (blunted) PCR products were ligated into the Srf-1 digested pPCR-Script™ Amp SK(+) vector in the presence of Srf-1 enzyme and the ligation reaction products were transformed into the XL-10 Gold™ Kan ultracompetent *E. coli* cells. Selection for transformation with plasmids containing inserts was done using LB-Amp plates and IPTG and Xgal spread on the surface as described in the pPCR-Script™ Amp kit. White colonies were selected and the clones were named Dayl-1 etc.

Production of Second Set of Seed cDNA Clones with Size Selected cDNA

Seeds highly express a small number of proteins, such as the seed storage proteins (White et al, 2000, Plant Physiology, Vol 124, 1582-1594). When cDNA is prepared from such tissue, the very high level of the storage proteins and other seed specific proteins leads to a high level of cDNA "redundancy", that is, the population of cDNA produced contains high proportions of the same cDNA. In order to reduce the redundancy of cDNA made from coffee seed mRNA, and to selectively characterise long and weakly expressed cDNA, a second cDNA cloning strategy was also used. Using the products of the reverse transcriptase reaction described above, the following PCR reactions was set up using the Advantage™ 2 PCR kit (ClonTech): 3 μL of the reverse transcriptase reaction, 5 μL 10× Advantage™ 2 PCR buffer, 1 μL dNTP's (10 mM each), 2 μL PCR primer (SMART™ PCR cDNA kit, Clontech), 39 μL deionised water, and 1 μL 50× Advantage 2 polymerase mix. This PCR reaction was then placed in a MJ Research PTC-150 HB apparatus and the following PCR conditions were run: 95° C. for 1 minute, then 16 cycles of 95° C. for 15 seconds, 65° C. for 30 seconds, 68° C. for 6 minutes. At the end of the PCR, 1 μL 10% SDS was added with gel loading buffer, the sample was heated to 37° C. for ten minutes. The sample was then split for loading onto a 0.7% agarose gel without ethidium bromide: 10% was loaded into a small well beside a DNA marker lane and the other 90% was loaded into a neighbouring large, preparation scale well. After the gel was run, the gel section with the size markers, plus the 10% reaction sample, were stained with ethidium bromide. This stained gel section was then used as a template to generate gel slices containing PCR amplified cDNA of different sizes from the cDNA present in the remaining unstained (preparation) part of the gel. Six gel slices were generated having the indicated size range of PCR fragments; A1A (0.8-1 kb), A1B (1-1.5 kb), A2 (1.5-2.25 kb), A3 (2.25-3.25), A4 3.25-4 kb), and A5 (4-6.5 kb).

The DNA in each gel slice was eluted from the agarose using the QIAEX II kit from Qiagen following the suppliers instructions (for samples 3A, 4A, and 5A were heated for 10 minutes at 50° C. and 1A, 1B, and 2A were heated for 10 minutes at room temperature). The purified double stranded cDNA was then re-amplified further by PCR with a TAQ enzyme mix which makes fragments having a 3' T overhang as follows: 30 μL of the gel isolated double stranded cDNA, 5 μL 10×TAQ buffer (supplied with TAQ PLUS precision polymerase mix, Stratagene), 1 μL 40 mM dNTP's (each 10 mM), 2 μL PCR primer (SMART™ PCR cDNA kit, Clontech), 0.5 μL TAQ PLUS precision polymerase mix (Stratagene) and 11.5 μL deionised water. The PCR reaction conditions were as follows: 95° C. for 1 minute then 7 cycles 95° C. for 15 seconds, 65° C. for 1 minute, 72° C. for 8 minutes, then 1 cycle at 95° C. for 15 seconds, 65° C. for 1 minute, 72° C. for 10 minutes.

The PCR amplified DNA produced was then ligated into the vector pCR™-TOPO™ and cloned into TOP10 *E. coli* cells using the TOPO™ TA kit (Invitrogen) as described by the supplier. The clones were named by their order of isolation and their position in the sizing gel (for example, A2-1, A2-2, etc.).

Seed cDNA Screening and Preliminary Identification

The first set of white colonies obtained in Day-1 library were screened by first determining the size of each insert by PCR amplifying the insert using the primers T3 and T7 which flank the cloning site used and examining the PCR amplified fragments on a gel.

Each white colony was resuspended in 200 μl sterile water and 10-30 μl of this was added to 5 μl 10×Taq polymerase buffer (Stratagene), 1 μl 10 mM dNTP mix, 2.5 μl 20 μM T3 primer, 2.5 μl 20 μM T7 primer, 1 μA DMSO, 0.5 μl Taq polymerase (Stratagene), and H$_2$O up to 50 μl final volume). The PCR reaction program used was 94° C. for 1 mM, then 30 cycles of 94° C. for 1 min, 55° C. for L5 min and 3.5 min at 72° C., and a final cycle of 7 min at 72° C. To reduce redundancy, the PCR inserts of similar size were subjected to digestion by the restriction enzyme Hae III. Those PCR fragments with the same Hae III restriction pattern were not studied further. The plasmids of clones with PCR fragments >500 bp and which had unique Hae III restriction patterns were then purified by using the Qiawall 8 ultra plasmid kit (Qiagen) for 5' end dideoxy sequencing using the appropriate T7 or T3 sequencing primers coded in the flanking vector sequences. Because the inserts were not cloned in a directed fashion, it was first necessary to determine the 5' end of each clone by a Sca1 digestion of the purified plasmid DNA (the CDS SMART primer contains a Sca 1 site allowing the orientation of the insert to be determined). The DNA sequence data obtained was subsequently blasted against the non-redundant database protein in GENEBANK to obtain a preliminary annotation of each cDNA clone using the program BLASTX™.

Seed cDNA banks have a high level of redundancy. That is, a small number of seed mRNA have an unusually high level of expression, such as those encoding the seed storage proteins, and therefore their cDNA are very abundant in seed cDNA banks (White et al, 2000, Plant Physiology, Vol 124, 1582-1594). Therefore, as soon as the main redundant cDNA's were identified in the first round of sequencing the coffee seed cDNA, a pre-screening step was added for the white insert containing colonies prior to the determination of insert size. Four sequences were very highly expressed and the following specific primers sets were made for each of these redundant sequences, 1) 2S protein, contig 8A 5' AGCAACTGCAGCAAGGTG-GAG 3' (SEQ ID NO: 26) and contig 8B 5' CGATTTG-GCACTGCTGTGGTTC 3' (SEQ ID NO: 27) (55° C. used in PCR, 114 bp fragment), 2) 2S protein contig 15A 5' GCCCGTGCTCCTGAACCA 3' (SEQ ID NO: 28) and contig 15B 5' GTATGGTTGCG-GTGGCTGAA 3' (SEQ ID NO: 29) (55° C. used in PCR, 256 bp fragment), 3) Oleosin 15.5 contig 30A 5' ACCCCGCTTTTCGTTAT 3' (SEQ ID NO: 30) and contig 30B TCTGGCTACATCT-TGAGTTCT 3' (SEQ ID NO: 31) (55° C. used in PCR, 261 bp fragment), and 4) 11S protein contig 37A 5' GTTTCCAGACCGCCAT-CAG 3' (SEQ ID NO: 32) and contig 37B 5' ATATCCATC-CTCTTCCAACACC 3' (SEQ ID NO: 33) (59° C. used in PCR, 261 bp fragment).

The PCR reactions for this prescreen step were run as follows: 10-30 µl of the white colony in sterile H$_2$O, 5 µl 10×Taq buffer (Stratagene), 1 µl 10 mM dNTP, 2.5 µl of each primer at 20 µM, 1 µl DMSO, 0.5 µl Taq polymerase (Stratagene 10U/µl) and sterile H$_2$O was added to produce a final reaction total volume of 50 µl. The PCR program was 1 min at 94° C., then 30 cycles of 1 min at 94° C., 1.5 mM at specific temperature for each primer pair, 2.5 min at 72° C., followed by 7 mM at 72° C.

Full Length cDNA Insert Sequencing and Sequence Analysis cDNA clones whose partial sequences showed initial homologies to proteinases and proteinase inhibitors were fully sequenced on both strands using the standard dideoxy primer walking strategy. The sequences are shown under SEQ ID Nos. 1, 3, 5, 7, 9, 11, 13 and 15. The full length sequences obtained were again blasted against the GenBank non redundant protein database using BLASTX to reinforce the preliminary annotation.

Sequence identities of sequence pairs were calculated using the ClustalW™ program contained in the MegAlign™ module of the Lasergene™ software package (DNASTAR Inc). The default parameters were chosen as follows: (1—MULTIPLE ALIGNMENT PARAMETERS—Gap penalty 15.00, Gap length penalty 6.66, Delay divergent Seqs (%) 30, DNA transition weight 0.5, Protein Weight Matrix-Gonnet Series, DNA Weight Matrix IUB. 2—PAIRWISE ALIGNMENT PARAMETERS-Slow/Accurate (Gap Penalty 15.00, Gap Length Penalty 6.66), Protein Weight Matrix-Gonnet 250, DNA Weight Matrix-RJB) and the sequences used were either the full length nucleotide sequence of each cDNA or the full ORF (open reading frame) of each cDNA.

TABLE 2

Identity values between the nucleic acid and amino acid sequences of CcCP-1, CcCPI-1, CcAP-1 and CcAP-2 and related genes found in the non-redundant protein database of GenBank and those of WO 02/04617.

| cDNA Sequences | nucleotide identity (%) | protein identity (%) (ORF) |
|---|---|---|
| CcAP1 vrs TcAP1 | 2.9 | 13.3 |
| CcAP1 vrs TcAP2 | 2.4 | 9.8 |
| CcAP2 vrs TcAP1 | 55.0 | 61.5 |
| CcAP2 vrs TcAP2 | 55.1 | 61.3 |
| CcCP-1 vs *Arabidopsis thaliana* putative cysteine proteinase (AY070063) | 51.8 | 64.3 |
| CcCP-1 vs *Glycine max* cysteine endopeptidase (Z32795) | 49.1 | 61.3 |
| CcCP-1 vs *Vicia sativa* cysteine proteinase precursor (Z99172) | 49.0 | 60.9 |
| CcAP2 vs *Lycopersicon esculentum* aspartic proteinase precursor (L46681) | 65.9 | 71.1 |
| CcAP2 vs *Ipomoea batatas* putative aspartic proteinase mRNA (AF259982) | 71.7 | 69.6 |
| CcAP2 vs *Nepenthes alata* NaAP4 mRNA for aspartic proteinase 4 (AB045894) | 58.4 | 66.5 |
| CcCPI-1 vs *Malus × domestica* cystatin (AY176584) | 38.8 | 45.5 |

5' RACE PCR

The cDNA insert of clone A5-812 was found to contain introns. Therefore, to confirm the coding sequence of this protein, it was necessary to isolate a new cDNA containing the complete coding sequence. This was accomplished by using the SMART™ RACE cDNA amplification Kit (Clontech). The first strand cDNA used for the 5' RACE was made as already described for the cDNA libraries above. A gene specific primer rAP2 (5' CATATAATATTAAAAGCACCAC-CCATAA 3') (SEQ ID NO: 34) was designed—this sequence is situated 92 pb from the poly (A) tail of A5-812 clone. This specific primer was then used with the Universal Primer Mix (UPM) in the CLONTECH kit in a PCR reaction under the following conditions; 2.5 µl of first strand cDNA product, 5 µl of 10× Advantage 2 PCR Buffer (CLONTECH), 1 µl of dNTP Mix (10 mM), 1 µl of 50× Advantage 2 Polymerase Mix (CLONTECH), 5 µl of "Universal Primer A Mix" (10×) (CLONTECH), 1 µl of rAP2 (10 µM) and sterile water was added to a final volume of 50 PCR cycling conditions were 20 cycles of 30 sec at 94° C., 30 sec at 68° C. and 3 min at 72° C., followed by a final extension reaction for 5 min at 72° C. A fragment of about 1700 pb was obtained, excised from the gel using "CONCERT™ Rapid Gel Extraction kit" (GibcoBRL). The isolated fragment was cloned in the pCR 4-TOPO vector and transformed into *Escherichia coli* using the Topo-TA cloning kit (Invitrogen). The plasmid obtained was then purified using a plasmid extraction kit (QIAfilter Plasmid Midi Kit, Qiagen, France) and the insert of this plasmid was double strand sequenced.

The DNA of clone A5-442 (AP1) was found to lack the 5' region of the cDNA. To isolate this region a 5' RACE was performed using the SMART™ RACE cDNA amplification Kit (Clontech). A sequence specific primer rAP1 (5'-TG-GAGTCACAAGATGTCTCGACGAACTG-3') (SEQ ID NO: 35) situated at 396 pb from the poly (A) tail was designed. This specific primer was then used with the Universal Primer Mix (UPM) in the CLONTECH kit in a PCR reaction under the following conditions; 2.5 µl of first strand cDNA, 5 µl of 10× Advantage 2 PCR Buffer (CLONTECH), 1 µl of dNTP Mix (10 mM), 1 µl of 50× Advantage 2 Polymerase Mix (CLONTECH), 5 µl of "Universal Primer A Mix" (10×) (CLONTECH), 1 µl of rAP1, and sterile water was added to a final volume of 50 PCR cycling conditions were 20 cycles of 30 sec at 94° C., 30 sec at 68° C. and 3 min at 72° C., followed by a final extension reaction for 5 min at 72° C. A fragment of about 2,000 bp was obtained, excised from the gel using "CONCERT™ Rapid Gel Extraction kit" (Gibco-BRL). The isolated fragment was cloned in the pCR 4-TOPO vector and transformed into Escherichia coli using the Topo-TA cloning kit (Invitrogen). The plasmid obtained was then purified using a plasmid extraction kit (QIAfilter Plasmid Midi Kit, Qiagen, France) and the insert of this plasmid was double strand sequenced.

RNA Preparation for Large Est Libraries:

RNA was isolated from dissected grain and pericarp tissues at various developmental stages, and from young leaves using the method described earlier. The varieties and tissues used to prepare the RNA to generate the different Est libraries were as follows: (1) young leaves, one variety (FRT-32); (2) pericarp (8 different developmental stages) from 5 varieties (FRT 32, FRT-31, FRT-400, FRT-4001, and Q121); (3) whole cherry, 22 weeks after fertilisation (WAF) from one variety (FRT-31); (4) grain, 18+22 WAF from five varieties (FRT 32, FRT-31, FRT-400, FRT-4001, and Q121); (5) grain, 30 WAF from 5 varieties (FRT 32, FRT-31, FRT-400, FRT-4001, and Q121); (6) grain, 42 WAF from five varieties (FRT 32, FRT-31, FRT-400, FRT-4001, and Q121) and (7) grain, 46 WAF from 2 varieites (FRT-32 and Q 121).

Production of cDNA Clones, and DNA Sequence Analysis.

The cDNA clones for the various Est libraries were prepared as follows: Poly A+mRNA was isolated using the PolyATrack™ mRNA Isolation System (System IV, Promega) according to the manufacturer's instructions for small scale isolation. The purified poly A+mRNA was then used to prepare cDNA for unidirectional cloning into the lambda phage as described in the ZAP-cDNA™ library construction kit (cat #200450 Stratagene). The mass excision protocol was to excise the pBlueScript phagemid from the Uni-ZAP XR vector and white colonies were obtained after plating on 150 mm LB-ampicilin agar plates with 80 ul x-gal (20 mg/ml) and 16 ul IPTG (0.5M). Single colonies were randomly chosen to produce plasmid DNA which was then used for sequencing the 5' ends of the cDNA inserts.

The DNA sequences obtained produced an EST sequence (Expressed Sequence Tag) for each clone. All the Est sequence data from the 7 libraries was then clustered "in-silico", producing a unique group of sequences called the "unigene" sequence set. Thus, each "unigene" sequence theoretically corresponds to a distinct gene product. However, it should be noted that, because many unigenes only represent partial cDNA sequences, it is likely that some genes may be represented by two or more unigenes. Then a preliminary annotation of the unigene set was carried out with an automatic BLAST search where each unigene sequence was searched against the non-redundant GenBank protein database. This BLAST search approach produced the five best BLAST "hits" ("hits" with the lowest e-values) which is referred to as the "unigene annotation".

Northern-Blot Analysis

Freshly harvested roots, young leaves, stem, flowers and fruit at different stages of development (small green fruit (SG), large green fruit (LG), Yellow fruit (Y) and red fruit (R)) were harvested from Coffea arabica CCCA2 grown under greenhouse conditions (25° C., 70 RH) in Tours, France, and from Coffea canephora FRT32 grown either in Equador or ICCR1, Indonesia. The fresh tissues were frozen immediately in liquid nitrogen and total RNA was isolated from each tissue using the extraction procedure described above. A total of 5 µg of RNA was run on a 1.2% (w/v) denaturing RNA gel containing formaldehyde. The total RNA samples from each plant tissue were heated at 65° C. for 15 min in presence of 7 µL "RNA Sample Loading Buffer" (without ethidium bromide, Sigma), and then put immediately on ice for 2 minutes before being loaded onto the 1.2% RNA gel. The gels were run at 60 Volts for 5 hours. The gel was then soaked twice in 10×SSC for 20 min. The RNA in the gel was transferred overnight by capillary transfer to a "Positive TM Membrane" (Qbiogene) in 10×SSC and the RNA was fixed by heating the blot for 30 min at 80° C. Probes were generated using "Rediprime™ II random prime labelling system" kit (Amersham) in the presence of ($P^{32}$) dCTP. Hybridisation was carried out at 65° C. for 24 h in hybridisation solution (5×SSC, 40 µg/ml Denatured Salmon Sperm DNA, 5% [w/v] SDS, and 5×Denhardt's solution). Then, the membrane was washed twice at 65° C. using 2×SSC, 0.1% SDS [w/v] and 1×SSC, 0.1% SDS [w/v] during 30 minutes each.

The Northern blot analysis shown in FIG. 1 demonstrates that the coffee cysteine proteinase gene CcCP-1 gene is expressed in the C. arabica coffee cherry at all the stages tested, with yellow cherries exhibiting slightly higher levels of expression than the other stages. No expression was detected for this gene in the root, stem or leaves of C. arabica. FIG. 2 shows another Northern Blot experiment examining the expression of CcCP-1 in C. arabica using a new preparation of RNA. For this experiment, the cherries for the four stages were dissected to generate pericarp tissue and grain tissue for each stage of cherry development. Total RNA was then extracted from these tissues. The results obtained show the same temporal pattern of expression for CcCP-1 during cherry development, but this new experiment additionally shows that CcCP-1 is primarily expressed at high levels only in the grain tissue of the cherries. No significant expression of the CcCP-1 gene is seen in the coffee cherry pericarp. This latter result supports the role of this gene product in the exclusive alteration of the protein, peptide and amino acid profile of the coffee grain under normal growing conditions.

We have generated EST libraries from coffee leaves, as well as from seed and pericarp tissues that have been dissected from different stages of developing coffee cherries. The detection of CcCP-1 ESTs in the different libraries (shown below—see Table 3) also demonstrates that this gene is expressed strongly in the grain, but is not expressed significantly in the pericarp or in leaves. The expression pattern of CcCP-1 during seed development is similar to that seen for its proposed homologous sequence of Vicia sativa, (CPR4 gene: Fischer, J. et al 2000. Plant Molecular Biology, 43, 83-101). These authors showed that CPR4 is not detected by Northern blotting in leaves, roots, or stem, further strengthening the argument that the CcCP-1 is grain specific. Altering the expression of CcCP-1 specifically in the grain as suggested here, such as by using a grain specific promoter for an antisense construct of CcCP-1 or an over-expression construct of CcCP-1, would not be expected to interfere with the metabolism in other tissues.

TABLE 3

| Gene Name | Number of ESTs | | | | | | |
|---|---|---|---|---|---|---|---|
| | Seed 18w | Whole Cherries 22w | Seed 30w | Seed 42w | Seed 46w | Pericarp | Leaf |
| CcCP-1 | 0 | 0 | 4 | 0 | 15 | 0 | 0 |

Optional alignment for CcCP-1 (FIG. 2A) shows that this cDNA encodes a cysteine proteinase.

The Northern blot analysis shown in FIG. 3 demonstrates that the coffee cysteine proteinase inhibitor gene CcCPI-1 gene is expressed in the *C. arabica* coffee cherry at all stages tested. However, in contrast to the expression seen for the cysteine proteinase CcCP-1, CcCPI-1 exhibits higher expression in the two early stages of coffee cherry development (small green and large green), and this gene is expressed at lower levels in the two later stages of cherry development. This expression pattern is consistent with the present hypothesis that the cysteine proteinase inhibitor protein (CcCPI-1) controls the activity level of a cysteine proteinase that is specifically expressed in seeds, such as CcCP-1, in the coffee cherry. A controlling protein such as the cysteine proteinase inhibitor protein can be expected to be expressed earlier than its target protein if it is necessary to control the level of activity of its target protein continuously from the time that the target protein is expressed. No expression was detected for this gene in the root, stem or leaves of *C. arabica*. It is noted that the similarity of the expression patterns for CcCP-1 and CcCPI-1 are consistent with the present hypothesis that these proteins could interact functionally.

The Northern blotting results (FIG. 3) indicated that CcCPI-1 is expressed at all stages in the coffee cherry. However, this experiment did not determine whether the expression was in the whole cherry, or only in the pericarp or grain. Expression in the leaf was also not tested. However, the expression of CcCPI-1 in the different Est libraries (shown in Table 4 below) demonstrates that this gene is expressed specifically only in the grain, no expression was detected in the pericarp or leaves. This result further suggests that CcCPI-1 controls the activity level of a cysteine proteinase that is specifically expressed in seeds such as CcCP-1.

TABLE 4

| Gene Name | Number of ESTs | | | | | | |
|---|---|---|---|---|---|---|---|
| | Seed 18w | Whole Cherries 22w | Seed 30w | Seed 42w | Seed 46w | Pericarp | Leaf |
| CcCPI-1 | 0 | 0 | 1 | 0 | | 0 | 0 |

The Northern blot analysis shown in FIG. 4 demonstrates that the coffee cysteine proteinase inhibitor gene CcCPI-1 gene is expressed differently in the cherries of *C. canephora* (*robusta*) versus the cherries of *C. arabica*. First, the data of FIG. 4 shows that the CcCPI-1 gene is expressed slightly earlier in *C. arabica*. Secondly, and more importantly, the CcCPI-1 gene is expressed in significantly higher levels in the *C. canephora* cherries. This difference in expression probably affects the level of the cysteine proteinase activity found in *C. arabica* versus *C. canephora* cherries. Because this class of protein is widely associated with insect resistance in plants, it is also likely that the high expression of the CcCPI-1 gene in C. canephora contributes to the higher disease resistance often seen for robusta varieties versus arabica varieties.

RT-PCR Analysis of CcCP-1 Expression During Grain Germination

To determine the expression of CcCP-1 during coffee grain germination, coffee fruit were harvested at the mature stage, rinsed with water, and the pericarp was taken off (each fruit normally contains two grains). The grain obtained were allowed to dry for one week in the open at room temperature. Before germination, the parchment and the silverskin (testa) of each grain were manually removed and grains were then sterilized by placing in 1% (w/v) sodium hypochlorite for 1 hour, and then washed twice by sterilized, distilled water. For germination, 150 sterilized grains were placed individually in test tubes containing 10 ml of solid Heller growth medium H15, containing salts of Heller (Heller, 1953) and 7 g/1 agar and they were then incubated at 25° C., with 8 hours of light daily.

Three sets of ten grain were taken after 2 days, 3 days, 5 days, 1 month and 2 months of germination, and were immediately frozen in liquid nitrogen and stored at −80° C. until RNA extraction. For the 1 and 2 month germination samples, the radicles associated with these samples were excised at sampling time and were frozen separately from the grain. Thirty sterilized grain were taken at T=0 and frozen for use as a T(0) control. 4 µg of DNase-treated total RNA extracted from each sample was used to synthesize cDNA using hexamer oligonucleotides according to the protocol of the Superscript II Reverse Transcriptase (Invitrogen, Carlsbad, Calif.). A fragment of the coffee ribosomal protein L39 gene was amplified for each cDNA sample as a control for the cDNA synthesis step. The PCR reactions were performed using 50 µl reactions containing 10 µl of a 1/100 dilution of the cDNAs, 1 µM each primer, 5 µl of 10× ThermoPol PCR buffer (10 mM $(NH_4)_2SO_4$, 2 mM $MgSO_4$, 20 mM Tris-HCl, pH 8.8 at 25° C., 10 mM KCl, and 0.1% Triton X-100) and 2.5 units of Taq polymerase (New England Biolabs, Beverly, Mass.). The cycling conditions were 2 mM at 94° C., followed by 35 cycles of 94° C. for 1 mM, 60° C. for 1.5 mM, and 72° C.×2.5 mM. The final extension step was for 7 mM at 72° C. The following primers were used for amplification by PCR: CcCP-1 up 5' ACCGAGGAGGAGTTTGAGGCTACG 3' (SEQ ID NO: 36) and CcCP-1 low: 5' ACGCTTCCCCCAT-GAGTTCTTGA 3' (SEQ ID NO: 37), yielding cDNA products of 726 bp. The primers for the RPL39 protein were:

```
                                    (SEQ ID NO: 38)
A5-1750-upper 5' TGGCGAAGAAGCAGAGGCAGA 3'
```

```
                                    (SEQ ID NO: 39)
A5-1750-lower5' 5' TTGAGGGGGAGGGTAAAAAG 3'
```

RT-PCR was used to determine the expression of CcCP-1 during the different stages of germination. The results obtained demonstrate that CcCP-1 transcripts are detected in the whole grain at all the germination times tested (FIG. 5). It has previously been shown by Fischer, J. et al 2000 (Plant Molecular Biology, 43, 83-101) that RNA of the proposed CcCP-1 homologue CPR4 from *V. sativa* is also expressed in both the embryo axis and the cotyledons of V. sativa seeds during germination.

Western Blot Analysis

The leaf and cherry tissues analysed were from *Coffea arabica* CCCA2, and prior to use, the tissues were stored frozen at −80° C. The grain and pericarp tissues of the cherries at different stages of development were dissected separately with as little thawing of the pericarp as possible. These different tissues were then rapidly ground to a fine powder, such as can be done using liquid nitrogen with a pre-frozen mortar and pestle. A protein extract was prepared from this tissue using a modified version of the extraction procedure described by Tanaka et al., 1986 (Plant Physiology, 81 802-806). The buffers used were:

Tanaka Buffer:

| Sucrose | 0.7M |
|---|---|
| Tris-HCl pH 8 | 0.5M |
| β-mercapto-ethanol | 2% (v/v) |
| NaCl | 0.1M |

And just before using this buffer add:

| EDTA | 5 mM |
|---|---|
| PMSF | 2 mM |

Gel loading buffer:

| Glycerol | 15% (v/v) |
|---|---|
| β-mercapto-ethanol | 2% (v/v) |
| SDS | 3% (v/v) |
| Tris-HCl pH 6.8 | 62.5 mM |

A few hundred milligrams of the frozen ground powders were added to 650 µl of Tanaka buffer. The proteins were extracted with the addition of one volume of Tris saturated phenol pH8 (ie. saturated with 10 mM Tris-HCl pH8). Each sample was mixed vigorously for 20 min and then centrifuged for 20 min at room temperature at 13 000 g. After centrifugation, the proteins are in the phenolic phase. 20 µl samples were kept for analysis (see below) and the remaining proteins in the phenol phase were precipitated overnight at −20° C. following the addition of five volumes of methanol containing 0.1 M ammonium acetate. Subsequently, the samples were centrifuged for 20 min at room temperature at 13 000 g, and the resulting pellets were washed two times in 500 µl of methanol containing 0.1 M ammonium acetate. The pellets obtained were resuspended in 30 µl of gel loading buffer until protein quantification.

The protein in 20 µl samples of the phenolic phase were also precipitated as above, and the final pellet was resuspended in the sample buffer of the BioRad $D_C$ Protein assay Kit. Quantification of total protein in this sample was carried out using the BioRad $D_C$ Protein assay kit as described by the supplier. Subsequently, all the main samples were adjusted to give 5 µg/µl by addition of gel loading buffer.

Samples containing approximately 50 ug protein of each sample were separated by electrophoresis in an SDS-polyacrylamide gel (12% tris-glycine, (Novex® Invitrogen™). The proteins were then transferred to a PVDF membrane by electroblotting using standard protocols. Non-specific binding sites on the membrane were blocked by incubating the membrane in 10% non-fat dried milk in TBS buffer (Bio-Rad™), for one hour at room temperature or overnight at 4° C. The blotted proteins were probed for two hours at room temperature or overnight at 4° C. with a polyclonal antibody (dilution ⅕₀₀₀ e in TBS 10% non-fat dried milk), raised against the predicted homologue of CPR4 from *Vicia sativa*, which was kindly donated by A. Schlereth and K. Müntz, Institut für Pflanzengenetik and kulturpflanzenforchung (IPK), Germany (A. Schlereth, C. Becker, C. Horstmann, J. Tiedmann and K. Müntz 2000, Journal of Experimental Botany, 51:1423-4433). The membrane was then washed 3 times for 20 minutes in TBS+0.1% Tween 20 buffer. The membrane was subsequently incubated one hour with a secondary antibody labeled with horseradish peroxidase (Goat anti-rabbit Ig, Immunopure®, Pierce™). The membrane was then washed 2 times for 20 minutes in TBS+0.1% Tween 20 buffer, then once for 20 minutes in TBS. The presence of the enzyme coupled to the second antibody was visualized by chemiluminescence detection using the enhanced ECL+® system (Amersham Life Science) as described by the supplier. The results obtained show that a polypeptide of approximately 41 kDa, which corresponds closely with the predicted molecular weight of the CcCP-1 precursor polypeptide (43 735 Da), is detected at all the stages of grain maturation tested, but is not detected in the pericarp tissue (FIG. 6). This protein expression pattern is similar to that seen for the CcCP-1 mRNA (FIG. 2). Another polypeptide of approximately 22 kDa is also detected in the grain at the yellow stage and red stage, but in smaller quantities than 41 kDa polypeptide. The size of this second polypeptide is consistent with the predicted size of the mature form of CcCP-1 (25, 239 Da). The predicted size of the mature CcCP-1 after processing was determined by a protein alignment between the complete ORF sequence of CcCP1 and the sequence of the predicted mature form of CPR4 (*Vicia sativa*—accession# Z99172, 60.9% identity with CcCP1). The N-terminal site of the CPR4 polypeptide processing to generate the mature form was predicted by sequence comparison with other papain-like CPR polypeptides (J. Fisher, C. Becker, S. Hillmer, C. Horstmann, B. Neubohn, A. Schlereth, V. Senyuk, A. Shutov and K. Miintz. 2000 Plant molecular biology 43:83-101). Interestingly, in contrast to the results presented here, where both the precursor and mature forms of CcCP-1 are detected during grain development, only the mature form of the CPR4 polypeptide was detected in developing seeds and also during the germination of *V. sativa* seeds (Fisher and al, 2000).

RT-PCR Analysis of Gene Expression for *robusta* Variety FRT-32.

Different tissues of FRT-32 were prepared and total RNA was extracted from these tissues by the method described earlier. cDNA was prepared from DNase-treated total RNA as described above for the RT-PCR experiments with *arabica* cDNA. Then specific PCR reactions were run using the reaction conditions described above for the RT-PCR experiments with *arabica* cDNA. The specific amplification conditions and oligonucleotide primers used given in the Figure legend for each experiment.

CcCPI-1 a) Optimal alignment for CcCPI-1 (FIG. 6A) showing that this cDNA encodes a cysteine proteinase inhibitor.

b) RT-PCR expression data for CcCPI-1 (FIG. 7) in *arabica* and *robusta*. The PCR reactions were performed as previously described and the cycling conditions and the PCR primers used are given in the Figure legend. These data compliment and extend that data presented earlier for the arabica expression in that it shows CcCPI-1 is only expressed in the grain and not pericarp. Weak expression of this gene was also detected in flowers, a result not seen previously by Northern blot analysis. The RT-PCR expression in *robusta* was also determined (FIG. 7). It is the same expression pattern as seen for *arabica* except that no expression was detected in flowers or in the small green grain. The absence of expression seen for the small green stage of *robusta* is also seen for other genes and is thus not unique to the CcCPI-1 gene.

TABLE 5

Occurrence of Est's for Cysteine Proteinase Inhibitor
genes CPI-2, CPI-3 and CPI-4 in different Est Libraries.

| Cysteine proteinase Inhibitor | Seed 18w | Whole Cherries 22w | Seed 30w | Seed 42w | Seed 46w | Pericarp | Leaf |
|---|---|---|---|---|---|---|---|
| CcCPI-2 | 0 | 2 | 12 | 0 | 1 | 1 | 0 |
| CcCPI-3 | 0 | 0 | 1 | 0 | 2 | 0 | 0 |
| CcCPI-4 | 0 | 0 | 1 | 0 | 0 | 0 | 6 |

CcCPI-2 a) Optimal Alignment for CcCPI-2 (FIG. 8) showing that this cDNA encodes a cysteine proteinase inhibitor.

b) RT-PCR expression data for CcCPI-2 (FIG. 9) in arabica and robusta. The PCR reactions were performed as previously described and the PCR primers used are given in the Figure legend. These data show that CcCP-2 is expressed in all tissues and thus the protein product of this gene probably plays an important role in controlling one or more cysteine proteinases present in these tissues. The numbers of Est's in each library seen in Table 5 above suggest that CPI-2 may be expressed more in grain (seed) at 30 weeks after fertilisation than in leaves, pericarp, or seeds 46 weeks after fertilisation.

CcCPI-3 a) Optimal Alignment for CcCPI-3 (FIG. 10) showing that this cDNA encodes a cysteine proteinase inhibitor.

b) No RT-PCR expression data is currently available for this cysteine proteinase inhibitor. However, the "in silico" expression of this gene, as determined by the number of Est's appearing in each library (Table 5 above), indicates that CcCPI-3 is expressed in coffee grain (present in seed libraries "Seed30w" and "Seed46w" i.e. 30 and 46 weeks). The absence of Est's for this gene in the pericarp, leaf or whole cherry suggests that this gene may be a grain specific gene.

CcCPI-4 a) Optimal Alignment for CcCPI-4 (FIG. 11) showing that this cDNA encodes a cysteine proteinase inhibitor.

b) RT-PCR expression data for CcCPI-4 (FIG. 12) in arabica and robusta. The PCR reactions were performed as previously described and the PCR primers used are given in the Figure legend. The data obtained show that this gene is significantly expressed, in arabica, in leaves, flowers and in grain at the red stage. Because close examination of the original gel (Panel A: arabica) indicates that there are also weak bands detected in the small green grain and large green pericarp lanes, this gene may also be weakly expressed, in arabica, in the grain and pericarp at all the stages of cherry development studied. The data obtained for robusta show that this gene is significantly expressed in leaves, flowers, small green grain and large green grain. Only one Est for CcCPI-4 was found in the seed or pericarp libraries (Table 5 above), indicating that expression of this gene in the grain and/or pericarp is relatively low or is confined to small defined regions of these two tissues.

In each case for the Cysteine Proteinase Inhibitor (CPI) genes, the over-expression or inhibition of the expression of these genes during grain development (that is, under the control of a very strong grain specific promoter such as the coffee 11S promoter) is expected to alter the protein peptide and amino acids profiles in the mature grain (and thus the level of flavour precurors).

Germination and RT-PCR Analysis

Sterilized, dried C. arabica CCCA2 grain (parchment and silverskin removed) were placed individually in test tubes containing 10 ml of solid Heller growth medium H15 and 7 g/l agar and were incubated at 25° C., with 8 h of light daily. After 2 days, 3 days, 5 days, 1 month and 2 months of germination, three grains were taken, and when present, the radicles were removed and both grain and radicles were immediately frozen in liquid nitrogen and stored at −80° C. until RNA extraction. Similarly dried and sterilized non-germinated grains (T0) were used as control. RNA was extracted from the grain samples as described earlier. DNase-treated total RNA extracted from each sample was used to synthesize cDNA using oligo $(dT)_{20}$ as a primer according to the protocol of the Superscript II Reverse Transcriptase kit (Invitrogen, Carlsbad, Calif.). A PCR reaction was then carried out using aliquots of each cDNA reaction. (50 µl reactions containing 10 µl of the 1/10 diluted cDNAs, 1 µM each primer, 5 µl of 10× ThermoPol PCR buffer, 200 um dNTPs and 2 units of Taq polymerase (New England Biolabs, Beverly, Mass.). The cycling conditions were 2 min at 94° C., 40 cycles of 94° C. for 1 min, 54° C. for 1.5 min, and 72° C.×2.5 min. The final extension step was for 7 min at 72° C. PCR primers were CP-4 KDDL61:

```
CP-4KDDL61:
                                   (SEQ ID NO: 40)
5'-GAAGAACTCATGGGGAACAGGAT-3'

CP-4KDDL345:
                                   (SEQ ID NO: 41)
5'-TTATTCAAACCATCACAGGAGCAG-3'
```

Genomic PCR and DNA sequencing of the purified PCR fragments

Genomic DNA of five different coffee varieties (FRT-07, FRT-19, FRT-32, CCCA2, and GPFA57) was used in the PCR reaction described above for the germination RT-PCR expression study. PCR products of the expected size were obtained and these fragments were purified from the gel. The PCR amplified DNA was then subjected to a second round of PCR amplification and the DNA obtained from this sequencing reaction was then sequenced using the same primers as used for the amplification.

Isolation and Characterization of Cysteine Proteinase CcCP-4

Using a collection of Est's (Expressed Sequence Tags) made with RNA isolated from 1) coffee grain at different stages of development, coffee pericarp tissue at different stages of development, and from leaves, we have isolated a full length cDNA encoding a coffee cysteine proteinase which has a C-terminal KDDL (SEQ ID NO: 42) sequence. We have named this cDNA CcCP-4 (KDDL) (FIG. 14). The alignment of the protein encoded by this cDNA with other highly homologous plant cysteine proteinases is shown in FIG. 15. This alignment data, and the related Blast searches, clearly show that the protein encoded by the coffee CcCP-4 (KDDL) sequence is a member of the plant KDEL (SEQ ID NO: 17) containing cysteine proteinase family (FIG. 15). The precise identities between CcCP-4 (KDDL) and the most homologous database sequences is given in Tables 6A and 6B.

TABLE 6A

Identity of the *Coffea canephora* cysteine proteinase CcCP-4 (KDDL) amino acid sequence with the amino sequences of the most homologous GenBank sequences

| *Coffea canephora* cysteine proteinase | Gene name (accesion number) | % identity protein |
|---|---|---|
| CcCP-4 (KDDL) | *Dacus carrota* (JC7787) | 73 |
| | *Vigna mungo* (P12412) | 69 |
| | *Glycine max* Cys1 (AB092555) | 70 |
| | *Glycine max* Cys2 (AB092557) | 68 |
| | *Vicia sativa* (Z34895) | 64 |

TABLE 6B

Identity of the *Coffea canephora* cysteine proteinase CcCP-4 (KDDL) nucleic acid (cDNA) sequence with nucleic sequences of the most homologous GenBank sequences

| *Coffea canephora* cysteine proteinase | Gene name (accesion number) | % identity DNA |
|---|---|---|
| CcCP-4 (KDDL) | *Dacus carrota* (JC7787) | 55 |
| | *Vigna mungo* (P12412) | 61 |
| | *Glycine max* Cys1 (AB092555) | 49 |
| | *Glycine max* Cys2 (AB092557) | 62 |
| | *Vicia sativa* (Z34895) | 60 |

Obviously, the coffee CcCP-4 KDDL sequence obtained has one important difference from nearly all the other sequences shown in FIG. 15, that is, it does not have the expected endoplasmic reticulum (ER) retention sequence (the C-terminal KDEL sequence (SEQ ID NO: 17) but a varient of this sequence, ie. KDDL (SEQ ID NO: 42). By testing the capabilities of variations in the C-terminal KDEL (SEQ ID NO: 17) sequence to direct retention in the ER in plant cells, Denecke et al (Denecke, J., De Rycke, R., and Botterman, J. 1992 EMBO J. 11, 2345-2355) have previously shown that C-terminal variants such as SDEL (SEQ ID NO: 43), KDDL (SEQ ID NO: 42), KDEI (SEQ ID NO: 44) and KDEV (SEQ ID NO: 45) can produce a complete loss of endoplasmic reticulum retention function. Therefore, the presence of the KDDL (SEQ ID NO: 42) sequence in the coffee homologue of the plant KDEL (SEQ ID NO: 17) cysteine proteinase was unexpected. Table 7 shows that the unigene containing the cDNA CcCP-4 (KDDL) has 21 Est's. Therefore, we then examined the sequence of other Est's in this unigene and we found that seven of these Est's contained good sequence data for the KDDL region. Of these seven cDNA sequences, six had the KDDL (SEQ ID NO: 42) sequence and one had a KDEL (SEQ ID NO: 17) sequence. We subsequently isolated the cDNA clone with a KDEL (SEQ ID NO: 17) C-terminal sequence and obtained the complete sequence for this partial cDNA clone. The DNA and protein sequences obtained are shown in FIGS. 16 and 17 respectively.

TABLE 7

Number of Est's in the unigene containing the full length cDNA CcCP-4 (KDDL).

| | | Number of ESTs | | | | | |
|---|---|---|---|---|---|---|---|
| Cysteine proteinase Name | | Seed 18w | Whole Cherries 22w | Seed 30w | Seed 42w | Seed 46w | Peri-carp | Leaf |
| CcCP-4 | 125103 | 0 | 0 | 8 | 0 | 13 | 0 | 0 |

The cDNA encoding the sequence for CcCP-4 (KDEL) shown in FIG. 16 is only a partial cDNA, that is, it is only 817 bp long versus 1336 for the full length cDNA clone CcCP-4 (KDDL)). The partial cDNA CcCP-4 (KDEL) has 8 single nucleotide residue changes from the equivalent sequence found in the cDNA clone CcCP-4 (KDDL), although only two of these nucleotide changes lead to a change in the amino acid sequence of the open reading frame (FIG. 17). In the 3' untranslated region, there are 3 clear nucleotide changes. In addition, there is also an insertion of 12 nucleotides in 3' untranslated region of the CcCP-4 (KDEL) cDNA sequence that appears to be within a micro-satellite region. The data just presented uncovered two different and important molecular markers for these two alleles of the coffee CcCP-4 gene, one is an SNP associated with the functionally important KDEL (SEQ ID NO: 17) site, and the other is a microsatellite marker associated with the 3' untranslated region of this gene. The latter point is important as microsatellite sequences are usually considered genetic markers with high variability and therefore it is likely that other alleles of this gene could be found using this microsatellite containing region.

In order to examine the distribution of the two alleles of the CcCP-4 gene identified above in different varieties of *arabica* and *robusta*, a small region of the genomic sequence harboring the CcCP-4 gene was amplified by PCR from five different genotypes. The PCR fragments of the expected size (207 base pairs) were obtained from each genomic DNA sample and these PCR products were gel purified and then re-amplified to generate sufficient DNA for direct DNA sequencing of the PCR product. The results obtained from the sequencing reactions are shown in FIG. 18. The sequencing chromatograms for the five sequences show that the two *arabica* varieties tested clearly had KDEL (SEQ ID NO: 17) sequences and the three *robusta* varieties examined had KDDL (SEQ ID NO: 42) sequences. This result implies that the KDDL (SEQ ID NO: 42) allele could be restricted to *robusta* varieties, and that it is not found in *arabica* varieties. While no KDEL (SEQ ID NO: 17) sequence was found in the three *robusta* varieties studied here, the discovery of one KDEL (SEQ ID NO: 17) sequence in the Cornell Est library indicates that this allele can exist in at least some *robusta* clones.

The expression of the CcCP-4 gene was studied using Northern blot and RT-PCR analysis. FIG. 19 shows the result obtained from the Northern blot experiment using RNA extracted from different developmental stages of coffee grain and pericarp, as well as RNA isolated from roots, young leaves, stems, and flowers of an *arabica* variety. The data obtained using a CcCP-4 (KDDL) probe, which has approximately 98% homology with the known DNA sequence of the CcCP-4 (KDEL) allele, showed that CcCP-4 is expressed only in the grain. No expression was detected in the pericarp, or in the roots, stem, flowers, and leaves. Due to the very high level of identity between the two alleles, the CcCP-4 (KDDL) probe is expected to hybridize to transcripts from both alleles. A similar experiment using RT-PCR analysis also showed the same expression profile for the CcCP-4 gene.

Expression of CcCP-4 was also studied in the whole seed during germination using RT-PCR analysis. This experiment used primers that are common to both the CcCP-4 KDEL and the CcCP-4 KDDL alleles. The results of this experiment are shown in FIG. 20. CcCP-4 transcripts were detected at all the germination stages tested, although the level of transcripts appeared to dip slightly at 3 days and then begin to increase again as germination progressed (with the highest levels in 1 and 2 month samples).

Ling et al. (Ling, J.-Q., Kojima, T., Shiraiwa, M., and Takahara, H., 2003 Biochim. Biophys. Acta 1627, 129-139 have isolated two cDNA from soybean cotyledons encoding KDEL containing cysteine proteinases. These two cDNA had a 93.5% similarity at the DNA level, and were expressed in roots, flowers, and during seed development. No expression was detected by Northern blotting in developing or mature seeds, although expression was detected in mature pods. A cDNA encoding a KDEL (SEQ ID NO: 17) containing cysteine proteinase was also isolated from carrot (Sakuta, C., Oda, A., Konishi, M., Yamakawa, S., Kamada, H., and Satoh, S. 2001 Biosci. Biotechnol. Biochem. 65, 2243-2248.) Transcripts of this gene were detected in mature dry seeds, and in whole germinating seeds at day 2 and day 3 after imbibition. The expression of this gene in other carrot tissues or during seed development was not presented. Another KDEL (SEQ ID NO: 17) containing protein, and its corresponding cDNA have been isolated from V. sativa (Fischer, J, Becker, C., Hillmer, S., Horstmann, C., Neubohn, B, Schlereth, A., Senyuk, V., Shutov, A., and Muntz, K. (2000) Plant Molecular Biol. 43, 83-101.). Using Northern blotting, transcripts for this gene were detected in the cotyledons during germination, but not in the embryo axis of the germinating seeds. No transcripts were detected in maturing seeds, mature seeds, or in leaves and roots.

The results presented here show that the coffee KDEL (SEQ ID NO: 17) type cysteine proteinase exhibits some novel, and unexpected features. First, we have discovered that robusta coffee grain expresses a KDEL (SEQ ID NO: 17) type CP gene which has a single mutation in the sequence coding for the KDEL (SEQ ID NO: 17) region resulting in change from KDEL (SEQ ID NO: 17) to KDDL (SEQ ID NO: 42). Based on the data of Denecke et al. (1992), this particular alteration in the retention sequence is expected to alter the cellular localization and/or control of the robusta CcCP-4 (KDDL) protein. We propose that the presence of a transcribed copy of the CcCP-4 KDDL gene can produce a significant change in the peptide/amino acid profile in the coffee grain relative to varieties with the CcCP-4 KDEL sequence. We have also shown here that the KDEL (SEQ ID NO: 17) type cysteine proteinase of coffee, while showing the expected expression during grain germination, is also unexpectedly expressed during all the grain development stages studied. As noted above, so far, there are no clear data in the published literature demonstrating a significant expression of a KDEL (SEQ ID NO: 17) type cysteine proteinase during seed development in other plants, although its transcripts have been detected in mature carrot seeds (Sakuta et al., 2001).

The novel properties of the coffee KDEL (SEQ ID NO: 17) type cysteine proteinase presented above probably have an important effect on the peptide and amino acid profiles in the mature grain of arabica and robusta, and therefore alter this pool of critical coffee flavour precursors. Considering that transcripts for the KDEL (SEQ ID NO: 17) type cysteine proteinase are present in the mature grain, it is also possible that the KDEL (SEQ ID NO: 17) type protein could be activated during the wet processing of coffee and thereby further alter the peptide/amino acid profile of wet process coffee grain. The work described has generated molecular markers (SNP's and a microsatellite marker) that can be used in classical selection and breeding work to obtain coffee varieties with specific alleles of the KDEL (SEQ ID NO: 17) type cysteine proteinase gene (which will have concomitant alterations in protein/peptide/amino acid profiles). For example, varieties of robusta could be selected/bred which have only the CcCP-4 KDEL (SEQ ID NO: 17) allele, or have only low expression levels of the CcCP-4 KDDL allele. Further, using genetic modification techniques it can be envisioned to alter the KDEL (SEQ ID NO: 17) type cysteine proteinase activity in coffee, or in other plants, by the seed specific over-expression of the KDEL (SEQ ID NO: 17) or KDDL (SEQ ID NO: 42) type cysteine proteinases. Alternatively, the levels of the KDEL (SEQ ID NO: 17) type cysteine proteinase can be reduced using antisense, sense or RNAi technologies. In both cases, the protein/peptide/amino acid pool in the resulting transformed plants will be altered, leading to new profiles of the protein/peptide/amino acid flavour precursor pools.

The Northern blot analysis shown in FIG. 13 demonstrates that the coffee aspartic proteinase CcAP-2 gene is expressed in both the grain and the pericarp of the *C. arabica* coffee cherry at all cherry development stages tested. The CcAP-2 gene also has a relatively high expression in roots. When the film is exposed longer, CcAP-2 expression was also detected in the tissues of *C. arabica* stems, leaf, and flowers.

CcAP-1 and CcAP-2

FIGS. 21 and 22 show that each of CcAP-1 and CcAP-2 encode an aspartic proteinase.

Overexpression and under-expression of the CcCP-1 CcCP-4, CcAP-1 and CcAP-2 proteinase gene sequences and the CcCPI-1,2,3, and 4 proteinase inhibitors in coffee seeds.

It is expected that the major storage protein profile and the amino acid/peptide profile can be changed in the mature coffee grain by altering, either up or down, the expression of one or more of the genes disclosed herein.

Methods for the overexpression of a gene of interest are well known in the art. Such methods consist of creating a chimeric gene of three major components, 1) a promoter sequence at the 5' end of the gene, preferably in the current application a seed specific promoter such as the coffee seed specific promoter described in Marraccini et al. 1999 (Marraccini et al 1999 Molecular cloning of the complete 11 S seed storage protein gene of *Coffea arabica* and promoter analysis in transgenic tobacco plants, Plant Physiol. Biochem. Vol 37, 273-282, and WO 99/02688), 2) the entire coding sequence of the gene to be expressed, and 3) a 3' control region such as the 3' region from the nopaline synthase gene from the T-DNA of the Ti plasmid of *Agrobacterium tumefaciens*. Then, the chimeric gene can be cloned into an *Agrobacterium tumefaciens* transformation vector, and this vector can be transformed into an *Agrobacterium tumefaciens* strain for use in coffee transformation which has been described in detail by Leroy et al 2000, (Leroy et al 2000 Genetically modified coffee plants expressing the *Bacillus thuringiensis* cry1Ac gene for resistance to leaf minor. Plant Cell Reports 2000, 19, 382-389). Plants with stable transformation inserts can then be screened for those which overexpress the specific genes used in the transformation experiment specifically in mature seeds using methods such as detection of gene overexpression or protein activity overexpression versus seeds from mock transformed plants.

For example, a person well skilled in the art can produce a recombinant construct composed of 1) the longest coffee 11S gene promoter sequence described in Marraccini et al. (1999), 2) the full length cDNA sequence of CcCP-1, or of CcCP-4 (KDDL) without the poly A tail, and 3) a known transcription terminator sequence such as the well studied nopaline terminator. It is also possible that higher levels of over-expression for the recombinant constructs could result from the substitution of the 5' non-coding region of the CcCP4 or other cDNA sequences with the 5' non-coding region of the coffee 11S gene or the 5' non-coding regions of other strong seed specific promoters of either coffee or other related plant species. The recombinant gene sequences can then be inserted into an appropriate site of the *Agrobacterium* T-DNA vector described in Leroy et al. The T-DNA vector thus constructed can be put into an appropriate *Agrobacterium* strain, such as the strain described in Leroy et al., and the T-DNA containing *Agrobacterium* can be used to transform coffee following the method detailed in Leroy et al.

It is well known in the art that the expression of known gene sequences can be reduced or completely blocked by antisense suppression and by gene expression using nucleic acid fragments representing less than the entire coding region of a gene, and by nucleic acids that do not share 100% sequence identity with the gene to be suppressed. In this case, the sequences chosen for the particular antisense suppression or cosuppression experiment will replace the full length gene in the chimeric gene construction scheme presented above. The resulting antisense suppression or cosuppression chimeric constructions are again cloned into an *Agrobacterium tumefaciens* transformation vector, and transformed into *Agrobacterium tumefaciens* strain for use in coffee transformation as described above. Plants with stable transformation inserts can then be screened for those with reduced expression of the specific gene sequences used in the seeds of the transformed plants. The reduced expression can be detected by techniques such as Northern blotting; semi quantitative RT-PCR, and/or quantitative RT-PCR.

Another method for reducing, or eliminating, the expression of a gene in plants is to use the small portions of the gene sequences disclosed herein to produce RNA silencing via using RNAi (Hannon, G. J., 2002, Nature, Vol 418, 244-251; Tang et al, 2003, Genes Dev, Vol 17, 49-63). In this approach, small regions of one or more of the sequences disclosed herein are cloned into an *Agrobacterium tumefaciens* transformation vector as described above which has a seed specific promoter and an appropriate 3' regulatory region. This new inserted sequence for RNAi should be constructed so that the RNA produced forms an RNA structure in vivo which result in the production of small double stranded RNA in the transformed cells and whereby these small double stranded RNA sequences trigger the degradation of the homologous mRNA in these transformed cells.

Screening for naturally occurring variations in the CcCP-1, CcCP-4, CcAP-1, CcAP-2, CcCPI-1, CcCPI-2, CcCPI-3, CcCPI-4 genes and creating new mutations in these genes.

The sequences disclosed herein can be used to screen natural populations for allelic variants in these genes. This can be accomplished by using the CcCP-1, CcCP-4, CcAP-1, CcAP-2, CcCPI-1, CcCPI-2, CcCPI-3 and CcCPI-4 sequences as probes in a search for naturally occurring RFLP's (restriction fragment length polymorphisms) in genomic DNA from different coffee plant varieties. A more powerful method to find allelic variants is to use the mutation screening technology associated with the TILLING method (Till, B. J., et al 2003 Large scale discovery of induced point mutations with highthruput TILLING. Genome Research Vol 13, 524-530). In this case, once a specific gene sequence has been isolated and cloned, such as CcCP-1, CcCP-4, CcAP-1, CcAP-2, CcCPI-1, CcCPI-2, CcCPI-3 and CcCPI-4 sequences herein, the mutation screening technique associated with the TILLING method can be used to identify sequence variants between the cloned sequence and the corresponding cDNA or genomic sequence in different varieties. Using PCR primer pairs coding for DNA segments of 700-1100 base pairs, the known cloned gene can be scanned for naturally occurring sequence variations in different varieties. In the ideal situation, one or more sequence variants could also be correlated with a particular phenotypic variation thereby identifying a genetic marker for this phenotypic variant.

Additionally, using the sequences disclosed herein for CcCP-1, CcCP-4, CcAP-1, CcAP-2, CcCPI-1, CcCPI-2, CcCPI-3 and CcCPI-4, application of the full TILLING method can be used to create and detect new mutants in these genes and thus produce plants containing these specific mutants. For example, using the full TILLING method, coffee plants could be created which have specific mutations, such as a missense mutation in the coding sequence which inactivates the gene target of interest.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. An isolated cDNA comprising a nucleotide sequence encoding a polypeptide having cysteine proteinase activity, wherein the amino acid sequence of the polypeptide and the amino acid sequence of SEQ ID No. 16 have at least 95% sequence identity based on the ClustalW alignment method; or the complement of the nucleotide sequence, wherein the complement contains the same number of nucleotides as the nucleotide sequence, and the complement and the nucleotide sequence are 100% complementary.

2. The polynucleotide of claim 1, wherein the nucleotide sequence comprises the nucleotide sequence of SEQ ID No. 15.

3. The polynucleotide of claim 1, wherein the polypeptide comprises the amino acid sequence of SEQ ID No. 16.

4. A vector comprising the polynucleotide of claim 1.

5. A non-native recombinant DNA construct comprising the polynucleotide of claim 1 operably linked to a regulatory sequence.

6. A method for transforming a cell comprising transforming a cell with the polynucleotide of claim 1.

7. A cell comprising the non-native recombinant DNA construct of claim 5.

8. The cell of claim 7, which is selected from the group consisting of a prokaryotic cell, an eukaryotic cell and a plant cell.

* * * * *